United States Patent
Lederman et al.

(10) Patent No.: US 6,410,710 B1
(45) Date of Patent: Jun. 25, 2002

(54) NUCLEIC ACID ENCODING A TRAF-3 DELETION ISOFORM

(75) Inventors: Seth Lederman, New York; Winfried Van Eyndhoven, Bayside, both of NY (US)

(73) Assignee: The Trustees of the University in the City of New York, New York, NY (US)

( * ) Notice: Subject to any disclaimer, the term of this patent is extended or adjusted under 35 U.S.C. 154(b) by 0 days.

(21) Appl. No.: 09/268,544

(22) Filed: Mar. 11, 1999

(51) Int. Cl.[7] .................. C07H 21/04; C12N 15/11; C12N 15/63

(52) U.S. Cl. ............ 536/23.5; 536/23.1; 435/320.1

(58) Field of Search ............ 536/23.1, 23.5; 435/320.1; 424/93.1; 514/44

(56) References Cited

FOREIGN PATENT DOCUMENTS

| WO | WO9533051 | | 12/1995 |
|---|---|---|---|
| WO | WO 97/34473 | * | 9/1997 |

OTHER PUBLICATIONS

Sato et al., 1995, Genbank Accession No. 153498, CD40–associated protein–human.*
Cheng et al., 1995, Gen Bank Accession No. 149272, CD40 receptor–associated factor 1 mouse.*
Hu et al., 1995, Gen Bank Accession No. A55659, TNR-F–associated protein LAP1–human.*
Cheng et al., 1995, Gen Bank Accession No. A55960, CD40 receptor–associated factor 1–human.*
Rothe et al., 1994, GenBank Accession No. l161512, TNF receptor associated factor2–mouse.*
Cheng, Genhong et al. (1995) Involvement of CRAF1, a Relative of TRAF, in CD40 Signaling, *Science* 267: 1494–1498.
Hu, Hong Ming et al. (1994) A Novel Ring Finger Protein Interacts with the Cytoplasmic Domain of CD40, *J. Bio. Chem.* 269: 30069–30072.
Mosialos, George et al. (1995) The Epstein–Barr Virus Transforming Protein LMP1 Engages Signaling Proteins for the Tumor Necrosis Factor Receptor Family, *Cell* 80:389–399.
Sato, T. et al. (1995) A novel member of the TRAF family of putative signal transducing proteins binds to the cytosolic domain of CD40, *FEBS Letters*, 358:113–118.
van Eyndhoven, W.G. et al. (Jul. 1999) TRAF–3 mRNA splice–deletion variants encode isoforms that induce NF–kappaB activation. *Mol. Immunol.* 36(10):647–58.
van Eyndhoven, W.G. et al. (Dec. 1998) A single gene for human TRAF–3 at chromosome 14q32.3 encodes a variety of mRNA species by alternative polyadenylation, mRNA splicing and transcription initiation. *Mol. Immunol.* 35(18):1189–206.
Gamper, C. et al. (Jan.–Feb. 2000) TRAF–3 Interacts with p62 nucleoporin, a Component of the Nuclear Pore Central Plug That Binds Classical NLS–containing Import Complexes. *Mol. Immunol.* 37 (1–2):73–84.

* cited by examiner

*Primary Examiner*—Michael C. Wilson
(74) *Attorney, Agent, or Firm*—John P. White; Cooper & Dunham LLP

(57) ABSTRACT

The present invention provides an isolated TRAF-3 deletion isoform encoded by the nucleic acid sequence shown in FIG. 15 (deletion isoform Δ130 nucleic acid). The present invention also provides an isolated TRAF-3 protein having the amino acid sequence shown in FIG. 16 (Δ130 protein).

4 Claims, 20 Drawing Sheets

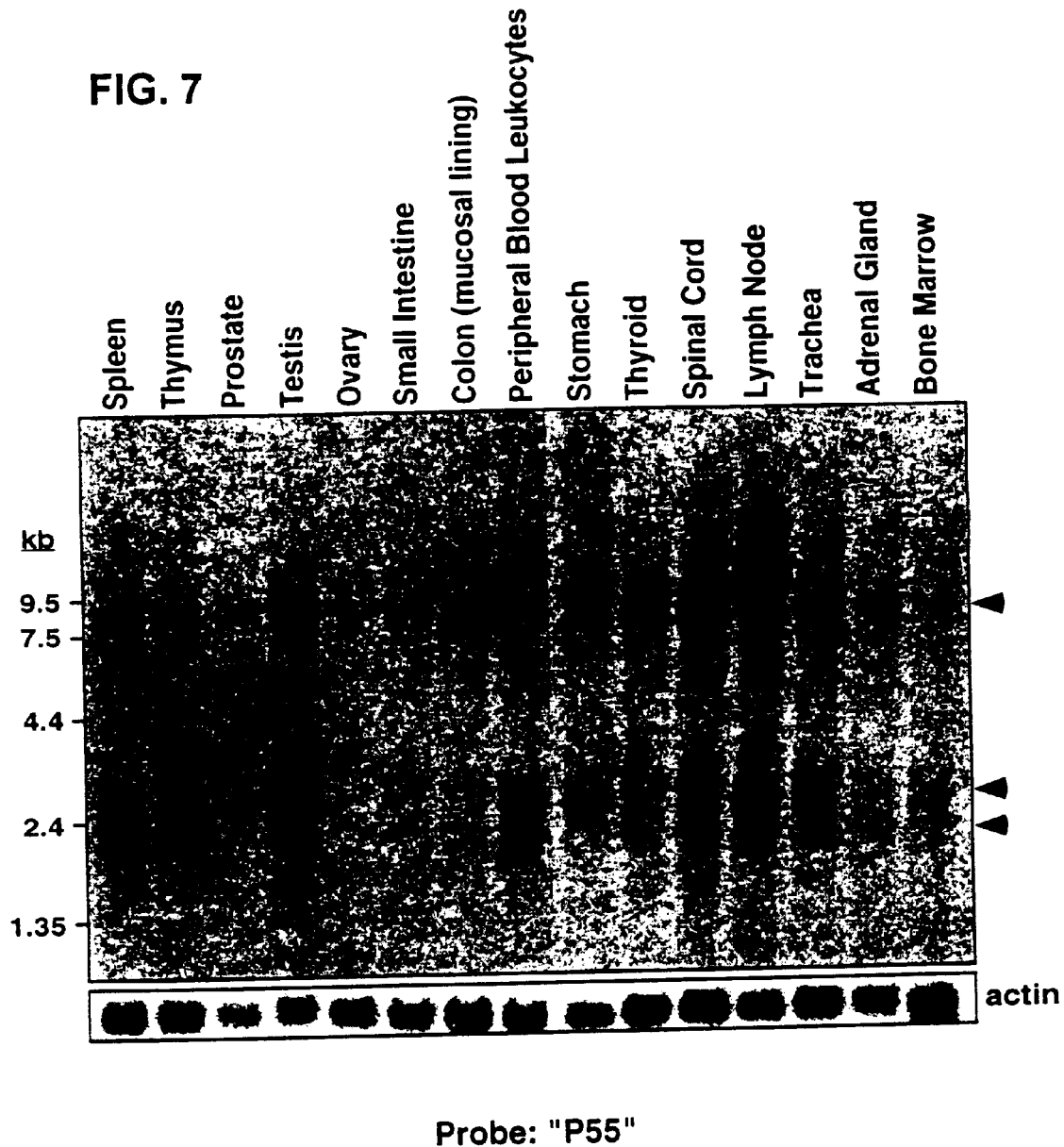

Probe: "P55"

Probe: "3'UTR"

FIG. 14

| exon | IIIb numbering | size (bp) | 3' splice acceptor | 5' splice donor | downstream intron size (Kb) | splice junction class |
|---|---|---|---|---|---|---|
| 1a | --- | --- | --- | CCACCCgtgagcaagaca | 0.8 | --- |
| 1b | 1-200 | --- | --- | CGCGAGgtgtaaggggcc | 54 | 1 |
| 2 | --- | 139 | tttattttacagATGAGG | GAAGAGgtttgctctcag | 32 | --- |
| 3 | 201-462 | 262 | tttccgacagAACTCC | GCTGAGgtaggcgccctc | 1.7 | 2 |
| 4 | 463-514 | 52 | tttgccctgcagCTCTTC | GATAAGgtattctgggt | 3.5 | 0 |
| 5 | 515-619 | 105 | tttcatttcagGTGTTT | CTGCTGgtgagtagcaaa | 0.6 | 0 |
| 6 | 620-787 | 168 | tctgtcttacagGTGCAT | CTGCAGgtgcgggtcctc | 9.5 | 0 |
| 7 | 788-868 | 81 | ctctctctgtagAAAACAC | AGCGAGgtaggggcggcc | 4.0 | 0 |
| 8 | 869-943 | 75 | ttcccgttgcagTTGAGT | TTTCAGgtcagtatccga | 1.8 | 0 |
| 9 | 944-1036 | 93 | ttgctctcgcagGGACA | AAGAAGgtgggctgcaca | 6 | 0 |
| 10 | 1037-1177 | 142 | tttcttttttagGTTTCC | TTACAGgtaagaatctta | 4.5 | 0 |
| 11 | 1178-1352 | 174 | ttggtttggaagCGAGTG | ACACAGgtgaggcagggg | 2 | 1 |
| 12 | 1353-2433 | 6288 | cacctgtggcagGCCTGC | | | |

FIG. 15

TRAF-3 Δ130 / nucleotide sequence

```
CGAGGGAGGCGGCGGCGCCGCCGCCGCCGTGCGCGGAGCCGGGTTGCAGCCCCAGCCGCGGACTTTCCAGCCGCCGGCGCAGCCG
CGGCGGCCGCCGCCGGCTCTTCCCCGCCCGTCATGGGCAGCCCGGGAGCAGAACGCTGCGGAGCCGGCGCGGGAGGAC
GCGCCCGGCCGCCCCTGAGCCGCCGCGCGGCCGCCGAGAACTCCTCTTCCTAAAATGGAGTCGAGTAAAAA
GATGGACTCTCCTGGCGCTGCGCTGCAGAGCTAACCCGCCGCTAAAGCTGCACACTGACCGTAGTGCTGGGACGCCAGTTTT
TGTCCCTGAACAAGGAGGTTACAAGGAGAAAAGTTTGTGAGACCGTGGAGGACAAGTACAAGTGTGAGAAGTGCCACCT
GGTGCTGTGCAGCCGAAGCAGACCCGAGTGTGGGCACATCGTTAAAGATAAGGTGTTTAAGGATAATTGCTGCAAGAGAGAAAT
AAGTCCAAAATGTACAGCGTGTCAAGAGAGCATCGTTAAAGATAAGGTGTTTAAGGATAATTGCTGCAAGAGAGAAAT
TCTGGCTCTTCAGATCTATTGTCGGAATGAAAGCAGAGGTTGTGCAGAGCAGTTAACGCTGGACATCTGCTGGTGCA
TTTAAAAATGATTGCCATTTGAAGAACTTGAAAGAAAAGTCTTGAGGAAAGACCT
GCGAGACCACGTGGAGAAGGCGTGTAAATACCGGGAAGCCACACTGCAAGAGTCAGGTTCCGATGATCGC
GCTGCAGCGAGTGATAGACAGAAGAAACTGAAGAGCTTGACAAGAGATCCGCCCTTCCGCAGAACTG
GGAGGAAGCAGAGACAGCATGAAGAGCAGCGTGGAGTCCCTCAGAACCGCGTGACCGAGCTGGAGAGCGTGGACAAGAG
TGCGGGGCAAGTGGCTCGGACACACAGGCCTGCTTCCAGGTTCATGACCAGATGTCGAGTGCTCATCTGGAAGAT
CATCCGCTAGCGACCGACTACAAGCGGCGGAAGCAGGAGGCCGTCATGGGGAAGACCCCTGTCCCTTACAGCCAGCCTTTTCTACACTGG
TCGCGACTACAAGCGGCGGAAGCAGGAGGCCGTCATGGGGAAGACCCCTGTCCCTTACAGCCAGCCTTTCTACACTGG
TTACTTTGGTTATAAGATGTGTGCCAGGTCTACCTGGAACGGGACGGGATGGGAAGGGACGCACTCTGCTGTT
TTTTGTCATCATGCGTGGAGAATATGATGCCCTGCTTCCTTGCCGTTAAGCAGAAAGTGACACTCATGCTGATGGA
TCAGGGTCCCTCTCGACGTCATTGGGAGATGCATTCAAGCCCGACCCCAACACAGCAGCAGCTTCAAGAAGCCACTGG
AGAGATGAATATCGCCTCTGGCTGCCCAGTCTTTGTGCCCAAACTGTTCTAGAAAATGGACATATATTAAAGATGA
TACAATTTTATTAAAGTCATAGGTGGATACTTCGATCTCGACTTGCCCGATCCCTGATAAGTAGCTGGGAGGTGGATTTAGC
AGAAGGCAACTCCTCTGGGGATTTGAACCGGTCTGTCTTCACTGAGGTCCTCGCGCTCAGAAAAGGACCTTGTGAGA
CGGAGGAAGCGGCAGAAGCCGACGCGTGCCGGGAGGCCACGCTGAGCACACCTGACACGTTTATAATAGA
CTAGCCACACTTCACTCTGAAGAATTATTTATCCTTCAACAAGATAAATATTGCTGTCAGAGAAGTTTTTCATTTTCA
TTTTTAAAGATCTAGTTAATTAAGGTGGAAAACATATATGCTAAACAAAGAAACATGATTTTCTTCCTTAAACTTG
AACACCAAAAAACACACACACACACGTGGGATAGCTGGACATGTCAGCATGTAAGTAAAGGAGAATTATT
GAAATAGTAATGCAATTCTGATATCTTCTTTCTAAAATTCAAGAGTGCAATTTGTTTCAAATACAGTATATTGTCTA
TTTTTAAGGCCCTCCAAAAAAAAAAAAAATTCCGGCCG
```

FIG. 16

TRAF-3 Δ130 / amino acid sequence

MESSKKMDSPGALQTNPPLKLHTDRSAGTPVFVPEQGGYKEKFVKTVEDKYKCEKCHLVLCSPKQTECGHRFCESCMA
ALLSSSSPKCTACQESIVKDKVFKDNCCKREILALQIYCRNESRGCAEQLTLGHLLVHLKNDCHFEELPCVRPDCKEK
VLRKDLRDHVEKACKYREATCSHCKSQVPMIALQRVIDSQAEKLKELDKEIRPFRQNWEEADSMKSSVESLQNRVTEL
ESVDKSAGQVARNTGLLESQLSRHDQMLSVHDIRLADMDLRFQVLETASYNGVLIWKIRDYKRRKQEAVMGKTLSLYS
QPFYTGYFGYKMCARVYLNGDGMGKGTHLSLFFVIMRGEYDALLPWPFKQKVTLMLMDQGSSRRHLGDAFKPDPNSSS
FKKPTGEMNIASGCPVFVAQTVLENGTYIKDDTIFIKVIVDTSDLPDP

FIG. 17 TRAF-3 Δ221 / nucleotide sequence

```
CGAGGGAGCGCGGCGGCGGCCGCGTGCGCGAGCCGGGGTTGCAGCCGCCAGCCCGGGACTTTCCAGCCGGCGGCGGCAGCCG
CGGCGGGCCGCCGGCTCTTCCCCGCGCCCCTCATGGGCAGCCCGGGAGCAGCGCTGCGGACCGCCGGGGGAGGAC
GCGCCCGGCCGCGCCCTGAGCCGGCGGCGGACGGCGAGCGCGAGAACTCCTCTTCCTAAAATGGAGTCGAGTAAAAA
GATGGACTCTCCTGGCCGCGCTGCAGACTAACCCGCCCTAAAGCTGCACACTGACCGTGCTGGGACGCCAGTTTT
TGTCCCTGAACAAGGAGGTTACAAGACAGACCGAGTTGTGAGGCACCGTGGAGGACAAGTACAAGTGTGAGAAGTGCCACCT
GGTGCTGTGCAGCCCGAAGCAGACAGAGCCAGTGTGGGCACCGCTTCTGCGAGAGCTGCATGCGCCCTGCTGAGCTCTTC
AAGTCCAAAATGTACAGCCGTGTCAAGAGACATCGTTAAAGATAAGCCAGTGATAGACAGCCAAGCAGAGAAACTGAA
GGAGCTTGACAAGGAGATCCGGCCTTCGGAGAGCCCTTGAGAGCGTGGGAGGAAGCAGACAGCATGAAGAGCAGCCTGGAGTCCCT
CCAGAACCGCGTGACCGAGCTGGAGCTGTCGAGTGTGCACGACATCCCGCTAGCGACACAAGTGGCTCGGAACACAGGCCTGCTTCCAGTCCT
CCAGCTGAGCGCGGCAGCCAGATGACCAGATGGAGTCGCTCATCTGGAACATTCGCGACTACAAGCGGCGAACAGGGCTTCATCATGGG
GGAGACCCCAGTACAATGGAGTCGCTCATCTGGAAGATTCGCGACTACAAGCGGCGAACAGGAGGCCGTCATGGG
GAAGACCCTGTCCCTTTACAGCCAGCCTTTCTACACTGGTTACTTTGGCTATAAGATGTGTGCCAGGGTCTACTGAA
CGGGGGACGGGATGGGGAAGGGACGCCACTTGTCGTCATGTCGATGATCAGGGTCCTCTCGACGTCATTTGGGAGATGCATTCAA
TTGGCCGTTTAAGCAGAAGTGACACTTCAAGAGCCAGCTTCAAGAGACCATGAATCGCCTCGGCTGCCAGTCTTGTGGC
GCCCGACCCCAACAGCAGCTTCAAGAGACCCACTGGAGAGATGAATATCGCCTCGGCTGCCAGTCTTGTGGC
CCAAACTGTTCTAGAAAATGGACATATATTAAGATGATACAATTTTATTAACATCATAGTGATAACTCCGGCCGATCT
GCCGATCCTGATAAGTAGCTGGGAGGTGGATTTAGCAGAAGGCAACTCCTCTGGGGATTTGAACCGGTCTGTCT
TCACTGAGGTCCTCGCGCTCAGAAAGGACCTTGTGAGAACGGAGGAAGCGGCAGAAGGCGAGACGCGTGCCGGCGGAG
GAGCCACGCCGTGAGCACGCTGAGAGAAGGTTTTCATTTTAAAGATCTAGTTAATTAAGGTGGAAAACATATAT
CAAGATAAATATTGCTGTCAGAGAGAAGGTTTTCATTTTAAAGATCTAGTTAATTAAGGTGGAAAACATATAT
GCTAAACAAAGAAGAAACATGATTTTCTTTTGTTAAGTAAAAAGGAGAATTATGAAATAGTAATGCAATTCTGATATCTTCTTTCTAAAATT
GCTGGACATGTCAGCATGTTAAGTAAAAAGGAGAATTATGAAATAGTAATGCAATTCTGATATCTTCTTTCTAAAATT
CAAGAGTGCAATTTTGTTTCAAATACAGTATATTGTCTATTTTTAAGGCCTCCAAAAAAAAAAATTCCGGCCG
```

FIG. 18 TRAF-3 Δ221 / amino acid sequence

```
MESSKKMDSPGALQTNPPLKLHTDRSAGTPVFVPEQGGYKEKFVKTVEDKYKCEKCHLVLCSPKQTECGHRFCESCMA
ALLSSSSPKCTACQESIVKDKRVIDSQAEKLKELDKEIRPFRQNWEEADSMKSSVESLQNRVTELESVDKSAGQVARN
TGLLESQLSRHDQMLSVHDIRLADMDLRFQVLETASYNGVLIWKIRDYKRRKQEAVMGKTLSLYSQPFYTGYFGYKMC
ARVYLNGDGMGKGTHLSLFFVIMRGEYDALLPWPFKQKVTLMLMDQGSSRRHLGDAFKPDPNSSSFKKPTGEMNIASG
CPVFVAQTVLENGTYIKDDTIFIKVIVDTSDLPDP
```

NUCLEIC ACID ENCODING A TRAF-3 DELETION ISOFORM

The invention disclosed herein was made with Government support under NIH/NCI Grant No. RO-1-CA55713 and Grant No. 5-T32-GM07367 from the Department of Health and Human Services. Accordingly, the U.S. Government has certain rights in this invention.

Throughout this application, various references are referred to in the text within parentheses in full or within parentheses by number. Disclosures of these publications in their entireties are hereby incorporated by reference into this application to more fully describe the state of the art to which this invention pertains. Full bibliographic citation for those references referred to by number may be found at the end of this application, preceding the claims.

The following standard abbreviations are used throughout to refer to amino acids:

| | | |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

BACKGROUND OF THE INVENTION

TRAF-3 gene products are signaling molecules that interact with the cytoplasmic tails of CD40 (Cheng et al., 1995; Hu et al., 1994; Sato et al., 1995), other Tumor Necrosis Factor-Receptor (TNF-R) family members (e.g. LTβ-R, CD30, CD27, Ox40) (Mosialos et al., 1995; Gedrich et al., 1996; Boucher et al., 1997; Yamamoto et al., 1998; Vanarsdale et al., 1997; Arch and Thompson, 1998; Kawamata et al., 1998) and the Epstein-Barr virus latent membrane protein, LMP1 (Mosialos et al., 1995). The finding that TRAF-3$^{(-/-)}$ lymphocytes are specifically defective in T-B lymphocyte collaboration, indiates that TRAF-3 gene products are required for signaling events that underlie this function (Xu et al., 1996). Full-length TRAF-3 alone is unlikely to account for such signaling, since over-expression of full-length TRAF-3 fails to induce NF-κB activation (Rothe et al., 1995; Takeuchi et al., 1996; Dadgostar and Cheng, 1998). However, alternative splicing of TRAF-3 transcripts generates mRNA species that encode at least 3 putative isoforms with altered Zn finger domains that may participate in transmitting receptor signals to the nucleus (Sato et al., 1995; Krajewski et al., 1997; van Eyndhoven et al., 1998). Therefore, the present study addressed whether TRAF-3 mRNA splice-deletion variants encode TRAF-3 protein isoforms that are able to induce NF-κB activation.

TRAF-3 is a member of the TRAF (TNF Receptor-associated factor) family of proteins, of which six have been identified (TRAF-1 through 6) (Rothe et al., 1994; Regnier et al., 1995; Ishida et al., 1996; Ishida et al., 1996; Kashiwada et al., 1998; Cheng et al., 1995; Hu et al., 1994; Sato et al., 1995; Mosialos et al., 1995). TRAF-3, like other TRAFs, appears to lack intrinsic catalytic activity, which suggests that TRAF-3 functions as a docking or adaptor molecule for other proteins that mediate signaling events. TRAF family members are related by significant homology in their carboxy-terminal TRAF-C domains (Rothe et al., 1994; Cheng et al., 1995). The TRAF-3 TRAF-C domain is known to be important for the interaction of TRAF-3 with the cytoplasmic tails of TNF-R family receptors (Cheng et al., 1995; Force et al., 1997; Vanarsdale et al., 1997), homo-oligomerization (Cheng et al., 1995; Force et al., 1997; Sato et al., 1995; Pullen et al., 1998) and binding to cytoplasmic proteins such as I-TRAF/TANK (Rothe et al., 1996; Cheng and Baltimore, 1996) and NIK (Song et al., 1997; Malinin et al., 1997). In addition to the TRAF-C domain, TRAF-3 contains an amino-terminal RING finger domain, five atypical Zn finger motifs, an iso-leucine zipper domain and a TRAF-N domain (Cheng et al., 1995; Hu et al., 1994; Sato et al., 1995; Mosialos et al., 1995). In TRAF-2 and TRAF-5, the RING finger and Zn finger domains have been shown to play important roles in mediating NF-κB activation (Takeuchi et al., 1996; Dadgostar and Cheng, 1998). The functional potentials of the TRAF-3 RING finger and Zn finger domains remain enigmatic, since TRAF-3 itself fails to induce NF-κB activation (Rothe et al., 1995; Takeuchi et al., 1996; Dadgostar and Cheng, 1998). However, the TRAF-3 RING finger domain is capable of supporting NF-κB activation in chimeric TRAF-3/5 molecules (Dadgostar and Cheng, 1998).

Alteration of the TRAF-3 Zn finger domain by alternative mRNA splicing was suggested by analysis of the sequences of the initial TRAF-3 cDNA clones isolated. One TRAF-3 cDNA clone (CAP1) contains a 75 bp deletion, relative to 3 other TRAF-3 cDNA clones (termed CRAF1, CD40bp and LAP1) (Cheng et al., 1995; Hu et al., 1994; Sato et al., 1995; Mosialos et al., 1995). In addition, 2 other TRAF-3 mRNA variants containing 156 bp and 168 bp deletions were recently identified (van Eyndhoven et al., 1998). Each of the 3 mRNA species with deleted elements, encodes a putative TRAF-3 protein isoform with an altered number and composition of the Zn fingers. These putative isoforms have been termed, TRAF-3b (Δ25aa), TRAF-3c (Δ52aa) and TRAF-3d (Δ56aa) (Krajewski et al., 1997; van Eyndhoven et al., 1998). Characterization of the human TRAF-3 genomic structure indicated that these 3 TRAF-3 mRNA species result from alternative mRNA splicing (van Eyndhoven et al., 1998). Further analysis of the TRAF-3 gene suggested that a large number of additional splice variants may be generated, since each of the splice junctions of exons 4 through 10 are class "0". Therefore, splice-deletion variants involving any or all of exons 5–10 would maintain open reading frames (ORFs) (van Eyndhoven et al., 1998). However, additional splice-deletion variants have not been characterized and the functions of the identified or predicted splice-deletion variants have not been studied.

SUMMARY OF THE INVENTION

The present invention provides an isolated TRAF-3 deletion isoform encoded by the nucleic acid sequence (SEQ ID NO: 35) shown in FIG. 15 (deletion isoform Δ130 nucleic acid). One embodiment of the present invention is an isolated TRAF-3 protein which comprises the sequence in FIG. 16 (SEQ ID NO: 36) (Δ130 protein). Another embodiment of the present invention is an isolated TRAF-3 deletion isoform encoded by the nucleic acid sequence (SEQ ID NO: 37) shown in FIG. 17 (deletion isoform Δ221 nucleic acid). A further embodiment of the present invention is an isolated TRAF-3 deletion isoform protein which comprises the sequence in FIG. 18 (SEQ ID NO: 38) (deletion isoform Δ221 protein).

The present invention also provides for a method of inhibiting activation by CD40 ligand of cells expressing CD40 on the cell surface, comprising contacting the cells with a TRAF-3 deletion isoform comprising the sequence shown in FIG. 16 or 18, the isoform protein being present in an amount effective to inhibit activation of the cells.

The present invention also provides for a method for inhibiting an autoimmune response in a subject which comprises administering to the subject an effective amount of a TRAF-3 deletion isoform protein comprising the sequence shown in FIG. 16 or 18 in an effective amount to inhibit an autoimmune response in a subject.

The invention also provides a method for identifying an agent that inhibits CD40-mediated cellular signaling in a cell which comprises: (a) contacting the cell with an agent under conditions wherein CD40-mediated cell activation occurs; and (b) determining whether CD40-mediated signaling is inhibited in the cell in the presence of the agent so as to identify whether the agent inhibits CD40-mediated cellular signaling.

DESCRIPTION OF THE FIGURES

FIG. 7. Characterization of human TRAF-3 mRNA species in human tissues. Human tissue northern blots representing 15 tissues were hybridized with a $^{32}$P labeled cDNA probe containing the complete ORF of TRAF-3 ("P55") or β-actin. Tissue origin and RNA molecular size markers are indicated on top and to the left, respectively.

(FIG. 8A) Poly (A)$^+$ RNA from several B cell lines (BA, Ramos 2G6, Daudi, Raji) and several T cell lines (B2.7, D1.1, CEM, H9) were hybridized with the "P55" probe or β-actin probe. (FIG. 8B) The same blot hybridized with a $^{32}$P labeled cDNA probe representing the 3'-terminal 1.8 kb of exon 12 ("3'UTR"). (FIG. 8C) Shown is a schematic representation of the human TRAF-3 cDNA and the nucleotide homology to murine TRAF-3 (TRAFamn). The percentage homology between human and murine TRAF-3 is depicted by the color or hatching of discrete regions: solid black regions share 85% or more homology, gray regions share approximately 75% and the hatched areas shares 50% or less homology. The relationship of the "P55" and the "3'UTR" probes to the structure of the 8 kb mRNA is depicted below. Asterixes represent the polyadenylation signals at nt positions 2323, 2401 and 7617. Closed circles represent the AUUUA elements at nt positions 1944, 2133, 2335, 2529, 2774 and 7502.

(FIG. 11A) Metaphase spread showing hybridization of the TRAF-3 genomic probe (arrows) to the telomeric region of chromosome 14. (FIG. 11B) Metaphase spread from B cell line Ramos 2G6, carrying the Burkitt's lymphoma translocation t(8;14)(q24.1;q32.3). The TRAF-3 probe is labeled with biotin and detected with streptavidin-rhodamine (red) while a telomeric 14qter probe is labeled with digoxigenin and detected with anti-digoxigenin-FITC (green). On the normal chromosome 14 the signals of the two probes are in close proximity and the level of resolution is not sufficient to establish order. However, the 14qter probe is translocated to derivative chromosome 8, whereas the TRAF-3 probe remains on the derivative chromosome 14. Therefore, the gene for TRAF-3 is located centromeric to the Burkitt's breakpoint in 14q32.3.

FIG. 14. Exon-intron structure of the human TRAF-3 gene. Shown are the exon numbers and their respective position in the TRAF-3 (CRAF-1) cDNA clone (as reported under GenBank accession number U21092). The exon sequences are in upper case, while intron sequences are in lower case. Splice donor (GT) and splice acceptor (AG) are in bold. Splice junction class 0: exon junction falls between two codons; class 1: exon junction falls after first nucleotide of a codon; class 2: exon junction falls after second nucleotide of a codon. The IIIb cDNA clone ends at nt 2433 while exon 12 extends an additional 3855 bp in the 8 kb transcripts (SEQ ID NOS: 12–34).

FIG. 15. Nucleotide sequence of Δ130 TRAF-3 deletion isoform (SEQ ID NO.: 35).

FIG. 16. Amino acid sequence of Δ130 TRAF-3 deletion isoform (SEQ ID NO.: 36).

FIG. 17. Nucleotide sequence of Δ221 TRAF-3 deletion isoform (SEQ ID NO.: 37).

FIG. 18. Amino acid sequence of Δ221 TRAF-3 deletion isoform (SEQ ID NO.: 38).

DETAILED DESCRIPTION

Figure 1:
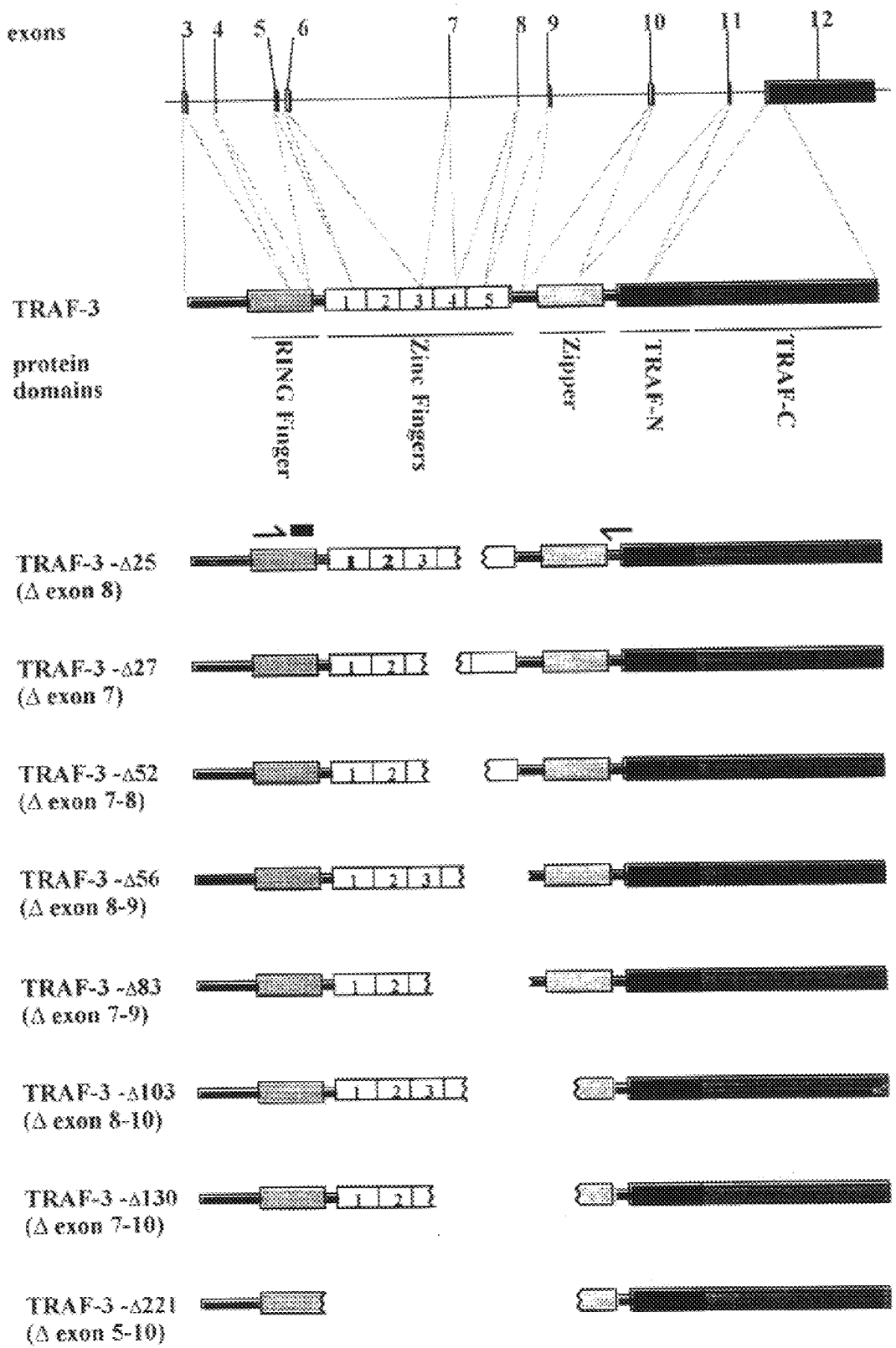
FIG. 1: TRAF-3 mRNA species in Jurkat D1.1 cells. On top is a representation of the TRAF-3 genomic organization of the coding exons (3 through 12). Immediately below is a schematic representation of full-length TRAF-3 cDNA and the 5 predicted protein domains it encodes. Shown below are the 8 distinct mRNA splice-deletion species that encode putative TRAF-3 protein isoforms. All 8 cDNA clones lack mRNA segments from one or more exons that code for the Zn finger domain, thereby altering the composition and number of Zn fingers. TRAF-3 Δ25, Δ52 and Δ56 were previously identified and termed TRAF-3b, TRAF-3c and TRAF-3d, respectively (Krajewski et al., 1997; van Eyndhoven et al., 1998). Above TRAF-3 Δ25, two arrows depict the location of the primers used for PCR that allowed the isolation of the distinct TRAF-3 splice-deletion variant cDNAs from Jurkat T cell line D1.1 mRNA. The hatched bar depicts the location of the end-labeled probe (FF7GEN) used for detection of TRAF-3 specific PCR products.

This invention provides for an isolated TRAF-3 deletion isoform protein encoded by the nucleic acid sequence shown in of FIG. 15 (SEQ ID NO.: 35) (Δ130 TRAF-3 isoform) or FIG. 17 (Δ221 TRAF-3 isoform) (SEQ ID NO.: 37).

The TRAF-3 deletion isoform protein may comprise the sequence shown in either FIG. 16 (Δ130 TRAF-3 isoform) (SEQ ID NO.: 36) or FIG. 18 (Δ221 TRAF-3 isoform) (Seq I.D. No. 38) capable of inhibiting CD40-mediated cell activation.

The present invention provides new TRAF-3 deletion isoforms which were not known to exist previously, although there has been a description of a few splice deletion isoforms of TRAF-3 in PCT International Application No. PCT/US97/05076, PCT International Publication No. WO 97/34473. The present invention provides several new isoforms which have been shown to actually be expressed in cells (i.e., not a theoretical isoform, but one that actually is produced by living cells) and which have been shown to modulate the CD40-mediated cell activation pathway.

The nucleic acid may be an isolated nucleic acid or a purified nucleic acid which nucleic acid is separated from cellular particles substantially. Such isolation or purification would be known to one of skill in the art, see Sambrook, et al. *Molecular Cloning: A Laboratory Manual*, Cold Spring Harbor Press, Cold Spring Harbor, N.Y. (1989).

This invention provides for alleles of the TRAF-3 deletion isoform nucleic acids. This invention provides for human TRAF-3 deletion isoform nucleic acid (with a nucleotide sequence as shown in FIG. 15 or 17) and also provides for the homologous murine TRAF-3 nucleic acid, as well as the homologous TRAF-3 nucleic acids in other species of animals.

The present invention also provides for a TRAF-3 deletion isoform nucleic acid molecule linked to a vector. The vector may be a self-replicating vector or a replicative incompetent vector. The vector may be a pharmaceutically acceptable vector for methods of gene therapy. An example of replication incompetent vector is LNL6 (Miller, A. D. et al. (1989) *BioTechniques* 7:980–990)

The present invention provides an isolated protein comprising a TRAF-3 deletion isoform which comprises the amino acid sequence shown in FIG. 16 (SEQ ID NO.: 36). The present invention also provides an isolated protein comprising a TRAF-3 deletion isoform which comprises the amino acid shown in FIG. 18 (SEQ ID NO.: 38). One embodiment of the present invention is an isolated nucleic acid molecule encoding the TRAF-3 deletion isoform protein. In one embodiment, the nucleic acid molecule is DNA or cDNA. The present invention also provides a vector comprising the nucleic acid molecule operably linked to a transcriptional control sequence recognized by a host cell transformed with the vector. In one embodiment, the vector is a plasmid.

The present invention also provides a method for identifying an agent that inhibits CD40-mediated cellular signaling in a cell which comprises: (a) contacting the cell with an agent under conditions wherein CD40-mediated cell activation occurs; and (b) determining whether CD40-mediated signaling is inhibited in the cell in the presence of the agent so as to identify whether the agent inhibits CD40-mediated cellular signaling. In one embodiment, the agent is a small molecule capable of inactivating a TRAF-3 deletion isoform. In one embodiment, the agent is a competitive inhibitor of a TRAF-3 deletion isoform. In one embodiment, the TRAF-3 deletion isoform is a protein having the amino acid sequence shown in FIG. 16 (SEQ ID NO.: 36) or FIG. 18 (SEQ ID NO.: 38). In one embodiment, the agent is a peptide or a nucleic acid. In one embodiment, the agent is an organic molecule. In one embodiment, the agent is a chiral compound or a racemic mixture of enantiomers. In one embodiment, the cell is a cell which overexpresses the TRAF-3 deletion isoform Δ130 protein having the amino acid sequence shown in FIG. 16 (SEQ ID. NO.: 36). In one embodiment, the cell is a 293T cell.

The present invention also provides a compound identified as an inhibitor of CD40-mediated cell activation.

The present invention also provides a method of inhibiting activation by CD40 ligand of cells expressing CD40 on the cell surface, comprising providing the cells with a TRAF-3 deletion isoform protein or an agent identified by the above method, the protein or agent being present in an amount effective to inhibit activation of the cells.

In one embodiment, the cells are provided with the protein by introducing into the cells a nucleic acid sequence encoding the protein under conditions such that the cells express an amount of the protein effective to inhibit activation of the cells.

In one embodiment, the nucleic acid sequence is operably linked to a transcriptional control sequence recognized by the cell. In one embodiment, the nucleic acid sequence is a plasmid. In one embodiment, the CD40-bearing cells are selected from the group consisting of B cells, fibroblasts, endothelial cells, epithelial cells, T cells, basophils, macrophages, Reed-Steinberg cells, dendritic cells, renal cells, and smooth muscle cells.

In one embodiment, the B cells are resting B cells, primed B cells, myeloma cells, lymphocytic leukemia B cells, or B lymphoma cells.

In one embodiment, the epithelial cells are keratinocytes. In one embodiment, the fibroblasts are synovial membrane fibroblasts, dermal fibroblasts, pulmonary fibroblasts, or liver fibroblasts. In one embodiment, the renal cells are selected from the group consisting of glomerular endothelial cells, mesangial cells, distal tubule cells, proximal tubule cells, parietal epithelial cells, visceral epithelial cells, cells of a Henle limb, and interstitial inflammatory cells. In one embodiment, the parietal epithelial cells are crescent parietal epithelial cells.

In one embodiment, the smooth muscle cells are smooth muscle cells of the bladder, vascular smooth muscle cells, aortic smooth muscle cells, coronary smooth muscle cells, pulmonary smooth muscle cells, or gastrointestinal smooth muscle cells. In one embodiment, the gastrointestinal smooth muscle cells are esophageal smooth muscle cells, stomachic smooth muscle cells, smooth muscle cells of the small intestine, or smooth muscle cells of the large intestine.

The present invention provides a method of providing a subject with an amount of a TRAF-3 deletion isoform protein or an agent identified by the screening method hereinabove, effective to inhibit activation by CD40 ligand of cells bearing CD40 on the cell surface in the subject, comprising: introducing into CD40-bearing cells of the subject, a nucleic acid sequence encoding the protein or an agent identified by the screening method, under conditions such that the cells express in the subject an activation inhibiting effective amount of the protein.

In one embodiment, the introducing of the nucleic acid into cells of the subject comprises: a) treating cells of the subject ex vivo to insert the nucleic acid sequence into the cells; and b) introducing the cells from step a) into the subject. In one embodiment, the subject is a mammal. In one embodiment, the mammalian subject is a human.

The present invention provides a method of treating a condition characterized by an aberrant or unwanted level of CD40-mediated intracellular signaling, in a subject, comprising providing the subject with a therapeutically effective amount of a TRAF-3 deletion isoform protein or an agent identified by the screening method hereinabove, capable of inhibiting CD40-mediated intracellular signaling in cells bearing CD40 on the cell surface.

In one embodiment, the protein is provided by introducing into CD40-bearing cells of the subject, a nucleic acid sequence encoding the protein under conditions such that the cells express the protein. In one embodiment, the condition is organ rejection in a subject receiving transplant organs, or an immune response in a subject receiving gene therapy. In one embodiment, the transplant organ is a kidney, heart or liver. In one embodiment, the condition is a CD40-dependent immune response. In one embodiment, the CD40-dependent immune response is an autoimmune response in a subject suffering from an autoimmune disease. In one embodiment, the autoimmune disease comprises rheumatoid arthritis, Myasthenia gravis, systemic lupus erythematosus, Graves' disease, idiopathic thrombocytopenia purpura, hemolytic anemia, diabetes mellitus, a drug-induced autoimmune disease, psoriasis, or hyper IgE syndrome. In one embodiment, the drug-induced autoimmune disease is drug-induced lupus. In one embodiment, the immune response comprises induction of CD23, CD80 upregulation, rescue from CD95-mediated apoptosis, rescue from apoptosis in a subject undergoing chemotherapy against a tumor, or autoimmune manifestations of an infectious disease. In one embodiment, the autoimmune manifestations are derived from Reiter's syndrome, spondyloarthritis, Lyme disease, HIV infections, syphilis or tuberculosis. In one embodiment, the condition is an allergic response. In one embodiment, the condition is selected from the group consisting of atherosclerosis, reperfusion injury, allograft rejection, organ rejection, and chronic inflammatory autoimmune diseases. In one embodiment, the atherosclerosis is accelerated atherosclerosis associated with organ transplantation. In one embodiment, the chronic inflammatory autoimmune disease is vasculitis, rheumatoid arthritis, scleroderma, or multiple sclerosis. In one embodiment, the condition is dependent on CD40 ligand-induced activation of epithelial cells. In one embodiment, the epithelial cells are keratinocytes, and the condition is psoriasis. In one embodiment, the condition is an inflammatory kidney disease.

The present invention provides for TRAF-3 deletion isoform nucleic acid which is produced by polymerase chain reaction (PCR). An isolated TRAF-3 deletion isoform nucleic acid may be isolated by using PCR. Such reactions are well known to one of skill in the art. [U.S. Pat. Nos. 4,754,065; 4,800,159; 4,683,195 and 4,683,202 provide PCR techniques and methods and these U.S. Patents are hereby incorporated by reference in their entirties.]

In another embodiment of the present invention TRAF-3 deletion isoform nucleic acid may also be a synthetic nucleic acid or a mimetic of a nucleic acid which may have increased bioavailability, stability, potency or decreased toxicity. Such synthetic nucleic acids may have alterations of the basic A, T, C or G or U bases or sugars which make up the nucleotide polymer to as to alter the effect of the nucleic acid.

As used herein, "variants" encompass the following: Variants can differ from naturally occurring TRAF-3 peptide in amino acid sequence or in ways that do not involve sequence, or both. Variants in amino acid sequence are produced when one or more amino acids are substituted with a different natural amino acid, an amino acid derivative or non-native amino acid. When a nucleic acid molecule encoding the protein is expressed in a cell, one naturally occurring amino acid will generally be substituted for another. Conservative substitutions typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

Other conservative substitutions can be taken from Table A, and yet others are described by Dayhoff in the Atlas of Protein Sequence and Structure (1988).

TABLE A

Conservative Amino Acid Replacements

| For Amino Acid | Code | Replace with any of |
|---|---|---|
| Alanine | A | D-Ala, Gly, beta-ALa, L-Cys, D-Cys |
| Arginine | R | D-Arg, Lys, homo-Arg, D-homo-Arg, Met, D-Met, Ile, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Beta-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val, Norleu |
| Phenylalanine | F | D-Phe, Tyr, D-Thr, L-Dopa, His, D-His, Trp, D-Trp, Trans 3,4 or 5-phenylproline, cis 3,4 or 5 phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), Val, D-Val |
| Threonine | T | D-Thr, Ser, D-Ser, allo-Thr, Met, D-Met, Met(O) D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other variants within the invention are those with modifications which increase peptide stability. Such variants may contain, for example, one or more non-peptide bonds (which replace the peptide bonds) in the peptide sequence. Also included are: variants that include residues other than naturally occurring L-amino acids, such as D-amino acids or non-naturally occurring or synthetic amino acids such as beta or gamma amino acids and cyclic variants.

Incorporation of D- instead of L-amino acids into the polypeptide may increase its resistance to proteases. See, e.g., U.S. Pat. No. 5,219,990.

The protein of this invention may also be modified by various changes such as insertions, deletions and substitutions, either conservative or nonconservative where such changes might provide for certain advantages in their use.

In other embodiments, variants with amino acid substitutions which are less conservative may also result in desired derivatives, e.g., by causing changes in charge, conformation and other biological properties. Such substitutions would include for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

Just as it is possible to replace substituents of the scaffold, it is also possible to substitute functional groups which decorate the scaffold with groups characterized by similar features. These substitutions will initially be conservative, i.e., the replacement group will have approximately the same size, shape, hydrophobicity and charge as the original group. Non-sequence modifications may include, for example, in vivo or in vitro chemical derivatization of portions of the protein of this invention, as. well as changes in acetylation, methylation, phosphorylation, carboxylation or glycosylation.

In a further embodiment the protein is modified by chemical modifications in which activity is preserved. For example, the proteins may be amidated, sulfated, singly or multiply halogenated, alkylated, carboxylated, or phosphorylated. The protein may also be singly or multiply acylated, such as with an acetyl group, with a farnesyl moiety, or with a fatty acid, which may be saturated, monounsaturated or polyunsaturated. The fatty acid may also be singly or multiply fluorinated. The invention also includes methionine analogs of the protein, for example the methionine sulfone and methionine sulfoxide analogs. The invention also includes salts of the proteins, such as ammonium salts, including alkyl or aryl ammonium salts, sulfate, hydrogen sulfate, phosphate, hydrogen phosphate, dihydrogen phosphate, thiosulfate, carbonate, bicarbonate, benzoate, sulfonate, thiosulfonate, mesylate, ethyl sulfonate and benzensulfonate salts.

Use of TRAF-3 Deletion Isoforms in Developing Immunomodulatory Agents

TRAF-3 is a cytoplasmic signaling molecule that interacts with the CD40 cytoplasmic tail (and cytoplasmic tails of other TNF-R family members). Full length TRAF-3 inhibits CD40 signaling, but the present invention shows that a number of splice deletion isoforms that are involved in transmitting the CD40 cellular signal. In looking at the nucleotide full length sequence of TRAF-3, one could predict about 65 splice isoforms based on splice donor and acceptor sequences. However, the present invention provides for several different splice isoforms of TRAF-3 which play a role in the activation of a cell based on CD40 signaling. For example, the Experimental Details section hereinbelow describes more fully the following active deletion isoforms: $\Delta56$, $\Delta83$, $\Delta103$, $\Delta130$ and $\Delta221$. The present invention provides for use of these isoforms in identifying inhibitors of CD40 signaling. The present invention provides a method for identifying an agent that inhibits CD40 cellular signaling which comprises (a) contacting a cell with an agent which inhibits the acivity of a TRAF-3 deletion isoform; (b) determining whether CD40 signaling occurs in the cell in the presence of the agent so as to identify whether the agent inhibits CD40 cellular signaling. This application includes evidence that the isoforms termed $\Delta130$ and $\Delta221$ are expressed in cells and are active in CD40 cell activation assays. Therefore, it is preferable that the agent is capable of inhibiting the TRAF-3 deletion isoforms termed $\Delta130$ or $\Delta221$.

Currently, administration of anti-CD40 ligand antibody (e.g., CD154) to a subject is one therapy to inhibit CD40 mediated cellular activation. Relatively large doses of such an antibody are necessary to achieve a blockade of the CD40 pathway. There is a lack of specific inhibitors of the CD40 signaling pathway for use in treating autoimmune diseases or transplant rejection in subjects. This invention provides a new assay useful for identifying agents which would be useful as specific inhibitors of CD40 signaling in a cell. In one embodiment, the assay utilizes a cell which is contacted by an agent and a determination is then made as to whether the agent is capable of inhibiting or modulating the CD40-mediated cell actiation. One can measure upregulation of NF-κB or CD23, for example, to measure the level of cell activation. In another embodiment, the assay utlizes a cell line which overexpresses the TRAF-3 deletion isoform, $\Delta130$ (which hereinbelow is shown to activate cellular activation). The assay comprises contacting the protein isoform with a library of compounds and determining which compounds bind to the TRAF-3 isoforms. These compounds are lead compounds and are then tested for their ability to inhibit cellular activation.

As used herein "small molecule inhibitors" is encompassed by the following characteristics: capable of being administered to a subject with bioavailability so that it is effective at the intracellular level. For example, a nucleic acid molecule that is capapble of being transfected into cells and ultimately inhibiting CD40 mediated cell activation is a small molecule inhibitor.

Another example, is a small peptide, a peptidemimetic; a fragment of an antibody, or a small organic molecule which mimics a region of a TRAF-3 deletion isoform. A small molecule inhibitor also includes a chiral form of a small molecule when the molecule is found to be a racemic mixture.

The present invention provides for an assay for identifying an agent which inhibits CD40 mediated cell activation which comprises contacting a cell capable of undergoing CD40 mediated cell activation with an agent; determining whether the cell is activated in the presence of the agent under conditions which normally produce cell activation; identifying the agent as either capable of inhibiting cell activation or not so capable.

The present invention provides for an agent which inhibits the CD40 cell activation pathway. In one embodiment of the invention, the agent is be a small molecule. In another embodiment, the agent is a mimic of a region of TRAF-3 $\Delta130$ protein or TRAF-3 $\Delta221$ protein sequence as shown in FIGS. 16 and 18. In one embodiment, these isoforms are used in an assay to identify agents which modulate the immune response in a subject. In one embodiment of the present invention, the agent is administered to a subject in a therapeutically effective amount to treat an autoimmune disease or to treat transplant rejection.

This invention provides a method of inhibiting activation by CD40 ligand of cells bearing CD40 on the cell surface, comprising providing the cells with a TRAF-3 deletion isoform protein, the protein being present in an amount effective to inhibit activation of the cells, wherein the TRAF-3 deletion isoform protein is either $\Delta130$ or $\Delta221$ as shown in FIGS. 16 or 18 respectfully.

The present invention further provides a method of inhibiting activation by CD40 ligand of cells expressing CD40 on the cell surface, comprising providing the cells with the peptide of the invention, the peptide being present in an amount effective to inhibit activation of the cells.

In one embodiment, the cells are provided with the peptide by introducing into the cells a nucleic acid sequence encoding the peptide under conditions such that the cells express an amount of the peptide effective to inhibit activation of the cells.

In another emobdiment, the nucleic acid sequence is operably linked to a transcriptional control sequence recognized by the cell. The nucleic acid sequence may be a plasmid. The CD40-bearing cells may be selected from the group consisting of B cells, fibroblasts, endothelial cells, epithelial cells, T cells, basophils, macrophages, Reed-Steinberg cells, dendritic cells, renal cells, and smooth muscle cells. The B cells may be resting B cells, primed B cells, myeloma cells, lymphocytic leukemia B cells, or B lymphoma cells. The epithelial cells may be keratinocytes. The fibroblasts may be synovial membrane fibroblasts, dermal fibroblasts, pulmonary fibroblasts, or liver fibroblasts.

The renal cells may be selected from the group consisting of glomerular endothelial cells, mesangial cells, distal tubule cells, proximal tubule cells, parietal epithelial cells, visceral epithelial cells, cells of a Henle limb, and interstitial inflammatory cells.

The parietal epithelial cells may be crescent parietal epithelial cells.

The smooth muscle cells may be smooth muscle cells of the bladder, vascular smooth muscle cells, aortic smooth muscle cells, coronary smooth muscle cells, pulmonary smooth muscle cells, or gastrointestinal smooth muscle cells.

The gastrointestinal smooth muscle cells may be esophageal smooth muscle cells, stomachic smooth muscle cells, smooth muscle cells of the small intestine, or smooth muscle cells of the large intestine.

The invention provides a method of providing a subject with an amount of a TRAF-3 deletion isoform peptide effective to inhibit activation by CD40 ligand of cells bearing CD40 on the cell surface in the subject, comprising: introducing into CD40-bearing cells of the subject, a nucleic acid sequence encoding the TRAF-3 deletion isoform peptide, under conditions such that the cells express in the subject an activation inhibiting effective amount of the peptide.

The introducing of the nucleic acid into cells of the subject may comprise a) treating cells of the subject ex vivo to insert the nucleic acid sequence into the cells; and b) introducing the cells from step a) into the subject.

The subject may be a mammal. The mammalian subject may be a human.

An embodiment of the present invention is a method of treating a condition characterized by an aberrant or unwanted level of CD40-mediated intracellular signaling, in a subject, comprising providing the subject with a therapeutically effective amount of a TRAF-3 deletion isoform peptide capable of inhibiting CD40-mediated intracellular signaling in cells bearing CD40 on the cell surface.

The peptide may be provided by introducing into CD40-bearing cells of the subject, a nucleic acid sequence encoding the peptide under conditions such that the cells express the peptide according to this method.

The condition may be organ rejection in a subject receiving transplant organs, or an immune response in a subject receiving gene therapy. The transplant organ may be a kidney, heart or liver. The condition may be a CD40-dependent immune response. The CD40-dependent immune response may be an autoimmune response in a subject suffering from an autoimmune disease.

The autoimmune disease may comprise rheumatoid arthritis, Myasthenia gravis, systemic lupus erythematosus, Graves' disease, idiopathic thrombocytopenia purpura, hemolytic anemia, diabetes mellitus, a drug-induced autoimmune disease, psoriasis, or hyper IgE syndrome.

The drug-induced autoimmune disease may be drug-induced lupus. The immune response may comprise induction of CD23, CD80 upregulation, rescue from CD95-mediated apoptosis, rescue from apoptosis in a subject undergoing chemotherapy against a tumor, or autoimmune manifestations of an infectious disease.

The autoimmune manifestations may be derived from Reiter's syndrome, spondyloarthritis, Lyme disease, HIV infections, syphilis or tuberculosis. The condition may be an allergic response. The allergic response may be hay fever or a penicillin allergy. The condition may be dependent on CD40 ligand-induced activation of fibroblast cells. The condition may be selected from the group consisting of arthritis, scleroderma, and fibrosis. The arthritis may be rheumatoid arthritis, non-rheumatoid inflammatory arthritis, arthritis associated with Lyme disease, or osteoarthritis. The fibrosis may be pulmonary fibrosis, hypersensitivity pulmonary fibrosis, or a pneumoconiosis. The pulmonary fibrosis may be pulmonary fibrosis secondary to adult respiratory distress syndrome, drug-induced pulmonary fibrosis, idiopathic pulmonary fibrosis, or hypersensitivity pneumonitis. The pneumoconiosis may be asbestosis, siliconosis, or Farmer's lung. The fibrosis may be a fibrotic disease of the liver or lung. The fibrotic disease of the lung may be caused by rheumatoid arthritis or scleroderma. The fibrotic disease of the liver may be selected from the group consisting of: Hepatitis-C; Hepatitis-B; cirrhosis; cirrhosis of the liver secondary to a toxic insult; cirrhosis of the liver secondary to drugs; cirrhosis of the liver secondary to a viral infection; and cirrhosis of the liver secondary to an autoimmune disease. The toxic insult may be alcohol consumption. The viral infection may be Hepatitis B, Hepatitis C, or hepatitis non-B non-C. The autoimmune disease may be primary biliary cirrhosis, or Lupoid hepatitis. The condition may be dependent on CD40 ligand-induced activation of endothelial cells. The condition may be selected from the group consisting of atherosclerosis, reperfusion injury, allograft rejection, organ rejection, and chronic inflammatory autoimmune diseases.

The atherosclerosis may be accelerated atherosclerosis associated with organ transplantation.

The chronic inflammatory autoimmune disease may be vasculitis, rheumatoid arthritis, scleroderma, or multiple sclerosis.

The condition may be dependent on CD40 ligand-induced activation of epithelial cells.

In one embodiment of the invention, the epithelial cells are keratinocytes, and the condition is psoriasis.

The condition may be an inflammatory kidney disease. The inflammatory kidney disease may not be initiated by autoantibody deposition in kidney. The kidney disease may be selected from the group consisting of: membranous glomerulonephritis; minimal change disease/acute tubular necrosis; pauci-immune glomerulonephritis; focal segmental glomerulosclerosis; interstitial nephritis; antitissue antibody-induced glomerular injury; circulating immune-complex disease; a glomerulopathy associated with a multisystem disease; and drug-induced glomerular disease.

The antitissue antibody-induced glomerular injury may be anti-basement membrane antibody disease.

The present invention provides for an isolated nucleic acid molecule encoding a TRAF-3 deletion isoform peptide. The nucleic acid molecule may be DNA, RNA, cDNA, recombinant DNA, or mRNA.

One embodiment of the invention is a vector comprising the TRAF-3 deletion isoform nucleic acid molecule or variants or isoforms thereof operably linked to a transcriptional control sequence recognized by a host cell transformed with the vector. The vector may be a plasmid.

The present invention provides for a method of providing a subject with an immunosuppressant effective amount of an abnormal CD40 receptor-associated factor, comprising: introducing into CD40-bearing cells of the subject, a nucleic acid sequence encoding an abnormal CD40 receptor-associated factor polypeptide, under conditions such that the cells express in the subject an immunosuppressant effective amount of the abnormal CD40 receptor-associated factor.

In embodiments of the methods described herein, the CD40-bearing cells are selected from the group consisting of B cells, fibroblasts, endothelial cells, epithelial cells, T cells, basophils, macrophages, Reed-Steinberg cells, dendritic cells, myeloma cells, renal cells, and smooth muscle cells.

In a more specific embodiment the B cells are resting B cells, primed B cells, myeloma cells, lymphocytic leukemia B cells, or B lymphoma cells. In another specific embodiment the epithelial cells are keratinocytes. In another embodiment the fibroblasts are synovial membrane fibroblasts, dermal fibroblasts, pulmonary fibroblasts, or liver fibroblasts. In another specific embodiment the renal cells are selected from the group consisting of glomerular endothelial cells, mesangial cells, distal tubule cells, proximal tubule cells, parietal epithelial cells (e.g., crescent parietal epithelial cells), visceral epithelial cells, cells of a Henle limb, and interstitial inflammatory cells. In another embodiment the smooth muscle cells are smooth muscle cells of the bladder, vascular smooth muscle cells, aortic smooth muscle cells, coronary smooth muscle cells, pulmonary smooth muscle cells, or gastrointestinal smooth muscle cells. In a more specific embodiment the gastrointestinal smooth muscle cells are esophageal smooth muscle cells, stomachic smooth muscle cells, smooth muscle cells of the small intestine, or smooth muscle cells of the large intestine.

In an embodiment of this invention the introducing of the nucleic acid into cells of the subject comprises: a) treating cells of the subject ex vivo to insert the nucleic acid sequence into the cells; and b) introducing the cells from step a) into the subject.

The subject which can be treated by the methods described herein is an animal. Preferably the animal is a mammal Subjects specifically intended for treatment with the method of the invention include humans, as well as nonhuman primates, sheep, horses, cattle, goats, pigs, dogs, cats, rabbits, guinea pigs, hamsters, gerbils, rats and mice, as well as the organs, tumors, and cells derived or originating from these hosts.

In an embodiment the condition is organ rejection in a subject receiving transplant organs. Examples of suitable transplant organs include a kidney, heart or liver, as well as others known to those of skill in the art. In another embodiment the condition is an immune response in a subject receiving gene therapy. One difficulty encountered in gene therapy is an immune response by the patient to the gene therapy vector and the proteins it expresses (Yang, Y. et al. (1996) J. Virol. 70:6370). Because the protein of this invention inhibits the immune response, gene therapy with the protein of this invention does not trigger an immune response. Its immunosuppressant effect also makes it useful as an adjunct to other forms of gene therapy. For example, at the same time that a vector being administered to provide a gene therapy patient with a desired gene product, the patient is also administered a vector which provides the protein of this invention.

In an embodiment of this invention the immune response is autoimmune manifestations of an infectious disease. In more specific embodiments the autoimmune manifestations are derived from Reiter's syndrome, spondyloarthritis, Lyme disease, HIV infections, syphilis or tuberculosis.

This invention provides a nucleic acid molecule encoding the protein of this invention. The nucleic acid may be DNA (including cDNA) or RNA. It may be single or double stranded, linear or circular. It may be in the form of a vector, such as a plasmid or viral vector, which comprises the nucleic acid molecule operably linked to a transcriptional control sequence recognized by a host cell transformed with the vector. In one embodiment the DNA molecule comprises the coding strand of the TRAF-3 deletion isoform Δ130 or Δ221 clone (nucleotide sequence shown in FIGS. 15 and 17, respectfully). In another embodiment the DNA molecule is complementary to the coding strand of the TRAF-3 clone of FIGS. 15 or 17.

This invention also provides a method of providing a subject with an immunosuppressant effective amount of an abnormal CD40 receptor-associated factor, comprising: introducing into CD40-bearing cells of the subject, a nucleic acid sequence encoding an abnormal TRAF-3 deletion isoform polypeptide, under conditions such that the cells express in the subject an immunosuppressant effective amount of the abnormal CD40 receptor-associated factor.

Gene therapy for providing a subject with a protein encoded by a gene are described in U.S. Pat. No. 5,399,346, issued Mar. 21, 1995 (Anderson, et al.). A nucleic acid sequence encoding the protein of interest can be inserted into cells of the subject in vivo. Alternatively the nucleic acid can be inserted into cells ex vivo and the transfected cells can then be introduced into the subject. Accordingly, in an embodiment the introducing of the nucleic acid into cells of the subject comprises: a) treating cells of the subject ex vivo to insert the nucleic acid sequence into the cells; and b)introducing the cells from step a) into the subject.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

EXAMPLE 1

TRAF-3 mRNA Splice-deletion Variants Encode Isoforms that Induce NF-κB Activation

[Abbreviations used: TRAF, TNF receptor-associated factor; TNF-R,Tumor Necrosis Factor Receptor; Zn finger, zinc finger; ORF, open reading frame; aa, amino acid; Iscove's Modified Dulbecco Medium, IMDM.]

Although TRAF-3 gene products are required for signaling in T-B cell collaboration, full-length TRAF-3 appears to lack signaling function in transient transfection assays that measure NF-κB activation. However, the TRAF-3 gene also encodes at least 3 mRNA splice-deletion variants that predict protein isoforms (Δ25aa, Δ52aa and Δ56aa) with altered zinc (Zn) finger domains and unknown functional capacities. To determine whether TRAF-3 splice-deletion variants may transmit activating receptor signals to the nucleus, cDNAs for 5 additional splice-variant isoforms (Δ27aa, Δ83aa, Δ103aa, Δ130aa and Δ221aa) were cloned from a TRAF-3$^+$ lymphoma and the expression and function of each of the 8 TRAF-3 splice-deletion variants was analyzed. Among the splice-deletion variants, TRAF-3 Δ130 mRNA is expressed by tonsilar B cells and by each of a panel of B and T cell lines. TRAF-3 Δ221 protein is expressed by tonsilar B cells and by each of the lymphocytic lines. The functional effect of over-expressing each TRAF-3 splice-deletion variant on NF-κB activation was studied in 293T cells. Seven of the TRAF-3 splice-deletion variants, such as TRAF-3 Δ130, induce substantial NF-κB-driven luciferase activity (80–500 fold). In contrast, TRAF-3 Δ221 (in which the complete Zn finger domain is absent) fails to induce NF-κB activation. Although full-length TRAF-3 alone is inactive, it augments the functional effects of the 7 activating TRAF-3 splice-deletion variants (1.4–5 fold). These data indicate that

1. Introduction

TRAF-3 gene products are signaling molecules that interact with the cytoplasmic tails of CD40 (Cheng et al., 1995; Hu et al., 1994; Sato et al., 1995), other Tumor Necrosis Factor-Receptor (TNF-R) family members (e.g. LTβ-R, CD30, CD27, Ox40) (Mosialos et al., 1995; Gedrich et al., 1996; Boucher et al., 1997; Yamamoto et al., 1998; Vanarsdale et al., 1997; Arch and Thompson, 1998; Kawamata et al., 1998) and the Epstein-Barr virus latent membrane protein, LMP1 (Mosialos et al., 1995). The finding that TRAF-3$^{(-/-)}$ lymphocytes are specifically defective in T-B lymphocyte collaboration, indicates that TRAF-3 gene products are required for signaling events that underlie this function (Xu et al., 1996). Full-length TRAF-3 alone is unlikely to account for such signaling, since over-expression of full-length TRAF-3 fails to induce NF-κB activation (Rothe et al., 1995; Takeuchi et al., 1996; Dadgostar and Cheng, 1998). However, alternative splicing of TRAF-3 transcripts generates mRNA species that encode at least 3 putative isoforms with altered Zn finger domains that may participate in transmitting receptor signals to the nucleus (Sato et al., 1995; Krajewski et al., 1997; van Eyndhoven et al., 1998). Therefore, the present study addressed whether TRAF-3 mRNA splice-deletion variants encode TRAF-3 protein isoforms that are able to induce NF-κB activation.

TRAF-3 is a member of the TRAF (TNF Receptor-associated factor) family of proteins, of which six have been identified (TRAF-1 through 6) (Rothe et al., 1994; Regnier et al., 1995; Ishida et al., 1996; Ishida et al., 1996; Kashiwada et al., 1998; Cheng et al., 1995; Hu et al., 1994; Sato et al., 1995; Mosialos et al., 1995). TRAF-3, like other TRAFs, appears to lack intrinsic catalytic activity, which suggests that TRAF-3 functions as a docking or adaptor molecule for other proteins that mediate signaling events. TRAF family members are related by significant homology in their carboxy-terminal TRAF-C domains (Rothe et al., 1994; Cheng et al., 1995). The TRAF-3 TRAF-C domain is known to be important for the interaction of TRAF-3 with the cytoplasmic tails of TNF-R family receptors (Cheng et al., 1995; Force et al., 1997; Vanarsdale et al., 1997), homo-oligomerization (Cheng et al., 1995; Force et al., 1997; Sato et al., 1995; Pullen et al., 1998) and binding to cytoplasmic proteins such as I-TRAF/TANK (Rothe et al., 1996; Cheng and Baltimore, 1996) and NIK (Song et al., 1997; Malinin et al., 1997). In addition to the TRAF-C domain, TRAF-3 contains an amino-terminal RING finger domain, five atypical Zn finger motifs, an iso-leucine zipper domain and a TRAF-N domain (Cheng et al., 1995; Hu et al., 1994; Sato et al., 1995; Mosialos et al., 1995). In TRAF-2 and TRAF-5, the RING finger and Zn finger domains have been shown to play important roles in mediating NF-κB activation (Takeuchi et al., 1996; Dadgostar and Cheng, 1998). The functional potentials of the TRAF-3 RING finger and Zn finger domains remain enigmatic, since TRAF-3 itself fails to induce NF-κB activation (Rothe et al., 1995; Takeuchi et al., 1996; Dadgostar and Cheng, 1998). However, the TRAF-3 RING finger domain is capable of supporting NF-κB activation in chimeric TRAF-3/5 molecules (Dadgostar and Cheng, 1998).

Alteration of the TRAF-3 Zn finger domain by alternative mRNA splicing was suggested by analysis of the sequences of the initial TRAF-3 cDNA clones isolated. One TRAF-3 cDNA clone (CAP1) contains a 75 bp deletion, relative to 3 other TRAF-3 cDNA clones (termed CRAF1, CD40bp and LAP1) (Cheng et al., 1995; Hu et al., 1994; Sato et al., 1995; Mosialos et al., 1995). In addition, 2 other TRAF-3 mRNA variants containing 156 bp and 168 bp deletions were recently identified (van Eyndhoven et al., 1998). Each of the 3 mRNA species with deleted elements, encodes a putative TRAF-3 protein isoform with an altered number and composition of the Zn fingers. These putative isoforms have been termed, TRAF-3b (Δ25aa), TRAF-3c (Δ52aa) and TRAF-3d (Δ56aa) (Krajewski et al., 1997; van Eyndhoven et al., 1998). Characterization of the human TRAF-3 genomic structure indicated that these 3 TRAF-3 mRNA species result from alternative mRNA splicing (van Eyndhoven et al., 1998). Further analysis of the TRAF-3 gene suggested that a large number of additional splice variants may be generated, since each of the splice junctions of exons 4 through 10 are class "0". Therefore, splice-deletion variants involving any or all of exons 5–10 would maintain open reading frames (ORFs) (van Eyndhoven et al., 1998). However, additional splice-deletion variants have not been characterized and the functions of the identified or predicted splice-deletion variants have not been studied.

In the present study, 5 additional cDNA clones were identified that predict novel TRAF-3 protein isoforms with alterations in the Zn finger domains (Δ27 aa, Δ83 aa, Δ103 aa, Δ130 aa and Δ221 aa). To determine whether the splice-deletion variants are expressed at either the mRNA or protein level, RT-PCR and Western Blotting analysis of a panel of B and T cell lines and tonsilar B cells was performed. TRAF-3 Δ130 mRNA is expressed by tonsilar B cells and by each of the lymphocytic cell lines and TRAF-3 Δ130 protein is expressed by two lymphocytic cell lines, D1.1 and BA. TRAF-3 Δ221 protein is expressed by tonsilar B cells and by each of the lymphocytic lines. To study the effects of the TRAF-3 protein splice-deletion variants on the activation of NF-κB, each of the cDNAs encoding the 8 TRAF-3 splice-deletion variants was over-expressed in 293T cells and their effects on an NF-κB driven Luciferase reporter assay were studied. Over-expression of TRAF-3 Δ221 (in which the complete Zn finger domain is absent) fails to activate NF-κB, similar to full-length TRAF-3. However, over-expression of each of the 7 other TRAF-3 splice-deletion isoforms strongly activates NF-κB. In addition, co-expression of full-length TRAF-3 augments the activity of the NF-κB-inducing TRAF-3 splice-deletion variants 1.4 to 5 fold. Taken together, these data indicate that several TRAF-3 splice-deletion variants induce NF-κB activation, and that full-length TRAF-3 can augment their signaling.

2. Materials and Methods

2.1. Isolation and Characterization of TRAF-3 cDNA Clones

Poly (A)$^+$ RNA was isolated from the D1.1 Jurkat T cell line using the Fast Track System (Invitrogen®, San Diego, Calif.). The Reverse Transcription (RT) reaction was performed with an oligo(dT) primer (5'-GGCCACGCGTCGACTAGTAC(T)$_{17}$-3') (SEQ ID NO.: 1) on 0.5 μg mRNA using SuperScript II Reverse transcriptase (Life Technologies, Gaithersburg, Md.) at 50° C., followed by treatment with 1U of RNase H (Boehringer Mannheim®, Indianapolis, Ind.) for 30 min at 37° C. and subsequently purified with the GlassMAX® DNA Isolation Spin Cartridge System (Life Technologies). The Polymerase Chain Reaction (PCR) was performed with forward primer ZnRING.for (5'-GCGGAATTCGGTACC-ACCGTGGAGGACAAG TACAAGTG-3') (SEQ ID NO.: 2) and reverse primer Coiled.rev (5'-CGCGGATCCAAGCTTCTAGTTCTGCCGGAAGG-GCCGGATC-3') (SEQ ID NO.: 3) using the Expand High Fidelity PCR System (Boehringer Mannheim). PCR conditions were 3 min at 95° C. (1 cycle); 30 sec at 95° C., 30 sec at 59° C., 1 min at 72° C. (35 cycles); 7 min at 72° C. (1 cycle). PCR products were separated on 0.6% agarose gels, followed by gel-isolation using the QIAquick® Gel Extraction System (Qiagen, Valencia Calif.) and cloning into the pCR2.1 vector (TA Cloning System®, Invitrogen). Individual cDNA clones were sequenced on a automated ABI 373 DNA sequencer available through the DNA sequencing core facility at Columbia University. These cDNA clones were digested with appropriate restriction enzymes and ligated into the TRAF-3 (CRAF-1) cDNA clone IIIb/pCEP4, the sequence of which is deposited in GenBank under accession number: U21092 (Cheng et al., 1995).

2.2. Isolation of Tonsilar B Cells

Freshly isolated tonsil specimens were cut into 3–10 mm fragments and mashed through a metal sieve in a culture dish containing approximately 10 ml of Iscove's Modified Dulbecco Medium (IMDM) containing 10% fetal calf serum (FCS). The cell mixture was centrifuged at 2000×g for 15 min at room temperature on ficoll (Histopaque-1077, Sigma Diagnostics, St. Louis, Mo.) after which the buffy coat was isolated and washed 4 times with Minimal Essential Media (MEM) containing 5% FCS. The B cell population was enriched by depletion of T cells by resetting with sheep red blood cells (SRBCs) (Colarado Serum Company, Denver, Colo.). SRBCs were washed 3 times with PBS and allowed to interact with $2 \times 10^7$ tonsilar cells for 10 min at 37° C. before the mixture was centrifuged at 150×g for 5 min at room temperature. After resetting for approximately 15 hrs at 4° C., the cells were resuspended and centrifuged on ficoll (Histopaque-1077®, Sigma), followed by isolation of the non-resetting population. The tonsilar B cells were analyzed by FACS and subsequently prepared for poly (A)$^+$ RNA or protein isolation as described below.

2.3. Expression of Alternatively Spliced TRAF-3 mRNA Species

Poly (A)$^+$ RNA was isolated from tonsilar B cells and several B-cell lines (Ramos 2G6, Daudi, Raji, BA) and T-cell lines (D1.1, B2.7, H9, CEM) using the Fast Track® System (Invitrogen). RT was performed with the TRAF-3 specific primer 3Bend-2(749).R (5'-TTGAAACAAAATTGCACTCTTGAA-3') (SEQ ID NO.: 4). RT and PCR were performed as described above. PCR reactions were separated on 1.5% agarose gels, blotted onto Hybond-N® membranes (Amersham Life Science, Cleveland, Ohio), UV-crosslinked using a Stratalinker® (Stratagene, La Jolla, Calif.) and hybridized to [$\gamma$-$^{32}$P]ATP end-labeled oligonucleotide FF7GEN (5'-AAATGTACAGCGTGTCA AGAGAGCATCG-3') (SEQ ID NO.: 5). Blots were incubated for 1.5 h at 42° C. in pre-hybridization solution (50% formamide, 5×SSCPE, 5×Denhart's solution, 1 mg/ml salmon sperm DNA and 0.1% SDS), followed by incubation for 15 h at 42° C. in hybridization solution (50% formamide, 5×SSCPE, 5×Denhart's solution, 100 µg/ml salmon sperm DNA and 10% Dextran Sulfate) containing the radiolabeled probe. The blots were washed twice for 15–20 min at 68° C. in 2×SSC, 1% SDS and the hybridization patterns were visualized by autoradiography (BioMax MS® film, Eastman Kodak, Rochester, N.Y.).

2.4. Expression Constructs

In addition to the TRAF-3 cDNA isoforms, full-length human TRAF-2 cDNA was cloned by RT-PCR from Jurkat D1.1 mRNA. A plasmid containing human CD40 cDNA was used. Full-length TRAF-3, all TRAF-3 cDNA splice-deletion variants, TRAF-2 and CD40 were cloned into the expression vector pCEP4 (Invitrogen). The pRDIIx4LUC Firefly Luciferase reporter construct was generated by digestion of pRDIIx4CAT (Tran et al., 1997) after which the fragment representing the minimal Interferon-β promoter containing 4 upstream NF-κB sites was cloned 5' to the Luciferase gene in the pGL3-Enhancer® Luciferase reporter vector (Promega, Madison, Wis.). The pRL-TK Renilla Luciferase control reporter vector was obtained from Promega.

2.5. Luciferase Assay

Using the Mammalian Cell Transfection System (Specialty Media, Lavallette, N.J.), which allows transfection of mammalian cells by standard calcium phosphate precipitation, $0.5 \times 10^6$ 293T cells/60 mm plate were transfected with 0.3 µg of pRDIIx4LUC and 0.3 µg pRL-TK reporter constructs and either 3 µg pCEP4/TRAF-3 (full-length or isoforms), 3 µg pCEP4/TRAF-2 or 0.5 µg pCEP4/CD40 expression constructs. In all experiments the amount of DNA transfected was equalized by addition of empty pCEP4 expression vector. After transfection, the cells were cultured for approximately 40 h before harvesting. The NF-κB dependent Luciferase reporter assay was performed utilizing the Dual-Luciferase Reporter Assay System (Promega). Luciferase activity was measured using a Monolight 2010 luminometer (Analytical Luminescence Laboratory, Sparks, Md.). The amount of Renilla Luciferase served as an internal control for normalization of the experimental Firefly Luciferase activities. The results shown are representative of three independent experiments.

2.6. Western Blot Analysis

For Western blot analysis, $1.5 \times 10^6$ 293T cells were transfected with 3 µg of TRAF-3 (full-length and/or isoforms) as described above. After 40 h cells were washed in ice-cold PBS and then lysed for 30 min at 4° C. in 250 µl of RIPA lysis buffer (containing 50 mM Tris, pH 8.0, 150 mM Sodium Chloride, 0.1 mM Sodium Orthovanadate, 50 mM Sodium Fluoride, 1% Nonidet P-40, 0.5% Deoxycholate, 0.1% SDS, 1 mM PMSF, 1 µg/ml Aprotinin, 1 µg/ml Leupeptin, 1 µg/ml Pepstatin). Subsequently, the samples were centrifuged at 14,000×g for 15 min at 4° C. to remove cellular debris. Protein concentration was determined using the Bio-Rad Detergent Compatible Protein Assay (Bio-Rad Laboratories, Hercules, Calif.). For Western blot analysis of endogenous TRAF-3 (full-length or isoforms) in tonsilar B cells or in the B-cell and T-cell lines, approximately $20 \times 10^6$ cells were washed in ice-cold PBS and then lysed for 30 min at 4° C. in 500 µl of RIPA lysis buffer. Protein samples were boiled in reducing sample buffer for 5 min, separated by SDS-PAGE (10% gel), transferred onto Immobilon-P® membranes (Millipore, Bedford, Mass.) using the Bio-Rad Transblot® System (Bio-Rad) and detected with rabbit polyclonal anti-TRAF-3 H-20 antiserum (Santa Cruz Biotechnology, Santa Cruz, Calif.) as the primary antibody (directed at amino acids 8–27 at the amino-terminus of TRAF-3) and anti-rabbit IgG conjugated to horse-radish peroxidase (Boehringer Mannheim, Indianapolis, Ind.) as the secondary antibody. Proteins were visualized using BM Chemiluminescence Blotting Substrate (Boehringer) and Fuji Medical X-ray film (Fuji Medical Systems U.S.A., Stamford, Conn.).

3. Results

3.1. Alternative Splicing Results in Distinct TRAF-3 mRNA Species that Predict TRAF-3 Protein Isoforms To identify TRAF-3 mRNA splice variants, RT-PCR was performed using TRAF-3 specific primers (derived from nucleotide sequences in exons 3 and 11) on mRNA from the TRAF-3+ Jurkat D1.1 T cell line (van Eyndhoven et al., 1998). Several amplified bands were found to be TRAF-3 specific by Southern blotting using a TRAF-3 specific oligonucleotide probe. The PCR products were cloned and sequenced and found to represent 8 distinct TRAF-3 mRNA species containing deletions that correspond to precise excisions of exon-encoded segments by alternative splicing: Δ75 bp (Δexon 8; TRAF-3b), Δ81 bp (Δexon 7), Δ156 bp (Δexon 7+8; TRAF-3c), Δ168 bp (Δexon 8+9; TRAF-3d), Δ249 bp (Δexon 7–9), Δ309 bp (Δexon 8–10), Δ390 bp (Δexon 7–10) and Δ663 bp (Δexon 5–10) (FIG. 1). In all cDNA clones isolated, ORFs are maintained and therefore predict TRAF-3 protein isoforms with amino acid deletions; Δ25aa, Δ27aa, Δ52aa, Δ56aa, Δ83aa, Δ103aa, Δ130aa and Δ221aa, respectively (FIG. 1). The Zn finger domain is altered in all of the splice-variant isoforms, except TRAF-3 Δ221 in which it is completely absent (FIG. 1). An N-terminal portion of the predicted iso-leucine Zipper domain is deleted in TRAF-3 Δ103, Δ130 and Δ221, and in addition, a C-terminal portion (~8aa) of the RING finger domain is deleted in TRAF-3 Δ221 (FIG. 1). These data suggest that at least 8 TRAF-3 mRNA splice-deletion variants are expressed by the D1.1 cell line that encode putative TRAF-3 protein isoforms, containing distinct alterations in the Zn finger domain.

Figure 2:
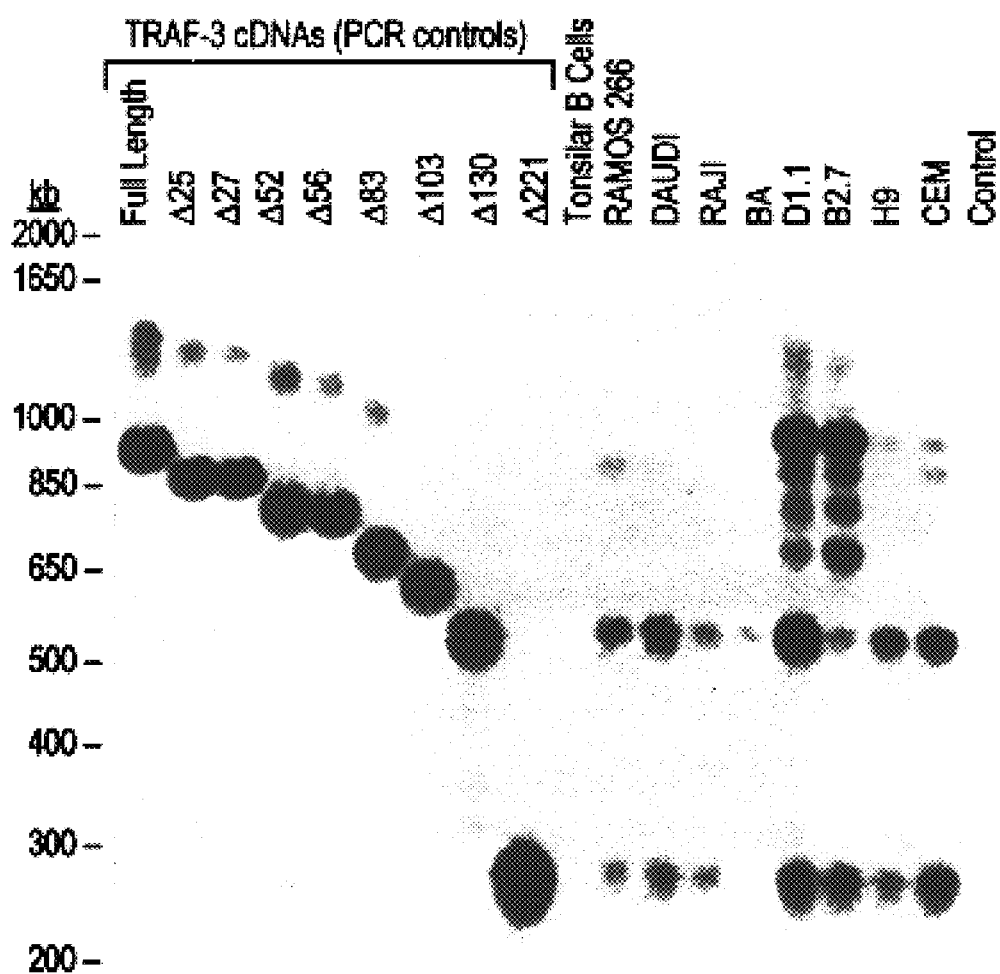
FIG. 2: Expression of alternatively spliced TRAF-3 mRNA species in lymphoid cells. TRAF-3 specific RT-PCR was performed on poly (A)$^+$ RNA from tonsilar B cells, and a panel of B cell (Ramos 2G6, Daudi, Raji and BA) and T cell tumor lines (D1.1, B2.7, H9 and CEM). PCR products were separated by gel electrophoresis and transferred onto membranes for Southern blot analysis using a TRAF-3 specific probe (FF7GEN). On the left are shown PCR products generated using cloned TRAF-3 cDNAs (full-length and isoforms) as templates, as indicated. On the right are shown the relative levels of expression of TRAF-3 mRNA species in the tonsilar B cells and in each of the B and T cell lines, as indicated.

3.2. Expression of Alternatively Spliced TRAF-3 mRNA Species in Lymphoid Cells To determine the relative levels of full-length TRAF-3 and the 8 TRAF-3 mRNA splice-deletion species cloned from Jurkat D1.1 mRNA, RT-PCR was performed on mRNA from Jurkat D1.1, using the same PCR primer pair (described above) and analyzed by Southern blotting using the same TRAF-3 specific probe (described above). As controls, cloned cDNAs representing the 9 TRAF-3 mRNA species were used as templates in parallel PCR reactions. Jurkat D1.1 cells express high levels of full-length TRAF-3 and Δ130 mRNAs and moderate levels of TRAF-3 Δ83 and Δ221 mRNAs (FIG. 2). This analysis did not discriminate between the PCR products from TRAF-3 Δ25 and Δ27 or between TRAF-3 Δ52 and Δ56 and therefore these amplification products are referred to as "Δ25/Δ27" and "Δ52/Δ56", respectively. Jurkat D1.1 express moderate levels of both the Δ25/Δ27 and Δ52/Δ56 mRNA species (FIG. 2). Surprisingly, Jurkat D1.1 does not express detectable TRAF-3 Δ103 mRNA (FIG. 2), despite the fact that a cDNA encoding TRAF-3 Δ103 was cloned from D1.1 mRNA. Therefore, these data are consistent with the interpretation that the 9 cloned TRAF-3 cDNAs (8 splice-deletion variants plus full-length) are representative of the major TRAF-3 mRNA species in D1.1, expect for TRAF-3 Δ103 which is evidently a relatively rare transcript in D1.1.

The analysis of the relative expression of TRAF-3 mRNA species was extended to examine mRNA from a panel of human B cell (Ramos 2G6, Daudi, Raji and BA) and T cell (B2.7, H9 and CEM) tumor lines. Jurkat B2.7 cells are similar to D1.1 in their pattern of expressing TRAF-3 mRNA species, except that B2.7 cells have a lower level of TRAF-3 Δ130 (FIG. 2). In each of the other lymphocytic cell lines studied, TRAF-3 Δ130 mRNA was the predominant product and serves as a reference for the relative expression of the other TRAF-3 mRNA species (FIG. 2). Relative to their expression of TRAF-3 Δ130 mRNA, substantially less of the longer TRAF-3 mRNA species are expressed (FIG. 2). The T cell lines, H9 and CEM, express full-length TRAF-3, which is barely detectable in the other cell lines (except Jurkat D1.1 and B2.7) (FIG. 2). TRAF-3 Δ221 is expressed by each of the cell lines, except the EBV transformed B cell BA (FIG. 2). The Δ25/Δ27 band is amplified in the B cell lines Ramos and Daudi and the T cell line CEM (FIG. 2). Together, these data indicate that TRAF-3 splice-deletion mRNAs are expressed in a variety of B and T cell tumor lines.

The analysis of the relative expression of TRAF-3 mRNA species was also extended to examine mRNA from human tonsilar B cells. Similar to the tumor cell lines, tonsilar B cells express TRAF-3 Δ130 mRNA (FIG. 2). Tonsilar B cells express barely detectable full-length TRAF-3 mRNA (only evident at longer exposures). Tonsilar B cells do not express detectable mRNA for TRAF-3 Δ221, which is similar to the EBV transformed B cell line BA, but different from the other tumor cell lines in which TRAF-3 Δ221 mRNA is relatively prominent (FIG. 2). Together, these data show that tonsilar B cells express the TRAF-3 splice-deletion mRNA species TRAF-3 Δ130, similar to several B and T cell tumor lines.

3.3. Expression of TRAF-3 Protein Isoforms in Lymphoid Cells

Figure 3:
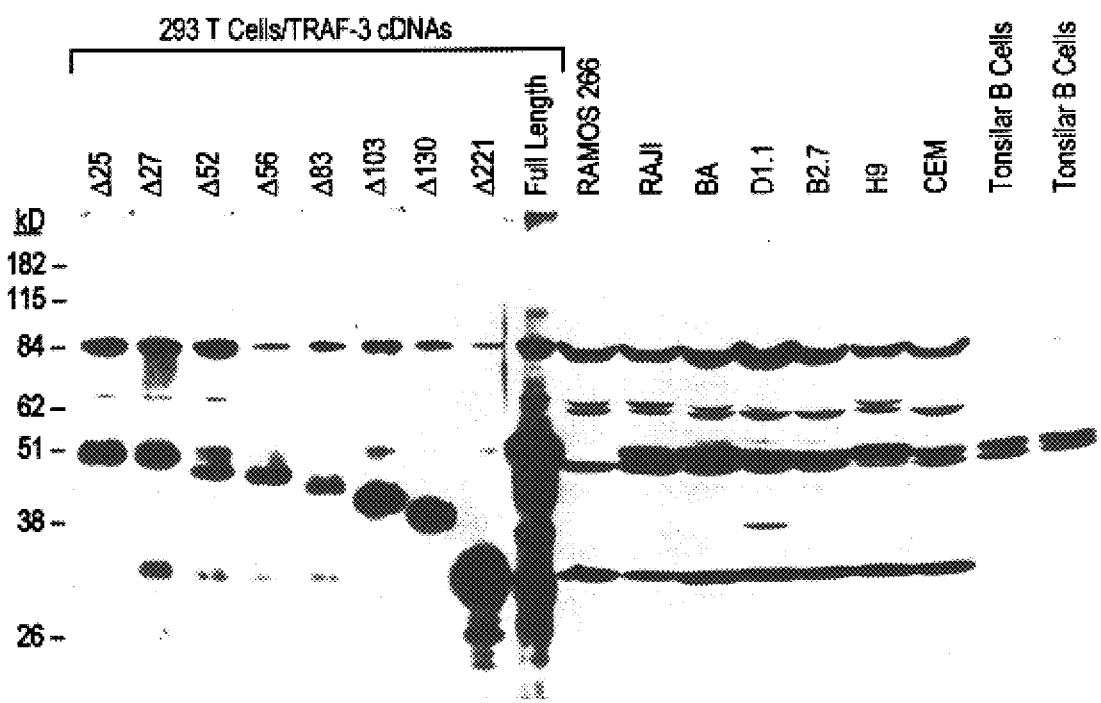
FIG. 3: Expression of TRAF-3 protein isoforms in lymphoid cells. Cell lysates from tonsilar B cells, a panel of B cell (Ramos 2G6, Raji, BA and EJAB) and T cell tumors (D1.1, B2.7, H9, CEM) (50 μg of total protein) or transiently transfected 293T cells (15 μg of total protein) were separated by SDS-PAGE, transferred to a PVDF membrane and subjected to immunoblotting using anti-TRAF-3 (N-terminus) polyclonal antiserum (H-20). On the left are shown the overexpressed TRAF-3 protein isoforms in 293T cells as positive controls and on the right are shown the expression patterns of anti-TRAF-3 reactive protein species in lymphoid cells. The band migrating at 50 kD is non-specific (marked by an asterisk (*)) as are the bands at 85, 66 and 62 kD.

To determine the expression of TRAF-3 protein isoforms in tonsilar B cells and the panel of B cell and T cell tumor lines, cell lysates were examined by Western blotting using a polyclonal anti-TRAF-3 N-terminus antiserum (H-20) (FIG. 3). As controls, cDNAs encoding full-length TRAF-3 and the 8 splice-deletion variants were over-expressed in 293T cells and cell lysates from these transfected cells were examined in parallel. TRAF-3 protein that migrates as either full-length TRAF-3 or TRAF-3 Δ25/Δ27 is prominently detected as a specific band in all cells, except Ramos (FIG. 3). The absence of full-length TRAF-3 protein in Ramos cells has been previously reported (Krajewski et al., 1997) and is consistent with the undetectable full-length TRAF-3 mRNA in Ramos (FIG. 2). The expression of either full-length TRAF-3 or TRAF-3 Δ25/Δ27 in all of the other cells studied, is surprising given the relatively low expression of TRAF-3 mRNA species that encode either of these isoforms in the majority of these cells (FIG. 2). TRAF-3 protein that migrates as TRAF-3 Δ221 is expressed in all cells, and at low levels in tonsilar B cells (FIG. 3). The expression of TRAF-3 Δ221 is generally consistent with the pattern of mRNA expression, except for BA cells that express TRAF-3 Δ221 protein, but lack detectable mRNA encoding TRAF-3 Δ221. Jurkat D1.1 cells, and to a lesser extent BA cells, express TRAF-3 protein that migrates as TRAF-3 Δ130 (FIG. 3). The lack of detectable TRAF-3 Δ130 protein in most cells examined is surprising, given the relatively high level of TRAF-3 Δ130 mRNA in all of the cells and cell lines examined. However, the expression of TRAF-3 Δ130 protein by D1.1 and not B2.7 Jurkat cells is consistent with the relatively higher TRAF-3 Δ130 mRNA expression by D1.1 (FIG. 2). Together, these data show that the TRAF-3 mRNA splice-deletion isoform TRAF-3 Δ221 is expressed in a variety of cell lines and that TRAF-3 Δ130 is expressed in certain tumors.

Figure 4:
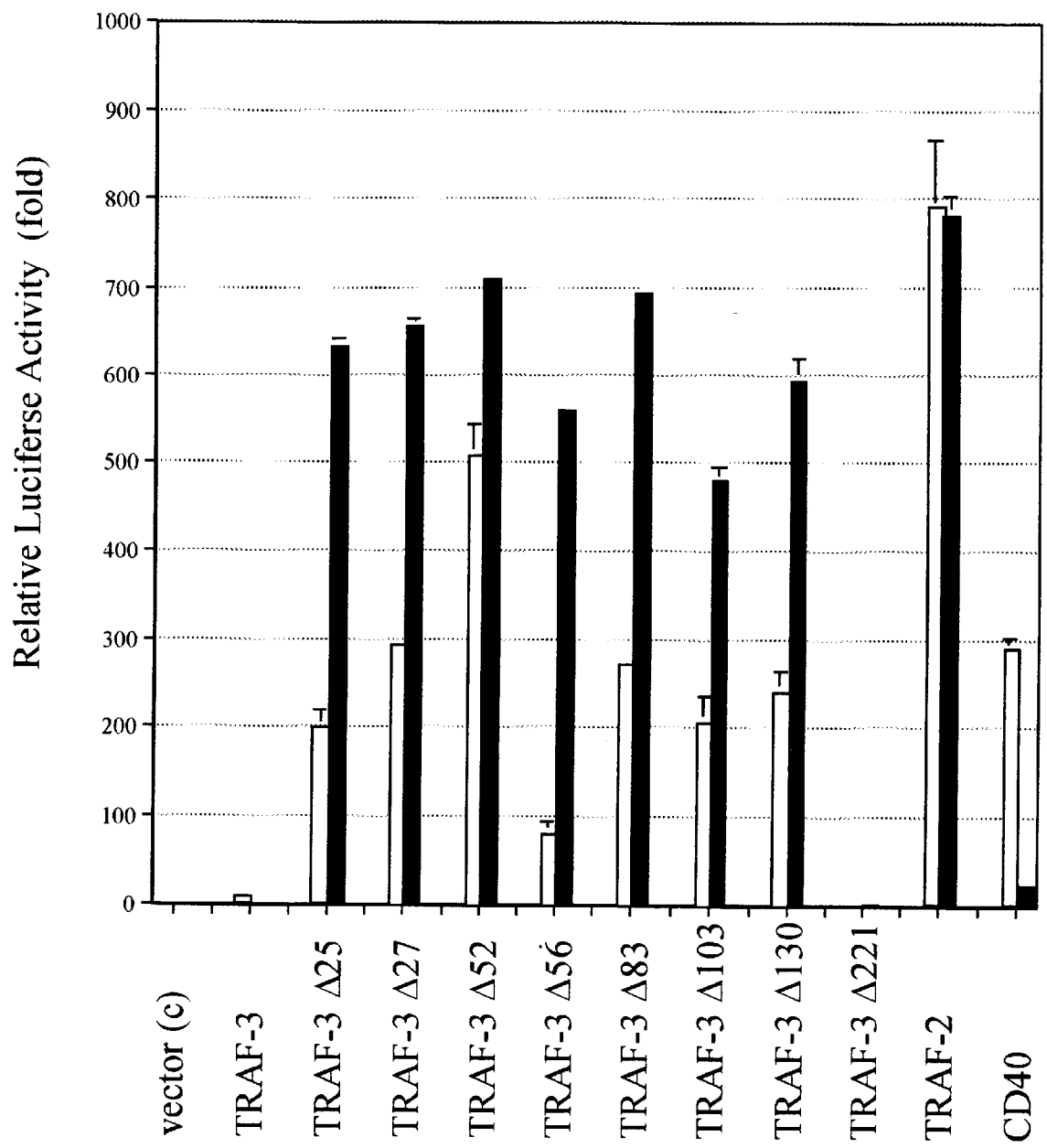
FIG. 4: Effect of over-expressing TRAF-3 splice-deletion variants and/or full-length TRAF-3 on NF-κB activation. 293T cells were transfected with 3 μg of expression vectors encoding TRAF-3 isoforms alone (open bars) or co-transfected with 3 μg of full-length TRAF-3 (black bars). As controls, 3 μg of TRAF-2 or 0.5 μg of CD40 expression vector was transfected alone or with 3 μg of full-length TRAF-3 expression vector. All samples were co-transfected with 0.3 μg of pRDIIx4LUC (Firefly Luciferase) and 0.3 μg of pRL-TK (Renilla Luciferase). The amount of DNA transfected was equalized by the addition of empty pCEP4 vector. Luciferase activity was measured 40 h after transfection. All values were normalized by the individual Renilla Luciferase activity and are shown as the means of duplicate samples with error bars representing standard deviation. Results shown are representative of three independent experiments.

3.4. Effect of Over-expression of TRAF-3 Splice-deletion Variants on NF-κB Activation in 293T Cells To determine whether any of the 8 TRAF-3 splice-deletion variants are able to induce NF-κB activation, their functional effects were studied on the transcription of an NF-κB driven Luciferase reporter construct in transient assays in 293T cells. As positive controls for NF-κB activation, cDNAs encoding CD40 and TRAF-2 were overexpressed and substantial NF-κB activation was observed, as expected (Rothe et al., 1995) (FIG. 4). Over-expression of 7 of the TRAF-3 splice-deletion variants (Δ25 aa, Δ27 aa, Δ52 aa, Δ56 aa, Δ83 aa, Δ103 aa and Δ130 aa) potently activates NF-κB (between 80 to 500 fold). Among the NF-κB-inducing TRAF-3 splice-deletion variants, TRAF-3 Δ52 is relatively more potent (approximately 500 fold activation) and TRAF-3 Δ56 is relatively less potent (approximately 80 fold activation). In contrast, over-expression of TRAF-3 Δ221 fails to activate NF-κB (FIG. 4), which indicates that the NF-κB activating effect of the other cDNAs encoding TRAF-3 splice-deletion variants is specific. These data show that over-expression of certain TRAF-3 splice-deletion variants induces NF-κB activation, but full-length TRAF-3 and TRAF-3 Δ221 lack this effect.

Figure 5:
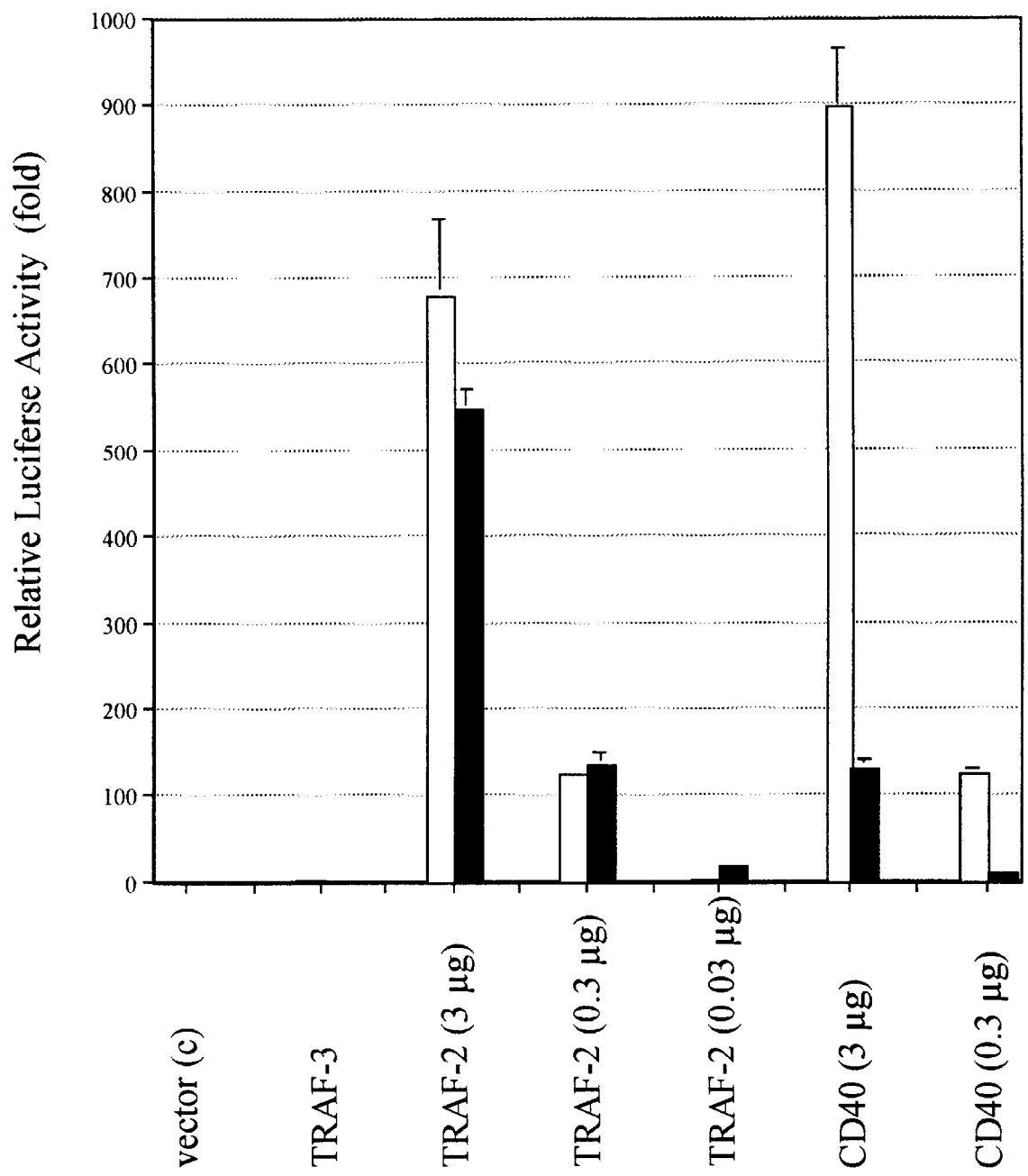
FIG. 5: Effect of full length TRAF-3 on TRAF-2 and CD40 mediated NF-κB activation. 293T cells were transfected with the indicated amounts of TRAF-2 or CD40 with 3 μg of TRAF-3 (full length) and 0.3 μg of pRDIIx4LUC (Firefly luciferase) and 0.3 μg of pRL-TK (Renilla luciferase). The amount of DNA transfected was normalized for by adding empty pCEP4 vector. Cell lysates were prepared after 40 hours and used for determination of Luciferase activity. The open bars represent samples in which the expression vectors (as indicated) are transfected alone, whereas solid bars represent samples in which they are co-transfected with full length TRAF-3. All values were normalized by the individual Renilla luciferase activity and are shown as the means of duplicate samples with +/–S.D.
Figure 6:
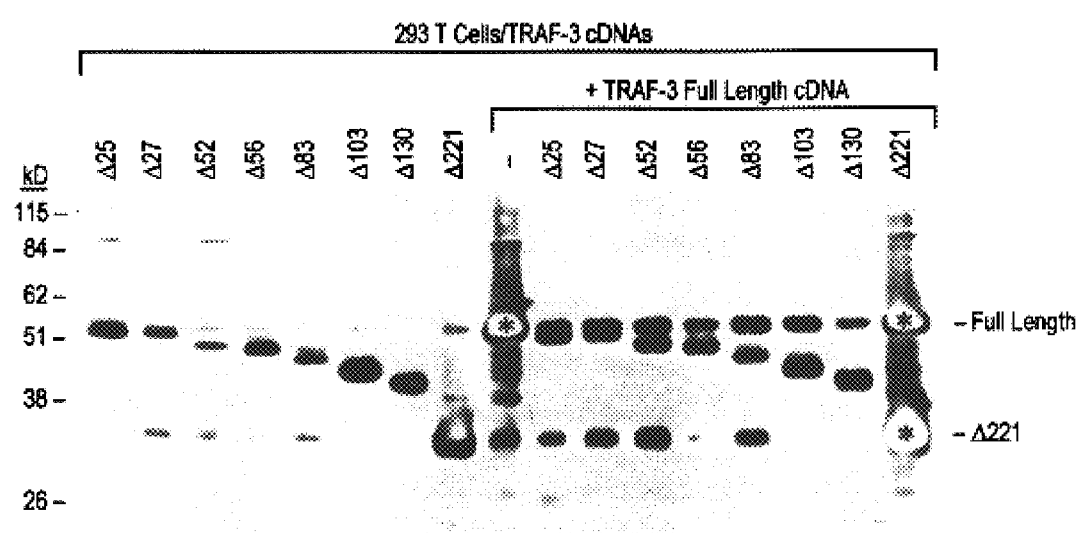
FIG. 6: Expression of co-expressed full length TRAF-3 and TRAF-3 splice-deletion isoforms in transfected 293T cells. 293 T cells were transfected with 3 μg of full length TRAF-3 (full length or isoforms) or co-transfected with 3 μg of full length TRAF-3 and 3 μg of each of the TRAF-3 isoforms. 15 μg of total protein was separated by SDS-PAGE and subjected to immunoblotting using anti-TRAF-3 polyclonal antibody H-20. On the left are shown the cells over-expressing individual TRAF-3 isoforms. On the right are shown the cells over-expressing full length TRAF-3 in addition to TRAF-3 isoforms (as indicated on top). Asterixes indicate areas in which strong chenoluminescence signal resulted in "white-out" of the exposed film.

3.5. Effect of Full-length TRAF-3 on NF-κB Activation Induced by TRAF-3 Splice-deletion Variants Since full-length TRAF-3 has been reported to inhibit NF-κB activation induced by over-expression of CD40 (Rothe et al., 1995), the next series of experiments analyzed the effects of over-expressing full-length TRAF-3 on the NF-κB activation induced by over-expression of TRAF-3 splice-deletion variants. Consistent with previous reports (Rothe et al., 1995), over-expression of full-length TRAF-3 inhibits the NF-κB activation induced by CD40 over-expression (FIG. 5). The TRAF-3 mediated inhibition of CD40-induced NF-κB activation is specific, since over-expression of full-length TRAF-3 has minimal or no effect on NF-κB activation induced by TRAF-2 over-expression in 293T cells (FIG. 4). Co-expression of full-length TRAF-3 with each of the 7 TRAF-3 splice-deletion isoforms that activates NF-κB alone, results in augmentation of their NF-κB activation by 1.4 to 5 fold (FIG. 4). For example, in the case of TRAF-3 Δ130, the augmentation by full-length TRAF-3 is greater than 2 fold (FIG. 4). In contrast, co-expression of full-length TRAF-3 with TRAF-3 Δ221 (which does not activate NF-κB alone) does not confer TRAF-3 Δ221 with an ability to induce NF-κB activation (FIG. 4). Therefore, these data indicate that full-length TRAF-3, which lacks intrinsic signaling ability, augments signaling by the NF-κB-inducing TRAF-3 splice-deletion variants.

4. Discussion

In the present study, full-length TRAF-3 and 8 TRAF-3 splice-deletion mRNA species (Δ25aa, Δ27aa, Δ52aa, Δ56aa, Δ83aa, Δ103aa, Δ130aa, and Δ221aa) were analyzed for their expression in tonsilar B cells and in a panel of B and T cell tumor lines and for their potential to induce NF-κB activation. Consistent with previous studies, full-length TRAF-3 protein is expressed by tonsillar B cells and by each of the B and T cell tumors studied (except Ramos), but lacks the ability to activate NF-κB when over-expressed. Of the splice-deletion species, TRAF-3 Δ130 mRNA is expressed by tonsillar B cells and by each of the B and T cell tumors and was found to have the ability to activate NF-κB when over-expressed in 293T cells. TRAF-3 Δ221 protein is expressed at low levels by tonsilar B cells and at higher levels by each of the B and T cell tumors, but lacks the ability to induce NF-κB activation. Full-length TRAF-3 augments the NF-κB activation induced by over-expression of TRAF-3 Δ130 or the six other activating splice-deletion variants, but does not confer activity to TRAF-3 Δ221. Together, these data indicate that alternative splicing of TRAF-3 results in splice-deletion variants that induce NF-κB activation, and that full-length TRAF-3 has the potential to augment their function.

Alternative splicing of the TRAF-3 mRNA elements that encode the Zn finger domain was previously described by the identification of cDNAs encoding TRAF-3 Δ25aa, Δ52aa and Δ56aa and by the characterization of the genomic structure of TRAF-3 which showed that these mRNA species correspond to specific deletions of exon-encoded segments (Sato et al., 1995; Krajewski et al., 1997; van Eyndhoven et al., 1998). The genomic structure also revealed that exon/intron junctions of exons 4–10 all have type "0" intron junctions, which would allow for the variable presence or absence of mRNA segments encoded by exons 5–10 in mRNA species that maintain ORFs (van Eyndhoven et al., 1998). This finding indicates that it is possible that $2^6$ (or 64) distinct mRNA species that maintain ORFs could be generated by alternative mRNA splicing of exons 5–10. Therefore, the approach taken to studying potential isoforms was to isolate cDNAs from the TRAF-3$^+$ cell line, Jurkat D1.1 and then to determine whether these mRNA species are expressed by other tumor cell lines or by tonsilar B cells. This approach yielded cDNAs encoding five novel TRAF-3 splice-deletion variants (Δ27aa, Δ83aa, Δ103aa, Δ130aa and Δ221) in addition to the three previously described. All of the 8 splice-deletion variants encode putative TRAF-3 isoforms that maintain ORFs with altered Zn finger domains. It should be noted that not all TRAF-3 isoforms were analyzed in these experiments. For example, splice-deletion variants of other exon-encoded elements may exist and one example of such a variant was reported that predicted translation initiation at Methionine 350 (encoded by exon 11), which predicts a peptide containing only the TRAF-N and TRAF-C domains (Mosialos et al., 1995). All of the TRAF-3 splice-deletion variants identified, contain the TRAF-C domain, which is known to be critical for binding to the cytoplasmic tails of CD40 and other TNF-R family receptors (Cheng et al., 1995; Force et al., 1997; Vanarsdale et al., 1997), homo-oligomerization (Cheng et al., 1995; Force et al., 1997; Sato et al., 1995; Pullen et al., 1998) and binding to cytoplasmic proteins such as I-TRAF/TANK (Rothe et al., 1996; Cheng and Baltimore, 1996) and NIK (Song et al., 1997; Malinin et al., 1997).

Analysis of tonsillar B cells and a panel of B and T cell tumor cell lines for mRNA and protein corresponding to the TRAF-3 splice-deletion variants indicates that, in addition to full-length TRAF-3, certain splice-deletion variants are expressed (e.g., TRAF-3 Δ130 and Δ221). However, discrepancies between the amounts of mRNA and corresponding proteins detected, suggest that mRNA and/or protein stability varies between the isoforms. For example, full-length TRAF-3 protein was expressed by all cells (except Ramos), but full-length TRAF-3 mRNA was expressed at low or undetectable levels in the majority of cells studied. These data are consistent with the possibility that full-length TRAF-3 protein is stable and/or that full-length TRAF-3 mRNA is short-lived. The protein and mRNA corresponding to TRAF-3 Δ221 was found to correlate, except for the case of the EBV transformed B cell BA, in which high level protein was detected in the setting of undetectable mRNA. These data are consistent with the possibility that TRAF-3 Δ221 protein is stable and that the corresponding mRNA may be short lived, at least in BA cells. The mRNA encoding TRAF-3 Δ130 was relatively abundant in all cells examined, but the corresponding protein was detected only in Jurkat D1.1 and BA. These data are consistent with the possibility that TRAF-3 Δ130 protein is short lived and/or the corresponding mRNA is stable. Another possibility is that the translation of TRAF-3 Δ130 is regulated. Future studies will address whether the stability of mRNA and protein affect the expression of TRAF-3 splice variants.

The finding that certain TRAF-3 splice-deletion variants have the capacity to induce NF-κB activation suggests a structural basis for this effect. First, comparison of splice-deletion variants that induce NF-κB activation with full-length TRAF-3 that lacks activating capacity, shows that alterations of the Zn finger domain (relative to full-length TRAF-3) are required for inducing NF-κB activation. Second, comparison of splice-deletion variants that activate NF-κB (TRAF-3 Δ25aa, Δ27aa, Δ52aa, Δ56aa, Δ83aa, Δ103aa, and Δ130aa) with the variant that lacks activating capacity (TRAF-3 Δ221) shows the importance of the Zn finger domain in inducing NF-κB activation, because TRAF-3 Δ221 lacks the entire Zn finger domain. However, TRAF-3 Δ221 also lacks approximately 8 aa from the C-terminal portion of the RING finger domain, which may contribute to its inactivity, since portions of the TRAF-3 RING finger domain support NF-κB activation in chimeric TRAF-3/5 molecules (Dadgostar and Cheng, 1998). These data suggest that the TRAF-3 Zn finger domain and perhaps the C-terminal portion of the RING domain are required for inducing NF-κB activation, but indicate that the Zn finger domain must be of a form encoded by certain of the splice-deletion variants. In this regard, the fact that exons 7, 8 and 9 encode portions of distinct fingers, indicates that the fingers encoded by the splice-deletion variants have altered compositions, relative to full-length TRAF-3, which may confer distinct binding specificites to these motifs.

Another TRAF-family member, TRAF-2, has been shown to utilize alternative mRNA splicing to generate a protein isoform with altered function (Brink and Lodish, 1998). In this case, the isoform termed "TRAF-2" that induces NF-κB activation, is a splice-deletion variant of a full-length TRAF-2 (termed "TRAF-2a") that lacks NF-κB activating capacity (Brink and Lodish, 1998). The activating splice-deletion variant (TRAF-2) lacks 21 bp corresponding to a deletion of 7 aa in the C-terminal portion of the RING finger domain (Brink and Lodish, 1998). Therefore, alternative splicing appears to be a mechanism used by both TRAF-2 and TRAF-3 genes to regulate signaling events, since in both cases splice-deletion variants induce NF-κB activation, but full-length forms do not. Future studies will address whether TRAF-3 mRNA splicing is controlled by activation and differentiation.

Changes in mRNA splicing in response to cellular activation and differentiation have been observed in many systems, such as the change from surface to secreted Ig molecules (the IgH gene locus (Alt et al., 1980)). In addition, a TNF-R gene family member, LARD utilizes alternative mRNA splicing to generate at least 11 isoforms. (Screaton et al., 1997). Naive B and T cells predominantly express LARD isoforms with internal deletions, but upon activation by PHA, a shift in the splicing pattern results in a predominant expression of full-length LARD-1 (Yang et al., 1998). It is also of interest that TNF-α mRNA changes its pattern of mRNA splicing after lymphocyte activation (Yang et al., 1998), which suggests that "ligands", "receptors" and signaling molecules, in the TNF-α family, TNF-R family and TRAF-family, respectively, may utilize alternative mRNA splicing to regulate signaling outcomes.

Although over-expression of full-length TRAF-3 alone does not activate NF-κB, co-transfection of full-length TRAF-3 augments the NF-κB activation induced by splice-deletion variants. It is unclear how full-length TRAF-3 mediates this effect, but it interesting to consider the possibility that full-length TRAF-3 may form complexes with splice-deletion isoforms. In this regard, all of the TRAF-3 isoforms contain TRAF-C domains (and at least, the carboxy-terminal portion of the isoleucine zipper). Therefore, based on the structures encoded by the activating splice-deletion variants, they are expected to form complexes with full-length TRAF-3 (Cheng et al., 1995; Force et al., 1997; Pullen et al., 1998). It will be of interest to determine whether such complexes are formed and whether full-length TRAF-3 stabilizes the activating splice-deletion variants, such as TRAF-3 Δ130, for which protein is undetectable in tonsilar B cells, despite relatively abundant mRNA. In the case of TRAF-2, co-transfection of the splice-deletion variant (TRAF-2) increases the stability of the full-length form (TRAF-2a) (Brink and Lodish, 1998). Future studies will address whether full-length TRAF-3 modulates the expression or stability of activating splice-deletion variants.

The finding that certain TRAF-3 splice-variants are expressed by tonsilar B cells and have the capacity to induce NF-κB activation may reconcile previous views of the role of TRAF-3 gene products in T-B cell interactions that depend on CD40 signaling. Two lines of evidence strongly suggest that TRAF-3 gene products play important roles in CD40 signaling. First, over-expression of a truncated form of TRAF-3 (termed C26), which contains only the TRAF-N and TRAF-C domains, inhibits CD40-mediated CD23 upregulation (Cheng et al., 1995). The C26 TRAF-3 fragment binds the CD40 cytoplasmic tail, but C26 lacks the Zn RING and Zn finger domains that are required by other TRAFs for downstream functions, such as activating NF-κB (Cheng et al., 1995; Takeuchi et al., 1996; Dadgostar and Cheng, 1998). Second, reconstitution of lethally irradiated mice with TRAF-3$^{-/-}$ fetal liver cells resulted in mice with a profound, selective defect in T-dependent antibody responses (Xu et al., 1996). Since this phenotype is similar to that observed in CD154 (CD40-L) $^{-/-}$ (Xu et al., 1994; Renshaw et al., 1994) or CD40$^{-/-}$ mice (Kawabe et al., 1994; Castigli et al., 1994), these data suggest that TRAF-3 gene products play important positive roles in CD40 mediated signaling.

However, the inability of full-length TRAF-3 over-expression to activate NF-κB raised questions about whether TRAF-3 participated in transmitting CD40 signals to the nucleus (Rothe et al., 1995). In light of the new finding that TRAF-3 splice-deletion variants are capable of inducing NF-κB activation, it may be appropriate to reconsider the inactivity of full-length TRAF-3 alone in the context that other TRAF-3 gene products may play dominant roles in transmitting activating CD40 signals to the nucleus. First, the C26 fragment is expected to compete with all of the activating TRAF-3 isoforms for CD40 cytoplasmic tail binding and may form dysfunctional oligomers with these isoforms, which would be consistent with its inhibitory effects (Cheng et al., 1995). Second, the targeted disruption of TRAF-3 prevents the expression of any of the NF-κB-inducing TRAF-3 isoforms, which is consistent with the specific defect of TRAF-3$^{-/-}$ lymphocytes in generating T-dependent antibody responses (Xu et al., 1996). Third, full-length TRAF-3 augments the activating potential of TRAF-3 splice-deletion variants, which suggests that over-expression of full-length TRAF-3 alone is not sufficient to reveal its functional roles. Taken together, these considerations strongly suggest that TRAF-3 splice-deletion variants, which are capable of inducing NF-κB activation, may contribute to CD40 signaling in T-B cell interactions. An important goal of future studies will be to determine whether certain TRAF-3 isoforms, such as TRAF-3 Δ130, have special roles in CD40 signaling.

EXAMPLE 2

A Single Gene for Human TRAF-3 at Chromosome 14q32.3 Encodes a Variety of mRNA Species by Alternative Polyadenylation, mRNA Splicing and Transcription Initiation

[Abbreviations used: TRAF, TNF receptor-associated factor; TNF-R, Tumor Necrosis Factor Receptor; NIK, NF-κB-inducing kinase; Zn finger, zinc finger; IGHC, Immunoglobulin heavy chain constant region gene complex, ORF, open reading frame; UTR, untranslated region; RACE, rapid amplification of cDNA ends; RT, reverse transcriptase; FISH, fluorescence in situ hybridization; LOH, loss of heterozygosity; aa, amino acid; His-tagged, poly-histidine fusion construct; EST, Expressed Sequence Tag; cR, centi-Rays; Mb, megabase; kb, kilobase; HIGM, hyper-IgM syndrome.]

Human TRAF-3 is a signaling molecule that interacts with the cytoplasmic tails of CD40 and other TNF-receptor family members. TRAF-3 mRNA is expressed as two major classes of approximately 2 and 8 kb and a number of TRAF-3 encoding cDNA clones differ in discrete gene segments. Because this variety of mRNA species could result from mRNA processing events and/or multiple genes, the structure and localization of TRAF-3 encoding gene elements were determined. FISH and radiation hybrid mapping demonstrated that TRAF-3 is located at chromosome 14q32.3, approximately 1 Mb centromeric to the Ig heavy chain gene complex. Physical mapping of 4 overlapping genomic PAC clones established that TRAF-3 transcripts are encoded by a single gene, comprised of 13 exons spanning 130 kb. Alternative polyadenylation in the mRNA segment encoded by exon 12 accounts for the difference between the 2 kb and the 8 kb classes of transcripts. Alternative mRNA splicing in the coding region (encoded by exons 3–12) generates transcripts which delete exons 8 (75 nt), 7+8 (156 nt) or 8+9 (168 nt) and that encode distinct protein isoforms (Δ25, Δ52 and Δ56 aa, respectively). Alternative splicing of exon 2 (139 nt) and alternative transcriptional initiation result in mRNA species with distinct 5'UTRs. Together, these data indicate that a single TRAF-3 gene encodes a variety of mRNA species by a combination of alternative polyadenylation, alternative mRNA splicing and/or alternative initiation.

1. INTRODUCTION

Human TRAF-3 is a 568 amino acid (aa) cytoplasmic signaling molecule that interacts with the cytoplasmic tails of CD40 (Hu et al. 1994; Cheng et al. 1995; Mosialos et al. 1995; Sato et al. 1995) and other Tumor Necrosis Factor-Receptor (TNF-R) family members (e.g., LTβ-R, CD30 and Ox40) (Mosialos et al. 1995; Vanarsdale et al. 1997; Gedrich et al. 1996; Ansieau et al. 1996; Boucher et al. 1997; Arch and Thompson, 1998) Although the understanding of the role of TRAF-3 in signaling is still evolving, TRAF-3 is known to participate in CD40-mediated signaling (Cheng et al. 1995) and to play an important role in T helper function for B cells (Xu et al. 1996). Dissecting the role of TRAF-3 in signaling has been complicated, in part, due to the expression of mRNA transcripts encoding more than one TRAF-3 isoform (Mosialos et al. 1995; Sato et al. 1995; Krajewski et al. 1997). Therefore, as part of a larger effort to analyze the function of TRAF-3 gene products in signaling, the present study characterized the structure of TRAF-3 mRNA transcripts and the organization of the genetic elements that encode them.

TRAF-3 is a member of the TNF receptor-associated factor (TRAF) family of signal transducing molecules (Rothe et al. 1994), of which six members currently have been identified (TRAF-1 through 6) (Rothe et al. 1994; Regnier et al. 1995; Ishida et al. 1996; Nakano et al. 1996; Ishida et al. 1996; Kashiwada et al. 1998). The characteristic feature of TRAF-family members is the TRAF-C domain (Rothe et al. 1994; Cheng et al. 1995) and mutational analyses of the TRAF-3 TRAF-C domain show that it is critical for interactions with the cytoplasmic tails of the TNF-R family members (Cheng et al. 1995; Force et al. 1997) and with cytoplasmic proteins including, other TRAF-3 molecules (Cheng et al. 1995; Force et al. 1997), I-TRAF/TANK (Cheng and Baltimore, 1996; Rothe et al. 1996) and NF-κB-inducing kinase (NIK) (Regnier et al. 1997; Song et al. 1997; Malinin et al. 1997). Among the TRAF family members, TRAF-5 shares the closest homology with TRAF-3 and both interact with the same set of TNF-R family members' cytoplasmic tails (Ishida et al. 1996; Nakano et al. 1996; Aizawa et al. 1997; Kawamata et al. 1998). TRAF-2 and TRAF-1 share less homology with TRAF-3, but TRAF-2 binds several of the same TNF-R family members' cytoplasmic tails (Rothe et al. 1994; Rothe et al. 1995; Gedrich et al. 1996; Ansieau et al. 1996; Boucher et al. 1997; Arch and Thompson, 1998; Lee et al. 1996). Finally, TRAF-6 and TRAF-4 are most distantly related to TRAF-3 (Ishida et al. 1996; Kashiwada et al. 1998; Regnier et al. 1995). Although TRAF-6 interacts with the cytoplasmic tail of CD40, its binding site on the CD40 tail is distinct from that of TRAF-2, 3 or 5 (Ishida et al. 1996; Kashiwada et al. 1998). The genes for TRAF-1, 4 and 5 have been localized and are dispersed in the genome on different chromosomes (Regnier et al. 1995; Siemienski et al. 1997; Nakano et al. 1997). Although the genomic localization of human TRAF-3 is unknown, the murine TRAF-3 genomic structure has been partially characterized and localized to the distal region of chromosome 12, which has synteny with human 14q32 (Wang et al. 1996).

The functional roles of TRAF-3 in receptor-mediated signaling have been studied in cell lines by over-expression of full-length or truncated TRAF-3 peptides and in vivo by targeted disruption of the TRAF-3 gene. In this regard, over-expression of particular truncated forms of TRAF-3, that include the TRAF-C domain, inhibit signaling by CD40 or LTβ-R in a dominant-negative fashion (Cheng et al. 1995; Force et al. 1997; Eliopoulos et al. 1996). Further evidence for signaling by TRAF-3 gene products was derived from targeted disruption of the TRAF-3 gene in mice (Xu et al. 1996). Fetal liver cells from TRAF-3 deficient (−/−) embryos are capable of reconstituting all hematopoietic lineages after transfer to lethally irradiated mice (Xu et al. 1996). In these mice, the deficiency of TRAF-3 in lymphoid cells results in a severe and selective defect in the generation of antibody responses to T cell dependent antigens (Xu et al. 1996). This phenotype is similar to that of CD154 (CD40-L) deficient (Xu et al. 1994; Renshaw et al. 1994) and CD40 deficient (Kawabe et al. 1994; Castigli et al. 1994) lymphocytes in vivo, which suggests that TRAF-3 plays a role in CD40-mediated aspects of T cell-B cell collaboration. However, some CD40-mediated effects are preserved in TRAF-3 (−/−) lymphocytes, such as CD23 upregulation (Xu et al. 1996) A functional redundancy of TRAF-5 for TRAF-3 may account for this preserved aspect of CD40-signaling in TRAF-3 (−/−) lymphocytes, since over-expression of truncated TRAF-5 constructs inhibits CD40-mediated CD23 upregulation (Ishida et al. 1996). Nevertheless, the fact that TRAF-3 (−/−) lymphocytes are deficient in T cell-B cell collaboration in vivo is notable because a variety of other molecules are implicated in CD40-mediated signaling, including TRAF-2, 5 and 6 (Rothe et al. 1995; Ishida et al. 1996; Kashiwada et al. 1998), as well as other cytoplasmic factors (Morio et al. 1995; Hanissian and Geha, 1997).

Transient over-expression of full length TRAF-3 cDNA clones in cell lines inhibits NF-κB activation mediated by over-expression of CD40, TRAF-2 or TRAF-5 (Duckett et al. 1997; Rothe et al. 1995; Ishida et al. 1996; Devergne et al. 1996; Kawamata et al. 1998). The RING finger domain of TRAF-2, but not that of TRAF-3, confers NF-κB activating capacity to chimeric molecules (Takeuchi et al. 1996). However, the conclusion that TRAF-2 is an activator and TRAF-3 is an inhibitor of NF-κB activation may be premature, since an isoform of TRAF-2 (TRAF-2A) that contains an additional 7 aa in the RING finger domain has recently been isolated and found to be an inhibitor of TRAF-2 induced NF-κB activation (Brink and Lodish, 1998). The fact that "TRAF-2" is apparently a splice deletion variant of the "full length" TRAF-2A suggests that alternative mRNA splicing of TRAF-2 gene products regulates NF-κB activating capacity. These considerations suggest that regulation of signaling function by alternative splicing may be a feature of other members of the TRAF-family, such as TRAF-3. It is unknown if TRAF-3 isoforms exist that activate NF-κB, but this possibility is suggested by the observation that TRAF-3 binds NIK similarly to TRAF-1, 2, 5 and 6 (Regnier et al. 1997; Song et al. 1997; Malinin et al. 1997). Together, these findings indicate that the roles of TRAF-3 may be elucidated by understanding the precise structure of TRAF-3 isoforms.

Evidence for diverse TRAF-3 mRNA transcripts was first obtained from Northern blot analysis (Cheng et al. 1995; Mosialos et al. 1995; Wang et al. 1996) and comparison of the sequences of various TRAF-3 cDNA clones (Hu et al. 1994; Cheng et al. 1995; Sato et al. 1995; Mosialos et al. 1995). Both human and mouse TRAF-3 mRNA are expressed as two major classes of 2 and 8 kb (Cheng et al. 1995; Mosialos et al. 1995; Wang et al. 1996). Isolation of a 7.3 kb murine TRAF-3 cDNA clone (TRAFamn) and partial characterization of a murine TRAF-3 gene suggested that alternative polyadenylation controls the addition of 5 kb of 3'UTR to TRAF-3 transcripts (Wang et al. 1996). In addition, comparison of the reported sequences of the human TRAF-3 cDNA clones suggests that alternative splicing occurs in at least two regions. For example, comparison of the reported sequences of TRAF-3 (CD40bp) (Hu et al. 1994) and TRAF-3 (CRAF1) (Cheng et al. 1995) reveals that a region of 139 bp in the 5'UTR is not included in a subset of TRAF-3 cDNA clones. In addition, comparison of TRAF-3 (CAP-1) (Sato et al. 1995; Krajewski et al. 1997) with other TRAF-3 cDNA clones reveals that a 75 bp region is deleted in the coding region. Because TRAF-3 (CAP-1) encodes a protein with a 25 aa deletion in the Zn finger complex, it has been termed TRAF-3b (Krajewski et al. 1997). These studies demonstrate that a variety of TRAF-3 mRNA transcripts are expressed in cells. However, the mechanisms that generate these various TRAF-3 transcripts have not been studied systematically. Moreover, the structure and organization of the genetic elements encoding TRAF-3 have not been characterized and some of the variety of TRAF-3 transcripts could result from the existence of more than one TRAF-3 gene.

The present work characterized a number of TRAF-3 mRNA transcripts and the molecular structure and organization of the genetic elements that encode them. The structure and localization of the human TRAF-3 gene was determined by fluorescence in situ hybridization (FISH) analysis, radiation hybrid mapping and characterization of 4 overlapping genomic PAC clones. A single TRAF-3 gene was identified that contains 13 exons and spans approximately 130 kb at chromosome 14q32.3. Alternative polyadenylation in the mRNA encoded by exon 12 appends either 0.5 or 5.8 kb of 3'-untranslated region (UTR) and accounts for the difference between the 2 and 8 kb transcripts. Alternative mRNA splicing accounts for the TRAF-3b transcript (Sato et al. 1995; Krajewski et al. 1997) as well as for two other TRAF-3 transcripts that encode isoforms with 52 and 56 aa deletions in the Zn finger region, which alter the number and composition of the Zn fingers. Alternative splicing and alternative transcription initiation result in TRAF-3 transcripts with distinct 5'UTR sequences. Together, these studies demonstrate that a single human TRAF-3 gene accounts for the diverse TRAF-3 mRNA species, which are generated by alternative polyadenylation, alternative splicing and/or alternative transcriptional initiation.

2. MATERIALS & METHODS 2.1. Isolation and Characterization of TRAF-3 cDNA Clones Hybridization screening of a Raji B cell λ-gt11 cDNA library (Clontech Laboratories, Palo Alto, Calif.) yielded several TRAF-3 cDNA clones, including IIIb, Ib and 2-1. The cDNA inserts were cloned into the pbluescript SK(+) cloning vector (Stratagene, La Jolla, Calif.). In addition, 5'-rapid amplification of cDNA ends (RACE) was used to identify 5'-sequences of TRAF-3 with mRNA from D1.1, Raji or EBV-transformed B cells as templates (Boehringer Mannheim, Indianapolis, Ind.; Life Technologies, Gaithersburg, Md.; Clontech Laboratories). Although a number of TRAF-3 clones were identified and cloned into the pCR2.0 or pCR2.1 TA cloning vectors (Invitrogen, San Diego, Calif.) or the pBluescript SK(+) cloning vector (Stratagene), sequences further upstream of the 5'-termini of the λ-gt11 clones were not present in any of these 5'-RACE products. The sequence of the previously reported TRAF-3 (CRAF1) cDNA clone IIIb is deposited in GenBank under accession number: U21092 (Cheng et al. 1995). The nucleotide positions (nt) of the IIIb clone are used in this study.

The extended 5.8 kb TRAF-3 3'UTR was cloned as two overlapping cDNA fragments of approximately 4.7 kb (upstream) and 1.8 kb (downstream). The 4.7 kb cDNA clone was generated by reverse transcriptase (RT)-PCR, in which the RT reaction was primed with oligo(dT) and PCR amplification utilized the gene specific oligonucleotide primers, 3B1850F (5' GTCTTTGTGGCCCAAACTGT-TCTAGAAAATGG 3') (SEQ ID NO.: 6) and EST/Mu-CRAF1.R (5' GATTTGGGTGACAGACCCTCATT 3') (SEQ ID NO.: 7). The 1.8 kb cDNA clone was generated by 3'-RACE (Life Technologies) utlilizing an oligo(dT) primer (5' GGCCACGCGTCGACTAGTAC(T)$_{17}$ 3') (SEQ ID NO.: 8) and a gene specific forward oligonucleotide primer 5'CRAF-EST2(186).F (5' ATGCAGTTCTAGGCACAGCC 3') (SEQ ID NO.: 9). The PCR products (4,691 and 1,845 bp that overlap in a 672 bp segment) were cloned into the pCR2.0 or pCR2.1 TA cloning vectors (Invitrogen, San Diego, Calif.) or the pBluescript SK(+) cloning vector (Stratagene). The 4.7 and 1.8 kb cDNA clones are deposited in GenBank under accession numbers [and], respectively.

The cDNA clones containing deletions in the region coding for the Zn fingers were isolated by RT-PCR, in which the RT reaction was primed by oligo(dT) and PCR amplification utilized gene specific oligonucleotide primers. The PCR products were cloned into the pCR2.0 or pCR2.1 TA cloning vectors (Invitrogen).

2.2. Isolation and Characterization of Human Genomic λ-phage Clones

Three clones from a λ-FIX II genomic library (Stratagene) were identified by hybridization screening using the full length IIIb cDNA clone as a probe. All three phage clones were analyzed by restriction digestion, partial sequencing and PCR using primers derived from the IIIb cDNA sequence. Two of these clones (#4 and #9) overlap and represent the 3'-coding region and 3'UTR (IIIb nt 975–2433), while the third clone (#6) contains genomic sequence representing the 5'-coding region of TRAF-3 (IIIb nt 200–787).

2.3. Isolation of TRAF-3+ Human Chromosome 14q32.3 DNA Clones

PAC clones, representing the genomic region of TRAF-3, were identified by hybridization screening of segment RPCI1 of an arrayed human genomic PAC library). This library is described at the BacPac Resource Center at the Department of Human Genetics at Roswell Park Cancer Institute (http://bacpac.med.buffalo.edu/libchar.htm). Two PAC clones (PAC 167m5 and PAC 206o5) were identified by hybridization to $^{32}$P labeled TRAF-3 genomic PCR products (generated from the λ-FIX II clones). Two additional PAC clones (PAC 342f5 and PAC 373n17) were isolated by genomic walking using a probe representing the 5'-end of the PAC 167m5 insert.

2.4. DNA Preparation

The PAC clones were grown in LB media containing 25 $\mu$g ml$^{-1}$ Kanamycin (Sigma Chemical, St. Louis, Mo.). Individual colonies were grown for 15 h at 37° C. to saturation in a volume of 2 ml, followed by transfer to 30 ml of fresh media and grown for 4 h. Subsequently, this 30 ml culture was transferred to 1 liter of fresh media, grown for 1.5 h after which it was supplemented with 0.5 mM IPTG (Denville Scientific, Metuchen, N.J.) to increase the copy number. After an additional 5 h the bacteria were harvested and plasmid DNA was isolated using standard alkaline lysis and CsCl (Sigma) gradient ultra-centrifugation (Maniatis et al. 1982).

Human genomic DNA was extracted from the Ramos 2G6 B cell line (5×10$^7$ B cells), grown in Iscovels Modified Dulbecco's Medium (Life Technologies), supplemented with 10% fetal calf serum (Summit Biotechnology, Ft. Collins, Colo.) and 1% Penicillin/Streptomycin (Sigma). Cells were pelletted at 500×G for 5 min and washed in PBS twice, resuspended in 0.5 ml digestion buffer (100 mM NaCl, 10 mM TrisCl pH 8.0, 25 mM EDTA pH 8.0, 0.5% SDS and 0.1 mg/ml proteinase K), incubated with gentle shaking at 50° C. for 18 h, extracted three times with phenol-chloroform and dialyzed against TE for 24 h (Maniatis et al. 1982).

2.5. Genomic DNA Isolation and Subcloning

Mapping and analysis of genomic DNA was performed by PCR and restriction enzyme digestion. Genomic PCR was carried out using the Expand Long Template PCR System (Boehringer Mannheim) in a DNA Thermal Cycler 480 (Perkin Elmer/Cetus, Branchburg, N.J.). Typical PCR amplification reaction conditions were: initial denaturation for 4 min at 94° C. (1 cycle); denaturation for 30 sec at 94° C., annealing for 30 sec at 62° C., extension for 15 min at 68° C. (10 cycles); denaturation for 30 sec at 94° C., annealing for 30 sec at 62° C., extension for 15 min at 68° C. with an additional 20 sec per cycle (30 cycles) and final extension for 7 min at 68° C. Typically, PCR products were separated on a 1% agarose gel and visualized by ethidium bromide staining, followed by gel-isolation using the QIAquick® Gel Extraction System (Qiagen, Valencia, Calif.) and cloned into the pCR2.0 or pCR2.1 cloning vector (TA Cloning System, Invitrogen). Restriction enzyme digestion of PAC clones was performed using NotI and SalI (New England Biolabs, Beverly, Mass.) alone or in combination. DNA fragments were separated by Field Inversion Gel Electrophoresis (FIGE mapper system, Bio-Rad Laboratories, Hercules, Calif.) on a 1% agarose gel (SeaKem® gold, FMC BioProducts, Rockland, Me.) and blotted onto Hybond-N membranes (Amersham Life Science, Cleveland, Ohio) for Southern blot analysis (see below).

The 5'UTR exons and upstream genomic sequences were subcloned by EcoRI (New England Biolabs) digestion of PAC 206o5 DNA and ligation of two genomic DNA fragments, 7 kb and 3 kb in length, that contain exons 1a and 1b, and exon 2, respectively, into pBluescript SK(+) cloning vector (Stratagene) using T4 DNA ligase (New England Biolabs) 15 h at 16° C. The cloned 7 kb genomic EcoR1 fragment, containing exons 1a and 1b, is deposited in GenBank under accession number [ ].

2.6. mRNA Isolation and Characterization

Poly (A)$^+$ RNA was isolated from B cell lines Daudi, Ramos 2G6 (Siegel and Mostowski, 1990; Lederman et al. 1992), Raji and BA, and from T cell lines B2.7, D1.1 (Yellin et al. 1991), CEM and H9, using the Fast Track® System (Invitrogen). Poly (A)$^+$ RNA (4 $\mu$g) was run on a 0.8% agarose/formaldehyde gel for 5.5 h (4 Volts/cm) at 15° C. and blotted onto Hybond-N membranes (Amersham Life Science) for Northern blot analysis. RNA blots containing 2 $\mu$g poly (A)$^+$ RNA per lane from fifteen tissues were obtained from Clontech Laboratories for Northern analysis (see below).

2.7. Southern/Northern Blot Analysis

DNA or RNA on membranes was UV-crosslinked using a Stratalinker (Stratagene) and hybridized to [$\alpha$-$^{32}$P]dCTP random labeled dsDNA probes (NEBlot® System, New England Biolabs) or to [$\gamma$-$^{32}$P]ATP end-labeled oligonucleotide probes (polynucleotide kinase, Boehringer Mannheim). Unincorporated nucleotides were removed from the labeled probes using G-50 Sephadex® Quick Spin Columns (Boehringer Mannheim). Subsequently, the random labeled probes were denatured by boiling (5 min). Blots were incubated for 1.5 h at 42° C. in prehybridization solution (50% formamide, 5×SSCPE, 5×Denhart's solution, 1 mg ml$^{-1}$ salmon sperm DNA and 0.1% SDS), followed by incubation 15 h at 42° C. in hybridization solution (50% formamide, 5×SSCPE, 5×Denhart's, 100 $\mu$g ml$^{-1}$ salmon sperm DNA and 10% Dextran Sulfate) containing the radio-labeled probe. The blots were washed twice at 68° C. for 15–20 min in 2×SSC, 1% SDS and the hybridization patterns were visualized by autoradiography (BioMax MS® film, Eastman Kodak, Rochester, N.Y.).

2.8. DNA Sequencing and Sequence Analysis

Isolated PAC clones were sequenced manually by cycle sequencing (dsDNA Cycle Sequencing System®, Life Technologies). Sequence reactions were analyzed by denaturing PAGE (6% polyacrylamide/7 M Urea) and autoradiography (BioMax MS® film, Eastman Kodak). DNA fragments, cloned into the pCR2.0 or pCR2.1 TA cloning vector (Invitrogen) or the pBluescript SK(+) cloning vector (Stratagene), were sequenced on a automated ABI 373 DNA sequencer, by the DNA sequencing core facility at Columbia University or at the Molecular Resource Facility, New Jersey Medical School, UMDNJ. All sequence information was submitted to the BLAST server available through the National Center for Biotechnology Information (NCBI) (http://www.ncbi.nlm.nih.gov/BLAST) or the DNA analysis programs of the Genetics Computer Group (GCG, Madison, Wis.) for alignment with additional sequences, identification of repetitive elements or any other homology. Unique sequences were selected and submitted to the Primer3 server available through the Whitehead Institute for Biomedical Research/M.I.T. Center for Genome Research (http://www.genome.wi.mit.edu/cgi-bin/primer/primer3.cgi) or Amplify 1.2 (University of Wisconsin, Madison, Wis.) to design oligonucleotides (obtained from Life Technologies) used for PCR or sequencing.

2.9. FISH Analysis

Metaphase spreads of normal human PBL or the B cell line Ramos 2G6 were probed with genomic TRAF-3 λ-FIX II clone #6 as well as a digoxigenin labeled 14q32.3 telomeric probe (Oncor, Gaithersburg, Md.). Chromosome spreads were counterstained using DAPI. The genomic TRAF-3 probe was labeled with biotin by nick translation and detected with either streptavidin-FITC or streptavidin-rhodamine as previously described (Yu et al. 1996). Images were captured using the Applied Imaging Probevision system (Applied Imaging, Pittsburgh Pa.) and chromosomes were identified using an enhanced DAPI image.

2.10. Radiation Hybrid Screening

Radiation Hybrid screening was performed by Research Genetics (Huntsville, Ala.) on the Genebridge 4 panel using primers: F1gen (5' GAGAGAAATTCTGGCTCTTCA-GATCTATTGTCGG 3') (SEQ ID NO: 10), located in exon 3, and FR8gen (5' TGCAGTCAGGACGCACACATG-GAAG 3') (SEQ ID NO.: 11), located in exon 4. Vector data were submitted to the Whitehead Institute for Biomedical Research server for placement on the Whitehead framework map (http://www.genome.wi.mit.edu/cgi-bin/contig/rhmapper.pl).

3. RESULTS 3.1. Characterization of TRAF-3 Encoding mRNA Species

Figure 8A:
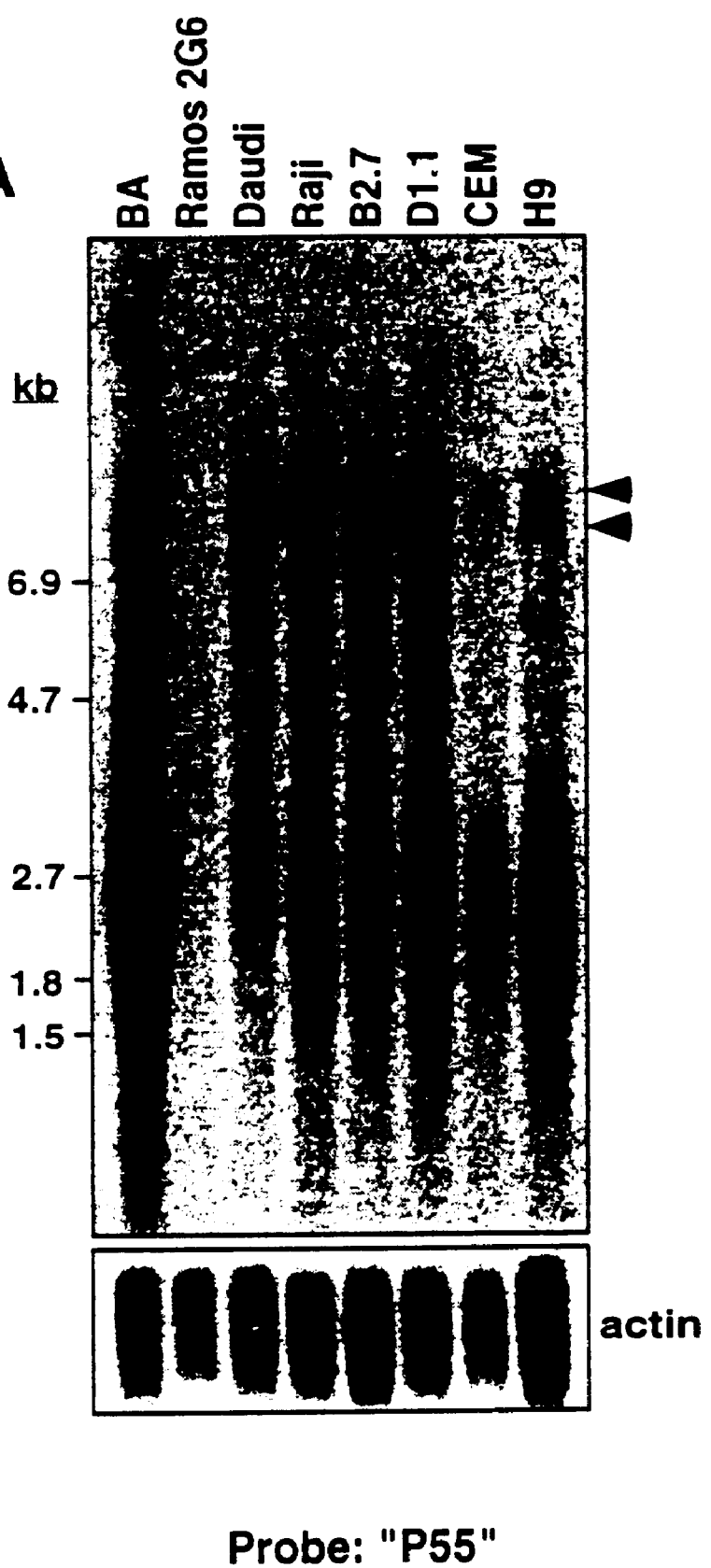
FIGS. 8A–C. Expression of human TRAF-3 mRNA in B and T cell lines.

TRAF-3 mRNA species were analyzed by hybridizing RNA blots from different human tissues (FIG. 7) with a probe ("P55", FIG. 2c) that represents the complete TRAF-3 open reading frame (ORF). Similar to previous reports (Cheng et al. 1995; Mosialos et al. 1995; Wang et al. 1996), TRAF-3 hybridizing mRNA species are expressed predominantly in lymph node and PBL and migrate as two major classes of transcripts, a 2 kb class (migrating as two bands of 2.2 and 2.6 kb) and an 8 kb class (migrating at 8.5 kb) (FIG. 7). The expression of TRAF-3$^+$ transcripts in spleen and thymus is notably low, consistent with recent immuno-histochemical analysis showing low levels of TRAF-3 protein in these tissues (Krajewski et al. 1997). The "P55" TRAF-3 probe also hybridized with the 2 kb class and the 8 kb class (migrating as two bands of 8.3 and 8.7 kb) of TRAF-3 mRNA transcripts from certain T and B cell tumor lines (FIG. 2a). The observed TRAF-3 specific hybridization pattern of mRNA from these cell lines is consistent with results from previous studies. For example, similar to the results in FIG. 2a, Ramos cells are known to have barely detectable TRAF-3 mRNA (Cheng et al. 1995) and protein (Krajewski et al. 1997). In addition, EBV transformed B cells, like BA (FIG. 8A), have high levels of TRAF-3 mRNA (Mosialos et al. 1995). Since the Raji B cell line, Jurkat D1.1 T cell line and EBV transformed B cells express both the 2 kb and 8 kb classes of TRAF-3 transcripts, further studies of TRAF-3 mRNA (below) were based on mRNA from Raji, Jurkat D1.1 or EBV transformed B cells.

3.2. Characterization of an Extended 3'UTR in 8 kb TRAF-3 cDNA

Figure 8B:
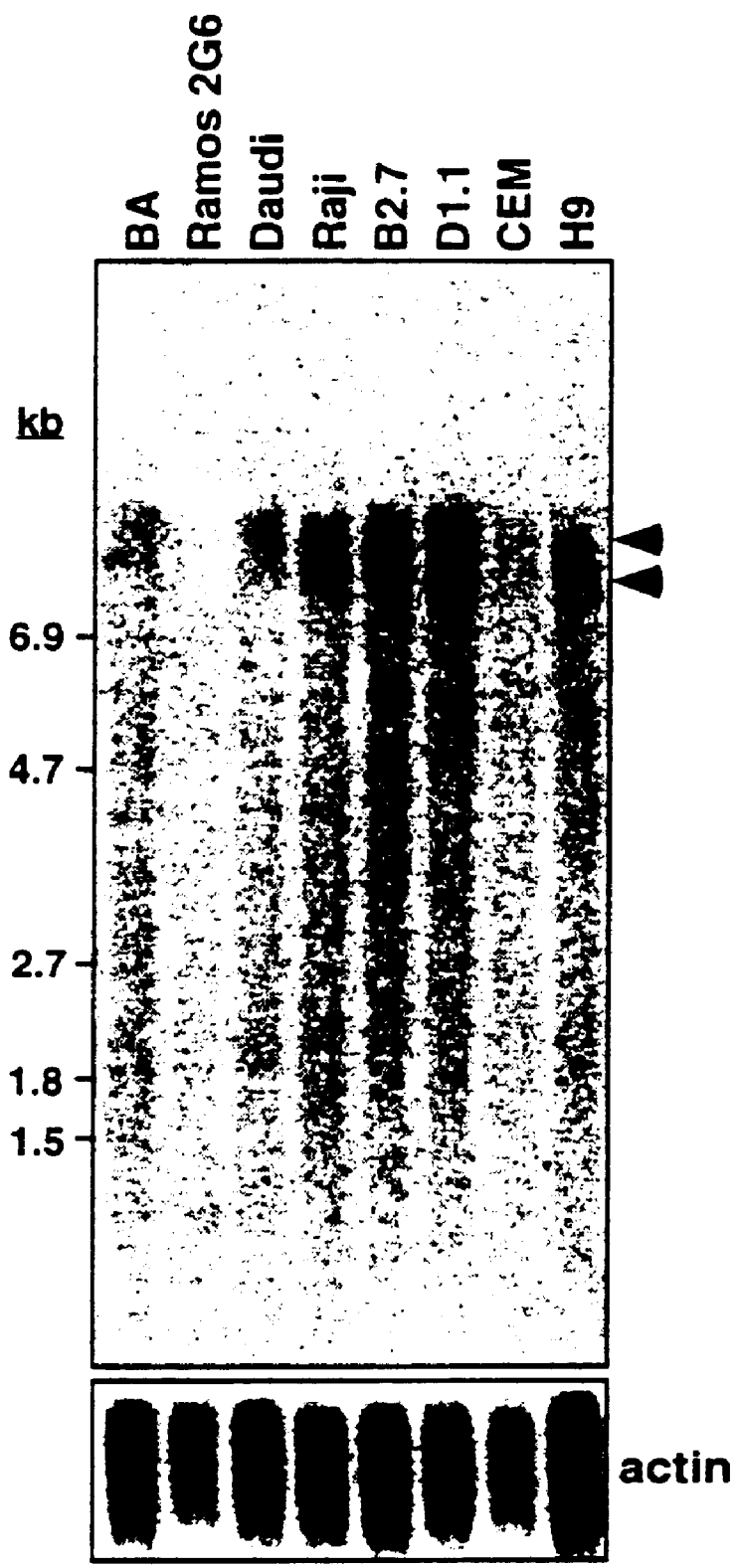

All previously reported human and murine TRAF-3 cDNA clones are approximately 2.4 kb in length and terminate in a similar region of the 3'UTR, except for the murine TRAF-3 cDNA clone (TRAFamn) reported by Lacy and coworkers (Wang et al. 1996), which is 7.3 kb in length and contains a 5 kb 3'UTR. During the course of the human genomic analysis (described below), a genomic sequence located 3' to the region encoding human TRAF-3 was noted to be homologous to a segment of the 3'UTR of the murine TRAF-3 (TRAFamn) cDNA clone. In addition, the human genomic sequence was identical to sequence elements of three deposited human Expressed Sequence Tags (ESTs) (GenBank accession numbers: AA035757, AA159960 and AA375889). Primers, derived from these sequences, were used in RT-PCR and 3'-RACE experiments to clone two overlapping cDNA clones (4.7 and 1.8 kb) that together represent a 5.8 kb cDNA segment, containing IIIb nt 1823 to 2433 followed by 5.3 kb of novel sequence that terminates in a poly-A$^+$ tail. Sequence analysis revealed that the 8 kb class transcripts utilize a canonical polyadenylation signal, AAUAAA (SEQ ID NO: 39) (located at nt 7617), 24 bp upstream of the start of the poly-A$^+$ tail. Together, these data suggest that these cDNA clones represent an extended human TRAF-3 3'UTR. To confirm that the 8 kb class TRAF-3$^+$ transcripts, as observed in FIGS. 7 and 8a, contain the novel 5.3 kb 3'UTR, RNA blots derived from the T and B cell lines were probed with a DNA segment from the 3'-end of the extended 3'UTR. The 8 kb class transcripts, but not the 2 kb transcripts, hybridize with the "3'UTR" probe (FIG. 8b). Taken together, these data show that the 8 kb class of TRAF-3 mRNA transcripts are distinguished by the presence of a 5.3 kb extended 3'UTR.

Figure 8C:
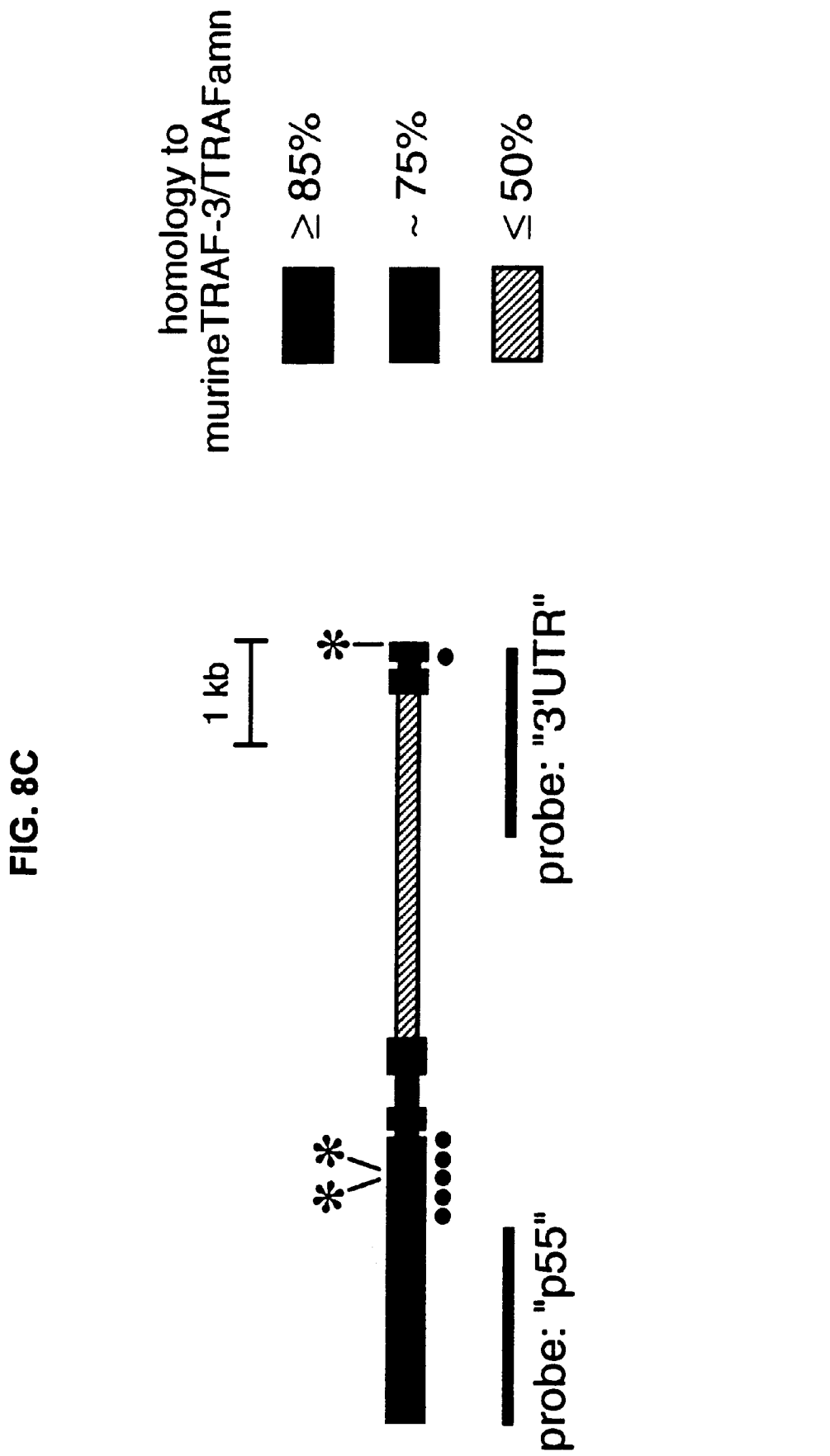

The sequences of the human TRAF-3 3'UTRs revealed segments of homology with murine TRAF-3 and certain regulatory elements. Comparison of the 3'UTR sequences of both the human and murine cDNA clones revealed two segments in the 3'UTR of both species that share 75% or higher identity. The first segment of high homology (>75%) is 2.0 kb and is located immediately after the stop codon, whereas the second is 0.5 kb and is located near the 3'-end of the extended 3'UTR. Interestingly, these two segments of relatively high homology are interrupted with a region of 3.3 kb with less than 50% homology with murine TRAF-3 (FIG. 8C). In addition, the human TRAF-3 3'UTR contains 6 AUUUA (SEQ ID NO:40) elements (IIIb nt 1944, 2133, 2335, 2529, 2774 and 7502), three of which are present exclusively in the extended 3'UTR of the 8 kb transcripts (2529, 2774 and 7502). Such elements have been implicated in transcript instability and/or suppression of mRNA translation of proto-oncogenes, transcription factors and cytokines (Chen and Shyu, 1995; Han et al. 1990; Kruys et al. 1987; Wilson and Treisman, 1988; Shaw and Kamen, 1986). The utility of sequence analysis to predict functional AUUUA (SEQ ID NO:41) elements is strengthened when these elements are flanked by U nucleotides (Chen and Shyu, 1995; Han et al. 1990; Kruys et al. 1987; Wilson and Treisman, 1988; Shaw and Kamen, 1986), which is the case for the AUUUA (SEQ ID NO:42) elements located at nt 2133 and 7502. In addition, both of these elements, as well as the AUUUA (SEQ ID NO:43) element at nt 2529, are conserved between human and mouse (Wang et al. 1996). Together, these data suggest that the 3'UTRs of both the 2 and 8 kb classes of TRAF-3 mRNA transcripts contain sequence elements that may regulate mRNA expression.

3.3. Diversity in the Region of cDNA Clones Encoding the Zn Finger Domain

In the coding region of the TRAF-3 cDNA, evidence for alternative splicing was first observed by the comparison of the sequences of TRAF-3b (CAP-1) cDNA (Sato et al. 1995) with the other reported TRAF-3 cDNA clones (Hu et al.

Figure 9:
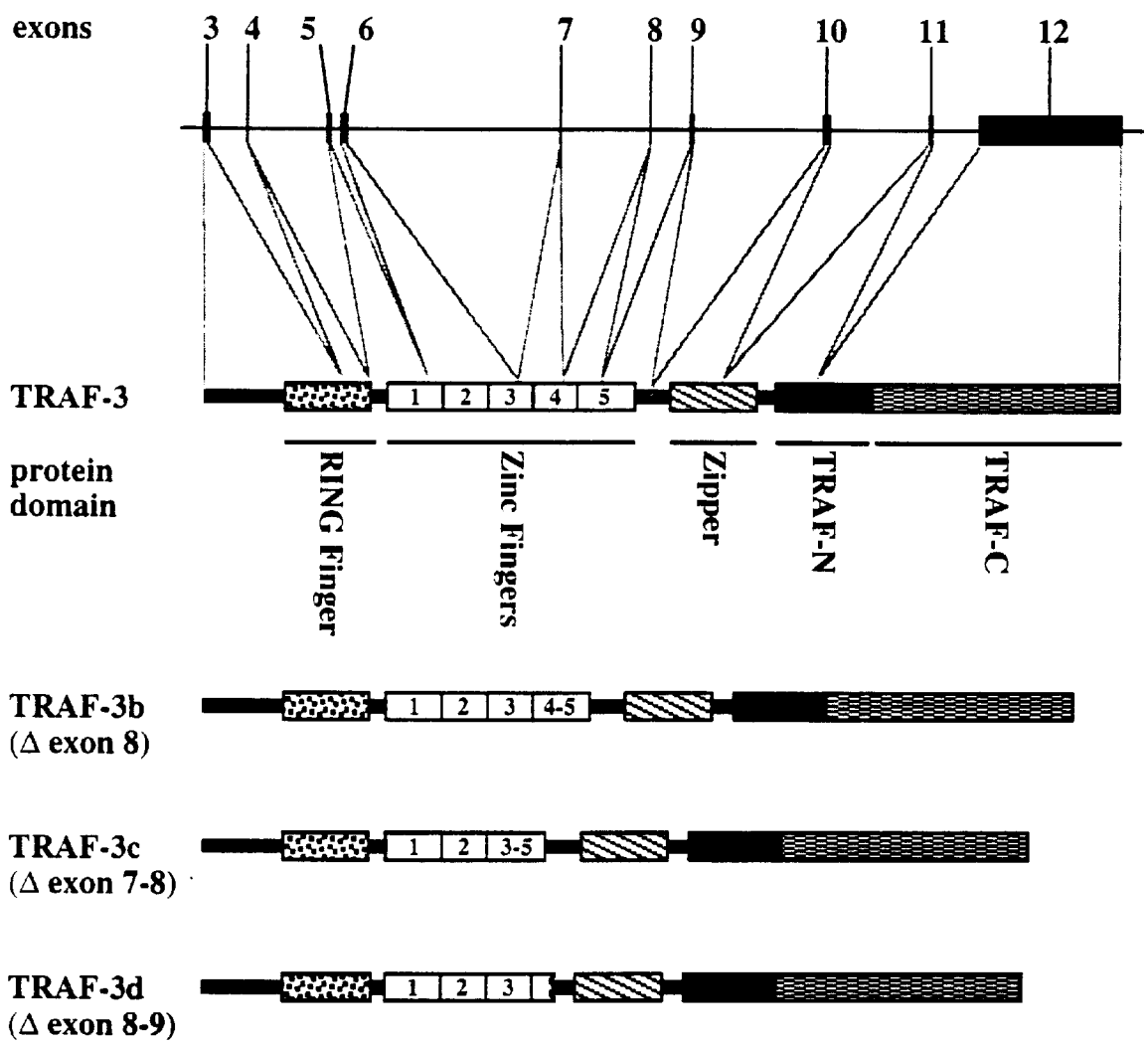
FIG. 9. Alternative splicing in the Zn finger domain of human TRAF-3. Shown on top is a representation of the genomic organization of the coding exons (3 through 12). Shown below is the TRAF-3 cDNA and the 5 protein domains it encodes. Shown on the bottom are three different cDNA clones that code for putative isoforms of TRAF-3 by alternatively splicing of exons 7, 8 and 9, resulting in variation in the composition of the individual Zn finger domains. Referring to the Zn finger number of full length TRAF-3, the Zn finger "4-5" in TRAF-3b results from the fusion of the C-terminal half of finger 4 and the N-terminal half of finger 5. Similarly, the Zn finger "3-5" in TRAF-3c results from the fusion of the C-terminal half of finger 3 and the N-terminal half of finger 5.

1994; Cheng et al. 1995; Mosialos et al. 1995). This analysis revealed that TRAF-3b (CAP-1) is identical to TRAF-3 except for a 75 nucleotide deletion (resulting in Δ25 aa (Δ aa 218–242)) in a region of TRAF-3 predicted to encode five atypical Zn fingers (FIG. 9). To examine the extent to which TRAF-3 mRNA species vary in this region, RT-PCR was performed using gene specific primers that amplify this region. These experiments revealed three distinct TRAF-3 PCR products that were cloned and characterized. Sequence analysis of these variant amplification products revealed deletions of 75 bp (IIIb nt 869–943), 156 bp (IIIb nt 788–943) and 168 bp (IIIb nt 869–1036) in the Zn finger-like region. In all three cases, the mRNA species maintain the ORF and therefore predict TRAF-3 isoforms (FIG. 9) The TRAF-3 cDNA clone containing the 75 bp (IIIb nt 869–943) deletion is identical to the previously reported TRAF-3b (CAP-1) (Sato et al. 1995). However, the two novel cDNA clones predict TRAF-3 isoforms which contain deletions of 52 aa (Δ_aa 191–242) and 56 aa (Δ_aa 218–273), respectively, in the Zn finger-like region. All three isoforms can be distinguished by the number of Zn fingers and the aa sequence of the most C-terminal finger. The Δ25 aa (TRAF-3b) isoform contains four Zn fingers with a C-terminal finger formed by the fusion of the N-terminal half of the $4^{th}$ and the C-terminal half of the $5^{th}$ finger (the numbering of segments in hybrid fingers refers to the location of these aa sequences in the 5 Zn fingers of full length TRAF-3) (FIG. 9). The Δ52 aa isoform contains three Zn fingers with a C-terminal finger formed by the fusion of the N-terminal half of the $3^{rd}$ and the C-terminal half of the $5^{th}$ finger (FIG. 9). The Δ56 aa isoform contains three complete Zn fingers and the N-terminal portion of the $4^{th}$ finger (FIG. 9). Following the nomenclature of Krajewski et al. (Krajewski et al. 1997), the two novel_putative proteins are designated TRAF-3c (Δ52 aa) and TRAF-3d (Δ56 aa).

3.4. Characterization of TRAF-3 cDNA Clones with Distinct 5'UTR Elements

Figure 10:
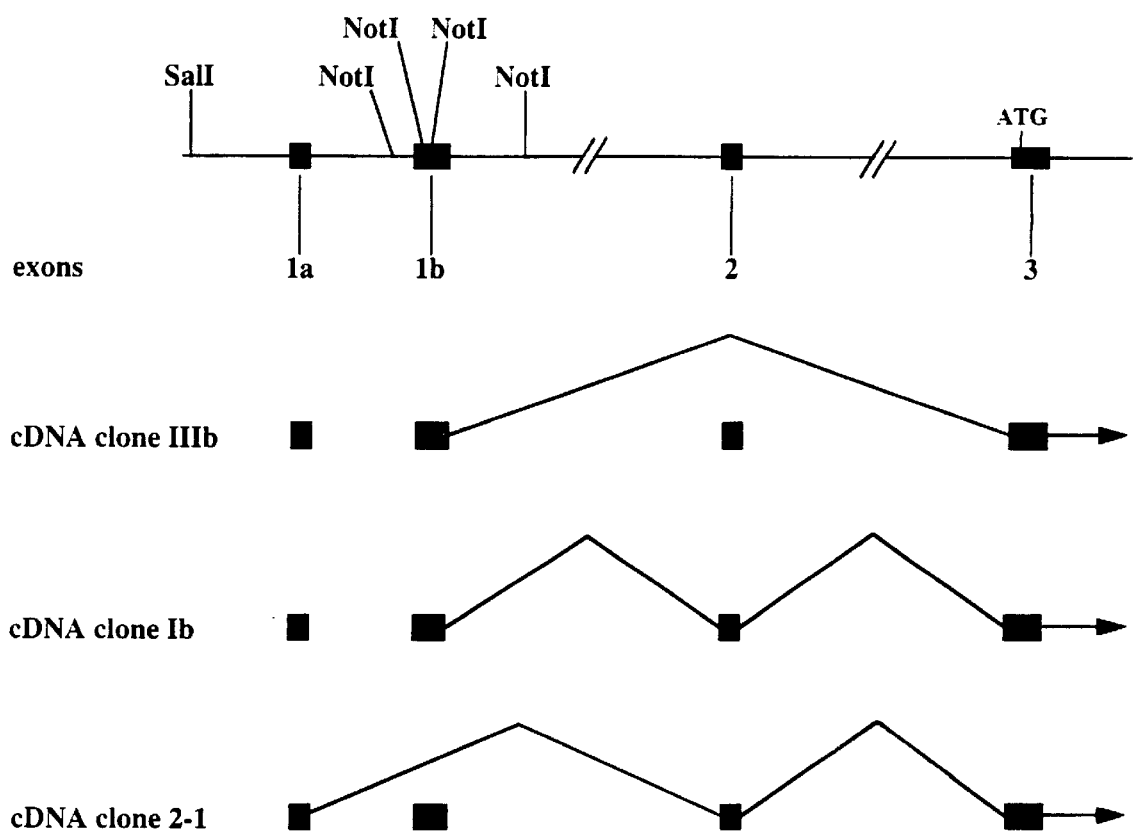
FIG. 10. Alternative splicing in the 5'UTR of human TRAF-3. Shown on top is a representation of the genomic organization of the 5'UTR exons (exons 1a, 1b and 2) and the first coding exon (exon 3). Shown below are three different cDNA clones. cDNA clone "IIIb" and "Ib" start in exon 1b, while cDNA clone "2-1" starts in exon 1a. The IIIb cDNA clone does not contain exon 2. All cDNA clones identified contain the translational start site in exon 3 and the ORF coding for TRAF-3, represented by the ATG and arrow after exon 3, respectively.

Comparison of TRAF-3 cDNA clones, isolated from a Raji B cell cDNA library or from 5'-RACE experiments using Raji or D1.1 mRNA, with each other and with TRAF-3 sequences previously reported (Hu et al. 1994; Cheng et al. 1995; Mosialos et al. 1995; Sato et al. 1995), revealed that distinct cDNA sequence elements were variably included in the 5'UTR of different clones (FIG. 10) For example, the IIIb and Ib cDNA clones differ by the presence, in the latter type, of a discrete 139 bp DNA segment, positioned 18 nt upstream of the translational start site (FIG. 10). Semi-quantitative analysis of 62 isolated cDNA clones, revealed that 85% contain the 139 bp segment while 15% lack this segment. Together, these data suggest that the 139 bp element is encoded by an exon that is variably included, resulting in mRNA species with distinct 5'UTRs.

Additional diversity in the 5'UTR of TRAF-3 was manifested by the characterization of the 2-1 and Ib cDNA clones that contain distinct sequences upstream of the 139 bp segment (FIG. 10). In the 2-1 cDNA clone, the 139 bp segment is preceded by all or part of a 141 bp element that contains a high G-C content (76%), while in the Ib cDNA clone, the 139 bp segment is preceded by all or part of a 200 bp element that is also G-C rich (82%) (FIG. 10). In both cases (the 141 bp element and the 200 bp element), 5'-RACE experiments did not yield additional upstream sequences, perhaps due to the G-C rich nature of these 5'UTR elements. The fact that the two distinct G-C rich elements were not observed in the same cDNA clones suggests that TRAF-3 transcripts initiate from two distinct start sites. Together, these data indicate that in addition to alternative mRNA splicing, alternative transcription initiation contributes to the diversity in the 5'UTR of TRAF-3 transcripts. To clarify the mechanism(s) by which these distinct TRAF-3 transcripts are generated, the next series of experiments characterized the genomic structure and localization of the genetic elements that encode them.

3.5. Genomic Localization of TRAF-3 by FISH and Radiation Hybrid Analysis

Figure 11A:
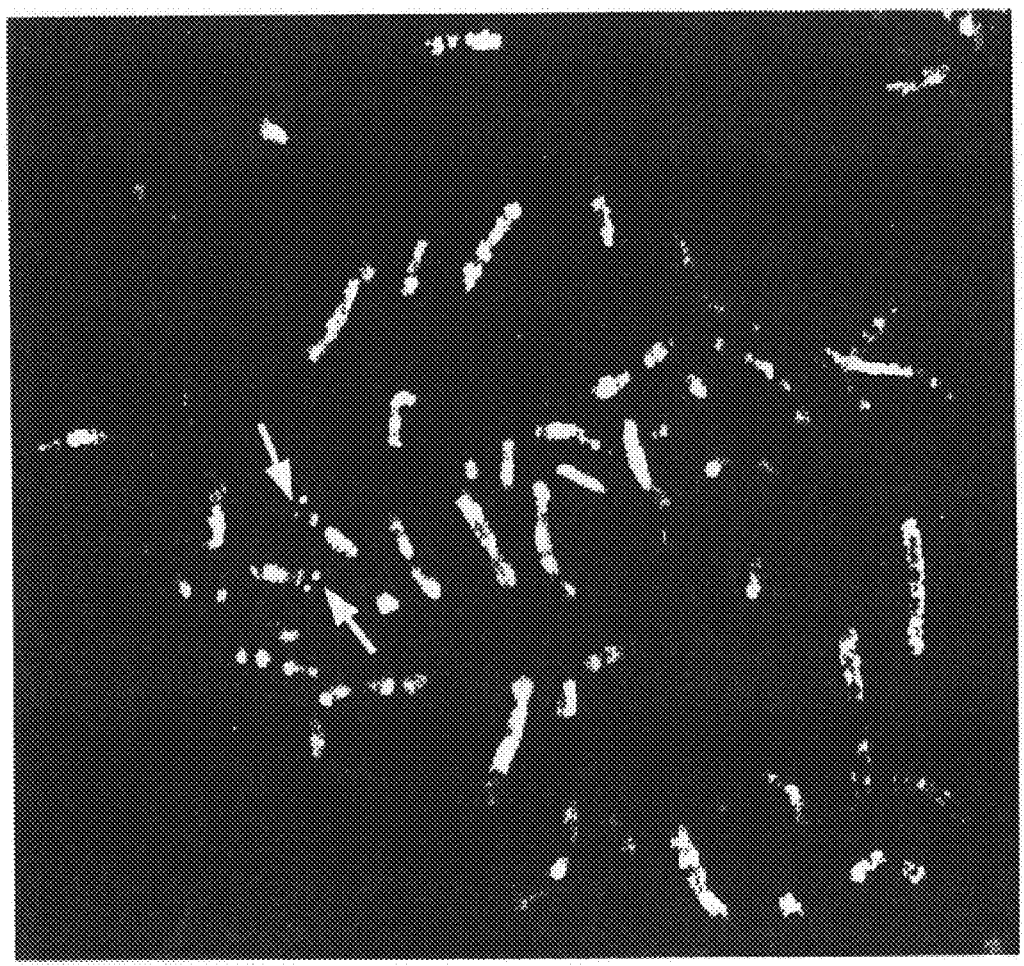
FIGS. 11A–B. FISH analysis of human TRAF-3.
Figure 11B:
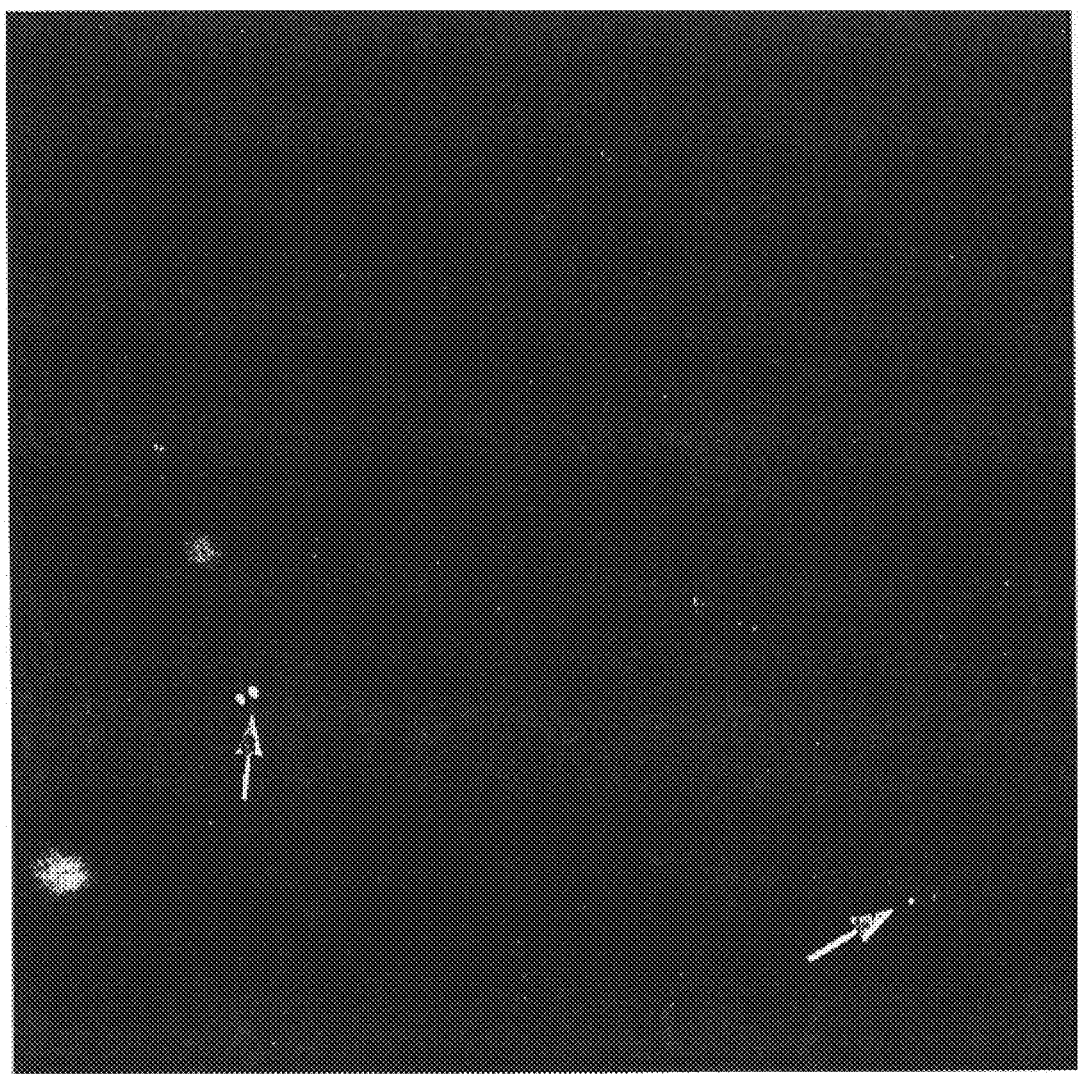

To identify the chromosomal localization of the TRAF-3 encoding gene(s), FISH analysis was performed by hybridization of normal human PBL metaphase spreads with a genomic TRAF-3 λ-FIXII clone #6 (containing IIIb nt 200–787). This probe bound specifically to the most telomeric region of the long arm of human chromosome 14, in band 14q32.3 (FIG. 11A), consistent with a single gene or gene cluster near the telomere of chromosome 14q. Since this region is known to contain the well-characterized breakpoint in Burkitt's lymphoma t(8;14)(q24.1;q32.3), TRAF-3 was localized with respect to this chromosomal breakpoint in the Ramos cell line. Two-color FISH analysis (Yu et al. 1996) was performed on metaphase spreads from Ramos 2G6 using a TRAF-3$^+$ λ-phage probe and a chromosome 14 telomere probe (FIG. 11B). The two probes bound in very close proximity on the normal chromosome 14. However, the TRAF-3 probe remained on the derivative chromosome 14, proximal to the breakpoint, whereas the chromosome 14 telomere probe was detected on the derivative chromosome 8, consistent with the translocation of this telomere to chromosome 8 in Ramos (FIG. 11B). Taken together, these data indicate that the genetic elements encoding TRAF-3 are located centromeric to the Ramos breakpoint on 14q32.3, which has been mapped to a precise location in the human Ig heavy chain gene complex (the Switch-$\mu$ region) (Wiman et al. 1984).

Figure 12:
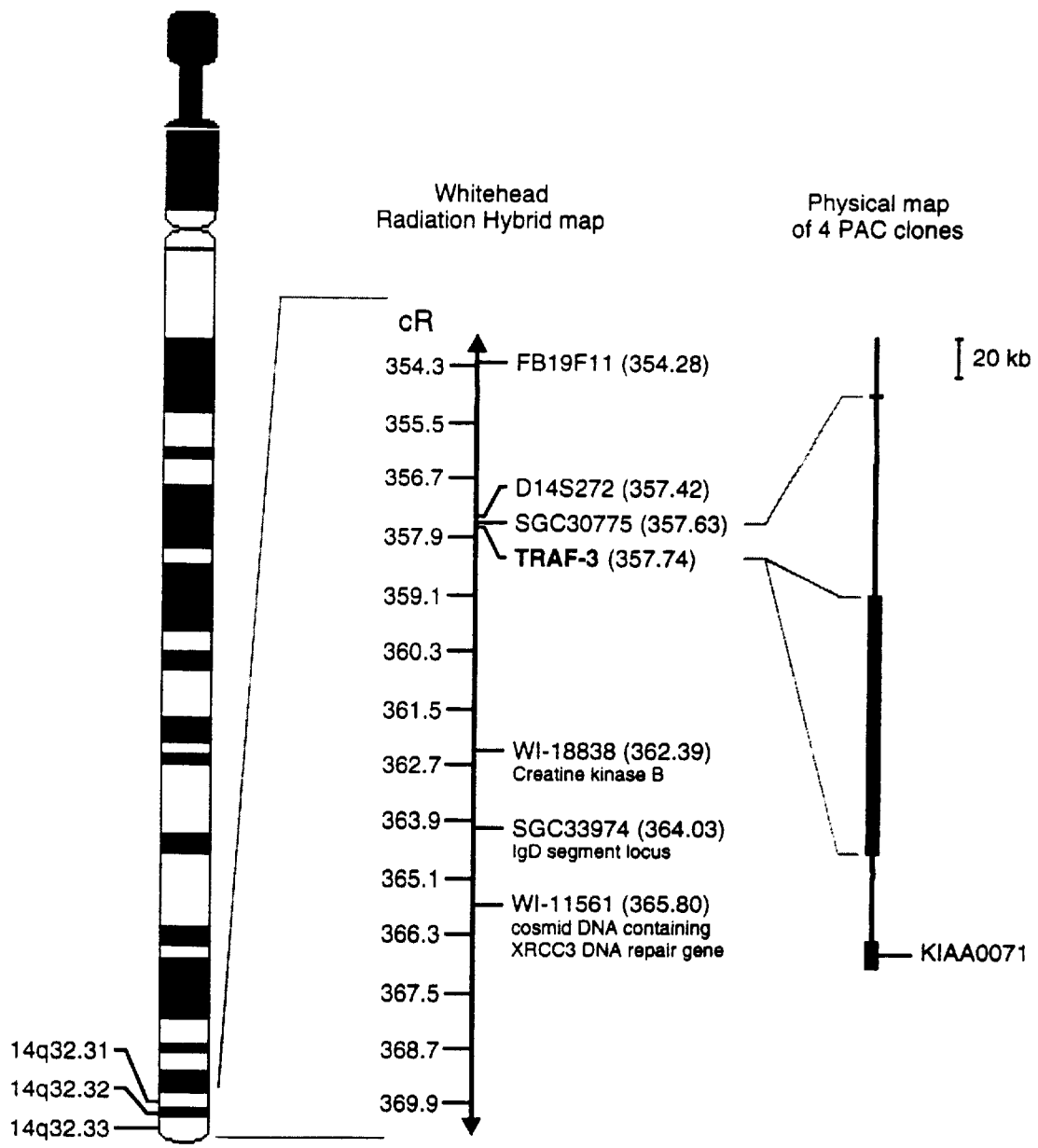
FIG. 12. Location of human TRAF-3 on chromosome 14q32.3. Shown is a representation of the telomeric region of chromosome 14 and the location of the gene for TRAF-3 in context of the Whitehead radiation hybrid map and the physical map of 4 overlapping PAC clones. Genomic markers are shown with their assigned position in parentheses. Genes that are represented by or linked to the genomic markers are listed below each marker.

Radiation Hybrid mapping confirmed and extended this analysis. Using PCR primers derived from the region encoding the RING finger domain that generate a 740 bp fragment (containing an intron) from genomic DNA, the position of a gene for TRAF-3 was determined more precisely on chromosome 14q32.3. The TRAF-3 gene is located 3.46 centiRays (cR) from framework marker FB19F11, which is 354.28 cR from the top of chromosome 14 on the Whitehead radiation hybrid map (FIG. 12). Together with the FISH analysis, these data demonstrate that TRAF-3 is encoded by a single gene or gene cluster located at 14q32.3.

3.6. Analysis of Intron-exon Structure of the TRAF-3 Gene.

To further characterize the genetic elements encoding TRAF-3, hybridization screening of a λ-FIX II and a PAC library yielded 3 genomic phage clones and 4 overlapping genomic PAC clones which were analyzed by PCR, Southern blotting and partial sequencing. These studies established that the phage and PAC clones contain all of the TRAF-3 encoding genetic elements represented in the TRAF-3 cDNA clones isolated. Furthermore, comparison of the genomic cDNA sequences allowed the establishment of the intron-exon junctions of exons 2 through 12 as well as the 3' boundaries of exons 1a and 1b (FIG. 14). All intronexon junctions conform to the GT/AG rule (Breathnach and Chambon, 1981). The establishment of the intron-exon structure also allowed the superimposition of the five predicted protein domains of TRAF-3 onto the exon structure (FIG. 9). The RING finger (IIIb nt 353–523) is encoded by exons 3 through 5; the Zn finger domain (nt 545–1009) by exons 5–9; the isoleucine zipper domain (nt 1076–1243) by exons 10 and 11; The TRAF-N domain (nt 1283–1462) by exons 11 and 12; and the TRAF-C domain (nt 1463-stop ) solely by exon 12 (FIG. 9). In addition, sequence analysis of the extended 5.8 kb 3'UTR (described above) and of the genomic region that encodes the extended 3'UTR, revealed that the cDNA is co-linear with the genomic sequence until the 3'-polyadenylation site (nt 7640) in exon 12, after which the sequences diverge (FIG. 9). The 2 kb class of transcripts appear to utilize either of two signals; a non-canonical polyadenylation signal, AGUAAA (SEQ ID NO:44) (nt 2323), or a canonical signal, AAUACA (SEQ ID NO:45) (nt 2401) (Hu et al. 1994; Cheng et al. 1995; Sato et al. 1995; Mosialos et al. 1995; Parthasarathy et al. 1997). Together, these data indicate that alternative polyadenylation is the mechanism that generates the 2 kb or 8 kb classes of TRAF-3 transcripts.

The identification and analysis of the intron-exon borders revealed that alternative mRNA splicing accounts for several of the mRNA species observed (described above). In this regard, the mRNA encoded by the 139 bp exon 2 is variably included in certain TRAF-3 cDNA clones, such as Ib and 2-1 (FIG. 10). In addition, the TRAF-3b encoding transcript (CAP-1) lacks exon 8 and the transcripts encoding the putative TRAF-3c and TRAF-3d protein isoforms result from deletion of exon 7 and 8 ($\Delta$52 aa) or deletion of exon 8 and 9 ($\Delta$56 aa), respectively (FIG. 9). Alternative splicing of these exons does not disrupt the ORF, since the splice junctions between exons 7 and 9 (TRAF-3b), exons 6 and 9 (TRAF-3c) and exons 7 and 10 (TRAF-3d) are of the same class (class 0) as each of the other splice junctions between exons 5 through 10 (FIG. 14).

3.7. Physical Map of the TRAF-3 Gene Locus

Figure 13:
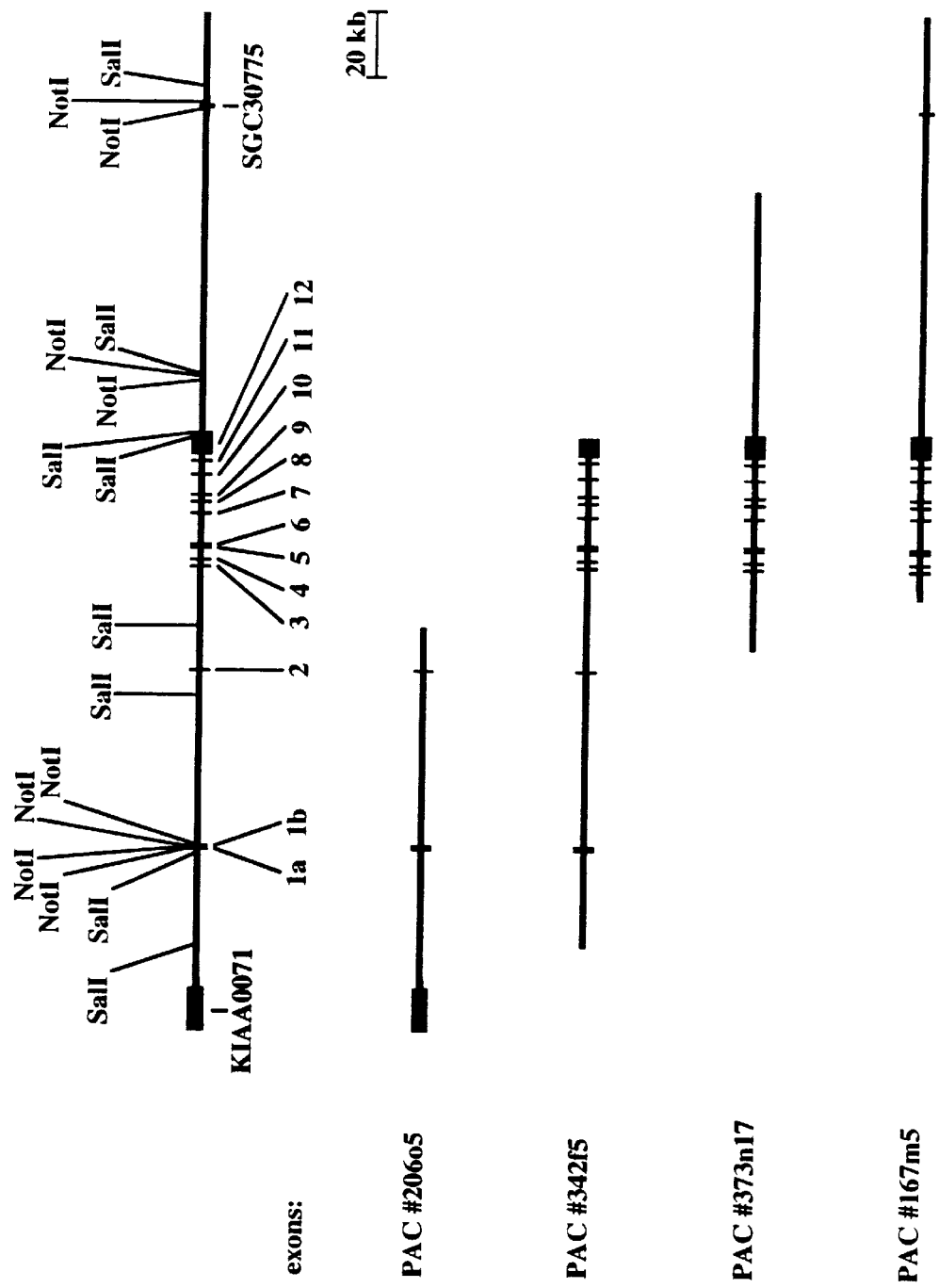
FIG. 13. Physical map of the human TRAF-3 gene. Shown on top is a representation of the exon distribution of the TRAF-3 gene with positions of the restriction sites of NotI and SalI and two other genomic markers, KIAA0071 and SGC30775. Below are 4 overlapping PAC clones that span the complete TRAF-3 gene. Exons are indicated by bold lines for TRAF-3, KIAA0071 and SGC30775.

The analysis of the 4 genomic PAC clones provides a physical map of the genomic locus of the TRAF-3 gene (FIG. 13). The gene for TRAF-3 consists of 13 exons that span a genomic region of 130 kb. Exons 1a and 1b are closely spaced (~800 bp) in a region with a high G-C content (~80%) and characteristics of a CpG island, which are found at the 5'-end of most housekeeping genes and of many other genes that are expressed in a tissue specific pattern (Wenger et al. 1998; Cross and Bird, 1995; Gardiner-Garden and Frommer, 1987). In contrast, exons 1a and 1b are separated from exon 2 by a 54 kb intron and exon 2 is separated from exon 3 by a 32 kb intron. The coding exons (exons 3–12) are relatively compactly situated in a genomic region of 41 kb, with the nine introns between exons 3 through 12 ranging in size from approximately 0.6 to 9.5 kb.

The next series of experiments sought to physically link the TRAF-3 gene with other genomic markers. Two other genomic markers, SGC30775 and D14S272, are mapped at a similar distance as TRAF-3 from framework marker FB19F11 on the Whitehead radiation hybrid map. Therefore, to determine whether these two genomic markers are represented on the PAC clones, PCR was performed with primers derived from the sequences of these two markers using the PAC clones as templates. These studies revealed that SGC30775 is located on PAC 167m5, whereas D14S272 was not be detected on any of the PAC clones. The presence of SGC30775 on PAC 167m5 was confirmed by directly sequencing PAC 167m5 in this region. In addition, Southern blot analysis positioned SGC30775 approximately 100 kb downstream of TRAF-3 exon 12.

Since D14S272 was not detected on any of the PAC clones, the PAC clones were also analyzed for the presence of other genomic markers that are closely linked to D14S272 on the Human Transcript Map (available through the NCBI server at http://www.ncbi.nlm.nih.gov/cgi-bin/SCIENCE96). Primers derived from the 3'-end sequence of one of these genomic markers, a 5241 nt cDNA clone KIAA0071 (GenBank accession number: D31888), specifically amplify the predicted product from PAC 206o5. The presence of KIAA0071 on PAC 206o5 was confirmed by directly sequencing PAC 206o5 in this region. Subsequently, PCR and Southern blot analysis revealed that the 3'-end of KIAA0071 is located approximately 40 kb upstream of TRAF-3 exon 1a and that this gene is situated in the same transcriptional orientation as TRAF-3 (FIG. 13). The unambiguous radiation hybrid mapping of the 740 bp TRAF-3 exon 3-exon 4 PCR product to a single region of 14q32.3 and the physical mapping of the 4 PAC clones strongly suggest that TRAF-3 is a single gene. Together these data establish the physical relationship of TRAF-3 with two genomic markers at 14q32 and indicate that TRAF-3 is encoded by a single gene located in the subtelomeric region.

As stated above, radiation hybrid mapping showed that the TRAF-3 gene is located 3.46 centiRays (cR) from framework marker FB19F11, which is 354.28 cR from the top of chromosome 14 on the Whitehead radiation hybrid map (FIG. 12). From this analysis, TRAF-3 could be located at 357.74 cR or at 350.82 cR. The physical linkage of TRAF-3 to SGC30775, which is at 357.63 cR, and located approximately 100 kb downstream of TRAF-3, establish the location of TRAF-3 at 357.74 cR from the top of chromosome 14 and approximately 13.5 cR from the telomere (FIG. 12). In addition, the radiation hybrid and physical mapping indicate that the TRAF-3 gene is situated at a distance of 6.29 cR from genomic marker SGC33974 (364.03 cR), the sequence of which is identical to a portion of the human IgD segment locus (GenBank accession number: X97051). Together with the fact that the IgD segment locus is approximately 400 kb telomeric to the 3'-end of the Ig heavy chain constant region complex (IGHC) (Hofker et al. 1989), these data suggest that the TRAF-3 gene is located at a distance of approximately 1 Mb from the 3'-end of the IGHC.

4. DISCUSSION

The genomic structure of TRAF-3 was characterized by FISH analysis, radiation hybrid mapping and characterization of four overlapping PAC clones which demonstrate that a single TRAF-3 gene is located on chromosome 14q32.2, contains 13 exons, and spans 130 kb within 13.5 cR of the telomere. To generate a variety of mRNA transcripts, the TRAF-3 gene utilizes two alternative starting exons (1a and 1b, respectively), alternative splicing of a non-coding exon 2, alternative splicing of certain of the 10 coding exons (exons 7–9) and alternative processing of a 3'UTR of approximately 5.8 kb (accounting for the 2 and 8 kb classes of mRNA transcripts). Together, these data indicate that a single TRAF-3 gene codes for diverse transcripts by a combination of alternative initiation, alternative splicing and alternative polyadenylation.

A number of TRAF-3 mRNA species are generated by alternative splicing of coding exons (7, 8, and 9) which lead to the generation of mRNA species that predict TRAF-3 peptides which have distinct aa sequences in the region encoding Zn fingers. Evidence for this type of posttranslational modification was first observed by the isolation of a cDNA encoding TRAF-3b ($\Delta$25) by Sato et al. (Sato et al. 1995). The data presented in this paper suggest the existence of additional isoforms; $\Delta$52 and $\Delta$56. Following the nomenclature of Reed (Krajewski et al. 1997), the new putative TRAF-3 isoforms have been termed TRAF-3c and TRAF-3d, respectively. Like TRAF-3b, both TRAF-3c and TRAF-3d predict proteins with a reduced number of Zn fingers and a distinct composition of the most C-terminal Zn finger domains as compared to TRAF-3. The fact that removal or insertion of one or a combination of certain exons (7–9)

encoding the Zn fingers does not alter the ORF is due to the common class of splice junctions (class 0, the junction of two exons falls between two codons). It is of potential interest that the splice junctions between exons 4 through 11 are all of class 0. The common splice junctions of these exons suggests that additional splice variants involving exons 5, 6 and/or 10 may yet be identified, perhaps in combinations with deletions of exons 7–9, that would encode novel TRAF-3 proteins. In this regard, deletions of exon 5 would alter the RING finger domain and may affect signaling function.

It is unknown whether these or other TRAF-3 isoforms are expressed as proteins and if so, whether they have functional significance. However, the possible functional roles of such splice deletion variants are intriguing, because RING finger and Zn finger domains are known to mediate either protein-protein and protein-DNA interactions. In this regard, it is of interest that alternative mRNA splicing results in a TRAF-2 isoform (TRAF-2A) that contains an insertion of 7 aa in the RING finger domain, and inhibits NF-κB activation by TNF-R stimulation (Brink and Lodish, 1998). These data indicate that the inhibitory isoform, TRAF-2A, is "full length" and that the NF-κB activating isoform, "TRAF-2", is a splice deletion variant (Brink and Lodish, 1998). Therefore, the fact that full length TRAF-3 inhibits NF-κB activation must be considered in the context that cDNA clones encoding smaller TRAF-3 isoforms have been identified, but not yet studied for their functional capabilities in receptor-mediated signaling. Therefore, future studies will address whether such isoforms are expressed and if so, whether such isoforms regulate TRAF-3 functions by regulating its interaction with other constituents of the cytoplasmic signaling apparatus.

In addition to the splice variants identified in this paper, Kieff and coworkers (Mosialos et al. 1995) reported the characterization of a TRAF-3 cDNA that predicts a peptide which initiates translation at methionine 350 (aa350–568). The peptide predicted from such a transcript would be 26 aa longer than the His-tagged, truncated form, C26 (containing murine aa324–567)) that we previously showed to inhibit CD40-mediated upregulation of CD23 (Cheng et al. 1995) and 29 aa longer than a related truncated form (containing murine aa 327–567) that inhibits CD40-mediated growth inhibition of epithelial cells (Eliopoulos et al. 1996). If a TRAF-3 isoform is expressed by the mRNA splice variant initiating translation at methionine 350 (aa350–568), such an isoform would contain the TRAF-C domain, but would lack both the RING and the Zn finger domains.

In the 5'UTR, further variety in TRAF-3 transcripts was found to be mediated by alternative splicing of exon 2 in a subset of transcripts and by utilization of two alternative 5'UTR encoding exons, 1a and 1b. Because the sequence elements encoded by exons 1a and 1b were not observed in the same cDNA clone, these two exons appear to represent alternative initiating exons. However, it should be noted that the precise transcriptional start sites were not identified, perhaps due to the G-C rich nature of exons 1a and 1b (76% and 82%, respectively). The function of the diversity generated by alternative splicing and alternative transcriptional initiation in the 5'UTR may regulate the level of TRAF-3 transcripts or protein expression. For instance, the high G-C content in the two initiating exons may regulate TRAF-3 expression by maintaining a "closed" conformation that does not allow the translation machinery to proceed through this area in the transcript (Kozak, 1989a; Kozak, 1989b; Kim et al. 1992; Romeo et al. 1993). In this light, it should be noted that upstream of the TRAF-3 initiating exons no conventional promoter with a "TATA-box" and/or "CAAT-box" was identified. This sequence analysis suggests that the gene for TRAF-3 contains "TATA-less" promoters, upstream of exon 1a and 1b, which is consistent with the overall high G-C content of the genomic region in which exon 1a and 1b are located. Moreover, this region contains typical characteristics of a CpG island (Gardiner-Garden and Frommer, 1987), which are found in the 5'-ends and promoters of most housekeeping genes and in many genes with tissue-specific expression (Wenger et al. 1998; Cross and Bird, 1995; Gardiner-Garden and Frommer, 1987). Therefore, it is possible that the differences in the 5'UTR lead to regulation of the level of TRAF-3 expression in a lineage- and/or differentiation-specific fashion (Krajewski et al. 1997).

Results of chromosomal FISH analysis, radiation hybrid mapping and physical characterization of the 4 PAC clones in this study indicate that TRAF-3 is a single copy gene located on chromosome 14q32.3. In this regard, the genes for human TRAF-1, 4 and 5 have been mapped and are dispersed in the genome at chromosomes 9q33–34, 17q11–12 and 1q32, respectively (Nakano et al. 1997; Regnier et al. 1995; Siemienski et al. 1997). In addition, the genomic organizations of TRAF-1 and 4 have been determined and comparison between TRAF-3 and TRAF-1 and 4 reveal both similarities and differences. First, the TRAF-3 gene spans approximately 130 kb and is substantially larger than TRAF-1 (12 kb) or TRAF-4 (5.5 kb) genes. Second, the TRAF-C domains of TRAF-3 and TRAF-4 are contained on single exons, whereas the TRAF-C domain of TRAF-1 is divided into 4 exons (Nakano et al. 1997; Regnier et al. 1995; Siemienski et al. 1997). In this regard, the differences in genomic organization between TRAF-3 and TRAF-1 could reflect the fact that, based on protein and DNA homology, TRAF-3 is relatively distantly related to TRAF-1. It will be of interest to determine the genomic organizations of TRAF-2, 5 and 6 to understand the phylogenetic relationships of these genes in more detail.

The localization of human TRAF-3 to 14q32.3 is of interest, because murine TRAF-3 is located on the distal region of murine chromosome 12, which has synteny with human 14q32 (Wang et al. 1996). In both species, the proximity of TRAF-3 to the IGHC is maintained. The region of human chromosome 14q32.3, that contains the TRAF-3 gene, is known to have a relatively high rate of recombination (Hofker et al. 1990). In addition, 14q32.3 is the site of many translocation breakpoints. In this regard, several genes that contribute to the transformed phenotype of lymphoid malignancies have been identified that translocate into the IGHC including; myc (Taub et al. 1982), CCND1 (BCL-1) (Motokura et al. 1991), BCL-2 (Tsujimoto et al. 1984), BCL-3 (Ohno et al. 1990), BCL-6 (Ye et al. 1993) and lyt-10 (Neri et al. 1991). However, TRAF-3 is approximately 1 Mb centromeric to the IGHC and is not involved in translocations associated with these lymphoid malignancies, since these translocation junctions have been well characterized. However, in a type of childhood acute leukemia in which blasts have both lymphoid and myeloid ("mixed lineage") features (Hayashi et al. 1990), the translocation junction in 14q32.3 occurs centromeric to IgH locus and the involvement of TRAF-3 has not been excluded. In addition, 14q telomeric deletions, involving 14q32.3, have been observed as loss of heterozygosity (LOH) in renal oncocytomas (Schwerdtle et al. 1997), non-papillary renal cell carcinomas (Schullerus et al. 1997) and malignant meningiomas (Simon et al. 1995; Tse et al. 1997; Menon et al. 1997). Future studies will address whether such translocations or LOH involves TRAF-3, and if so, whether alterations in the level of TRAF-3 expression contributes to a transformed phenotype, as would be the case for a proto-oncogene or a tumor suppressor gene.

The characterization of the PAC clones presented in this study is also of interest because this region has not yet been mapped by yeast artificial chromosomes (YACs) (Hofker et al. 1990; Chen et al. 1995). It is possible that the high rate of recombination in this region affects the stability of such large clones (Wintle et al. 1997). In this regard, the PAC clones described in this study may contain segments of DNA that were considered "unclonable" (Kang and Cox, 1996). Therefore, the PAC clones and the physical map of TRAF-3 described in this work may be useful, not only in the establishment of the TRAF-3 transcriptional orientation and the physical linkage of TRAF-3 with respect to the IGHC, but also in the further characterization of 14q32.3 (Cox et al. 1995).

Furthermore, the chromosomal localization of TRAF-3 and the structural characterization of the TRAF-3 gene may be useful in studying genetic immunodeficiency syndromes. For example, a subset of individuals with hyper-IgM syndrome (HIGM) have normal CD154 (Callard et al. 1994; Conley et al. 1994) and the role of TRAF-3 in CD40 signaling suggests that TRAF-3 defects might result in similar phenotypes. In this regard, TRAF-3 deficient lymphocytes share features with CD154 deficient (Xu et al. 1994) or CD40 deficient (Kawabe et al. 1994; Castigli et al. 1994) lymphocytes in mice in vivo (Xu et al. 1996). In addition, the fact that truncated forms of TRAF-3 inhibit CD40 signaling suggests that mutations affecting TRAF-3 splicing or that translocation events involving TRAF-3 may result in abnormal CD40 signaling that might manifest as HIGM. Therefore, the chromosomal localization of TRAF-3, and the physical mapping reported in this paper, will be useful in characterizing the structure of TRAF-3 genes in such individuals.

EXAMPLE 3

Gene Therapy

The invention features expression vectors for in vivo transfection and expression in particular cell types of TRAF-3 deletion isoform mutants so as to antagonize the function of wild type CD40 receptor-associated factor in an environment in which the wild-type protein is expressed (i.e., introduce abnormal TRAF-3 deletion isoform that acts as a dominant negative protein to inhibit CD40 signaling).

Expression constructs of TRAF-3 deletion isoform polypeptides may be administered in any biologically effective carrier that is capable of effectively delivering a polynucleotide sequence encoding the TRAF-3 isoform to cells in vivo. Approaches include insertion of the subject gene in viral vectors including recombinant retroviruses, baculovirus, adenovirus, adeno-associated virus and herpes simplex virus-1, or recombinant bacterial or eukaryotic plasmids. Viral vectors transfect cells directly, plasmid DNA can be delivered with the help of, for , example, cationic liposomes or derivatized (e.g., antibody conjugated) polylysine conjugates, gramacidin S, artificial viral envelopes or other such intracellular carriers, as well as direct injection of the gene construct or $CaPO_4$ precipitation carried out in vivo.

Any of the methods known in the art for the insertion of polynucleotide sequences into a vector may be used. See, for example, Sambrook et al., *Molecular Cloning: A Laboratory Manual*, Cold Spring Harbor Laboratory, Cold Spring Harbor, N.Y. (1989) and Ausubel et al., *Current Protocols in Molecular Biology*, J. Wiley & Sons, N.Y. (1992), both of which are incorporated herein by reference. Conventional vectors consist of appropriate transcriptional/translational control signals operatively linked to the polynucleotide sequence for a particular anti-fibrotic polynucleotide sequence. Promoters/enhancers may also be used to control expression of anti-fibrotic polypeptide. Promoter activation may be tissue specific or inducible by a metabolic product or administered substance. Such promoters/enhancers include, but are not limited to, the native E2F promoter, the cytomegalovirus immediate-early promoter/enhancer (Karasuyama et al., *J. Exp. Med.*, 169: 13 (1989)); the human beta-actin promoter (Gunning et al., *Proc. Natl. Acad. Sci. USA*, 84: 4831 (1987); the glucocorticoid-inducible promoter present in the mouse mammary tumor virus long terminal repeat (MMTV LTR) (Klessig et al., *Mol. Cell. Biol.*, 4: 1354 (1984)); the long terminal repeat sequences of Moloney murine leukemia virus (MuLV LTR) (Weiss et al., *RNA Tumor Viruses*, Cold Spring Harbor Laboratory, Cold Spring Harbor, N.Y. (1985)); the SV40 early region promoter (Bernoist and Chambon, *Nature*, 290:304 (1981)); the promoter of the Rous sarcoma virus (RSV) (Yamamoto et al., *Cell*, 22:787 (1980)); the herpes simplex virus (HSV) thymidine kinase promoter (Wagner et al., *Proc. Natl. Acad. Sci. USA*, 78: 1441 (1981)); the adenovirus promoter (Yamada et al., *Proc. Natl. Acad. Sci. USA*, 82: 3567 (1985)).

Expression vectors compatible with mammalian host cells for use in gene therapy of tumor cells include, for example, plasmids; avian, murine and human retroviral vectors; adenovirus vectors; herpes viral vectors; and non-replicative pox viruses. In particular, replication-defective recombinant viruses can be generated in packaging cell lines that produce only replication-defective viruses. See *Current Protocols in Molecular Biology*: Sections 9.10–9.14 (Ausubel et al., eds.), Greene Publishing Associates, 1989.

Specific viral vectors for use in gene transfer systems are now well established. See for example: Madzak et al., *J. Gen. Virol.*, 73: 1533–36 (1992: papovavirus SV40); Berkner et al., *Curr. Top. Microbiol. Immunol.*, 158: 39–61 (1992: adenovirus); Moss et al., *Curr. Top. Microbiol. Immunol.*, 158: 25–38 (1992: vaccinia virus); Muzyczka, *Curr. Top. Microbiol. Immunol.*, 158: 97–123 (1992: adeno-associated virus); Margulskee, *Curr. Top. Microbiol. Immunol.*, 158: 67–93 (1992: herpes simplex virus (HSV) and Epstein-Barr virus (HBV)); Miller, *Curr. Top. Microbiol. Immunol.*, 158: 1–24 (1992: retrovirus); Brandyopadhyay et al., *Mol. Cell. Biol.*, 4: 749–754 (1984: retrovirus); Miller et al., *Nature*, 357: 455–450 (1992: retrovirus); Anderson, *Science*, 256: 808–813 (1992: retrovirus), all of which are incorporated herein by reference.

Several methods of transferring potentially therapeutic genes to defined cell populations are known. See, e.g., Mulligan, "The Basic Science of Gene Therapy", Science, 260, pp. 920–31 (1993). These methods include:

1) Direct gene transfer. See, e.g., Wolff et al., "Direct Gene transfer Into Mouse Muscle In Vivo", *Science*, 247, pp. 1465–68 (1990);

2) Liposome-mediated DNA transfer. See, e.g., Caplen et al., "Liposome-mediated CFTR Gene Transfer To The Nasal Epithelium of Patients With Cystic Fibrosis", *Nature Med.*, 3, pp. 39–46 (1995); Crystal, "The Gene As A Drug", *Nature Med.*, 1, pp. 16–17 (1995); Gao and Huang, "A Novel Cationic Lipoma Reagent For Efficient Transfection Of Mammalian Cells", *Biochem. Biophys. Res. Comm.*, 179, pp. 280–85 (1991);

3) Retrovirus-mediated DNA transfer. See, e.g., Kav et al., "In Vivo Gene Therapy Of Hemophilia B: Sustained Partial Correction In Factor IX-Deficient Dogs", *Science*, 262, pp. 117–19 (1993); Anderson, "Human Gene Therapy", *Science*, 256, pp. 808–13 (1992);

4) DNA Virus-mediated DNA transfer. Such DNA viruses include adenoviruses (preferably Ad-2 or Ad-0 based vectors), herpes viruses (preferably herpes simplex virus based vectors), baculoviruses, and parvoviruses (preferably "defective" or non-autonomous parvovirus based vectors, more preferably adeno-associated virus based vectors, most preferably AAV-2 based vectors). See, e.g. Ali, et al., "The Use Of DNA Viruses As Vectors For Gene Therapy", *Gene Therapy*, 1, pp. 367–84 (1994); U.S. Pat. No. 4,797,368, incorporated herein by reference, and U.S. Pat. No. 5,139,941, incorporated herein by reference.

The choice of a particular vector system for transferring the gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity.

REFERENCES FOR EXAMPLE 1

Alt, F. W., Bothwell, A. L., Knapp, M., Siden, E., Mather, E., Koshland, M., and Baltimore, D. (1980). Synthesis of secreted and membrane-bound immunoglobulin mu heavy chains is directed by mRNAs that differ at their 3' ends. Cell 20, 293–301.

Arch, R. H. and Thompson, C. B. (1998). 4-1BB and Ox40 are members of a tumor necrosis factor (TNF)-nerve growth factor receptor subfamily that bind TNF receptor-associated factors and activate nuclear factor kappaB. Mol.Cell Biol. 18, 558–565.

Boucher, L. M., Marengere, L. E., Lu, Y., Thukral, S., and Mak, T. W. (1997). Binding sites of cytoplasmic effectors TRAF1, 2, and 3 on CD30 and other members of the TNF receptor superfamily. Biochem.Biophys.Res.Commun. 233, 592–600.

Brink, R. and Lodish, H. F. (1998). Tumor necrosis factor receptor (TNRF)-associated factor 2A (TRAF2A), a TRAF2 splice variant with an extended RING finger domain that inhibits TNFR2-mediated NF-kappaB activation. Journal of Biological Chemistry 273, 4129–4134.

Castigli, E., Alt, F. W., Davidson, L., Bottaro, A., Mizoguchi, E., Bhan, A. K., and Geha, R. S. (1994). CD40-deficient mice generated by recombination-activating gene-2-deficient blastocyst complementation. Proc.Natl.Acad.Sci.U.S.A. 91, 12135–12139.

Cheng, G. and Baltimore, D. (1996). TANK, a co-inducer with TRAF2 of TNF- and CD40L-mediated NF-kappaB activation. Genes Dev. 10, 963–973.

Cheng, G., Cleary, A. M., Ye, Z-s., Hong, D. I., Lederman, S., and Baltimore, D. (1995). Involvement of CRAF1, a relative of TRAF, in CD40 signaling. Science 267, 1494–1497.

Dadgostar, H. and Cheng, G. (1998). An intact zinc ring finger is required for tumor necrosis factor receptor-associated factor-mediated nuclear factor-kappaB activation but is dispensable for c-Jun N-terminal kinase signaling. J Biol.Chem. 273, 24775–24780.

Force, W. R., Cheung, T. C., and Ware, C. F. (1997). Dominant negative mutants of TRAF3 reveal an important role for the coiled coil domains in cell death signaling by the lymphotoxin-beta receptor. J.Biol.Chem. 272, 30835–30840.

Gedrich, R. W., Gilfillan, M. C., Duckett, C. S., Van Dongen, J. L., and Thompson, C. B. (1996). CD30 contains two binding sites with different specificities for members of the tumor necrosis factor receptor-associated factor family of signal transducing proteins. J.Biol.Chem. 271, 12852–12858.

Hu, H. M., O'Rourke, K., Boguski, M. S., and Dixit, V. M. (1994). A novel RING finger protein interacts with the cytoplasmic domain of CD40. J.Biol.Chem. 269, 30069–30072.

Ishida, T., Mizushima Si, Azuma, S., Kobayashi, N., Tojo, T., Suzuki, K., Aizawa, S., Watanabe, T., Mosialos, G., Kieff, E., Yamamoto, T., and Inoue, J. (1996). Identification of TRAF6, a novel tumor necrosis factor receptor-associated factor protein that mediates signaling from an amino-terminal domain of the CD40 cytoplasmic region. J.Biol.Chem. 271, 28745–28748.

Ishida, T. K., Tojo, T., Aoki, T., Kobayashi, N., Ohishi, T., Watanabe, T., Yamamoto, T., and Inoue, J. (1996). TRAF5, a novel tumor necrosis factor receptor-associated factor family protein, mediates CD40 signaling. Proc.Natl.Acad.Sci.U.S.A. 93, 9437–9442.

Kashiwada, M., Shirakata, Y., Inoue, J. I., Nakano, H., Okazaki, K., Okumura, K., Yamamoto, T., Nagaoka, H., and Takemori, T. (1998). Tumor necrosis factor receptor-associated factor 6 (TRAF6) stimulates extracellular signal-regulated kinase (ERK) activity in CD40 signaling along a ras-independent pathway. J.Exp.Med. 187, 237–244.

Kawabe, T., Naka, T., Yoshida, K., Tanaka, T., Fujiwara, H., Suematsu, S., Yosida, N., Kishimoto, T., and Kikutani, H. (1994). The immune responses in CD40-deficient mice: impaired immunoglobulin class switching and germinal center formation. Immunity 1, 167–178.

Kawamata, S., Hori, T., Imura, A., Takaori-Kondo, A., and Uchiyama, T. (1998). Activation of OX40 signal transduction pathways leads to tumor necrosis factor receptor-associated factor (TRAF) 2- and TRAF5-mediated NF-kappaB activation. J Biol.Chem. 273, 5808–5814.

Krajewski, S., Zapata, J. M., Krajewska, M., VanArsdale, T., Shabaik, A., Gascoyne, R. D., and Reed, J. C. (1997). Immunohistochemical analysis of in vivo patterns of TRAF-3 expression, a member of the TNF receptor-associated factor family. J. Immunol. 159, 5841–5852.

Malinin, N. L., Boldin, M. P., Kovalenko, A. V., and Wallach, D. (1997). MAP3K-related kinase involved in NF-kappaB induction by TNF, CD95 and IL-1. Nature 385, 540–544.

Mosialos, G., Birkenbach, M., Yalamanchili, R., VanArsdale, T., Ware, C., and Kieff, E. (1995). The Epstein-Barr virus transforming protein LMP1 engages signaling proteins for the tumor necrosis factor receptor family. Cell 80, 389–399.

Pullen, S. S., Miller, H. G., Everdeen, D. S., Dang, T. T. A., Crute, J. J., and Kehry, M. R. (1998). CD40-tumor necrosis factor receptor-associated factor (TRAF) interactions: regulation of CD40 signaling through multiple TRAF binding sites and TRAF hetero-oligomerization. Biochemistry 37, 11836–11845.

Regnier, C. H., Tomasetto, C., Moog-Lutz, C., Chenard, M. P., Wendling, C., Basset, P., and Rio, M. C. (1995). Presence of a new conserved domain in CART1, a novel member of the tumor necrosis factor receptor-associated protein family, which is expressed in breast carcinoma. J.Biol.Chem. 270, 25715–25721.

Renshaw, B. R., Fanslow, W. C.3., Armitage, R. J., Campbell, K. A., Liggitt, D., Wright, B., Davison, B. L., and Maliszewski, C. R. (1994). Humoral immune responses in CD40 ligand-deficient mice. J.Exp.Med. 180, 1889–1900.

Rothe, M., Sarma, V., Dixit, V. M., and Goeddel, D. V. (1995). TRAF2-mediated activation of NF-kappa-B by TNF Receptor 2 and CD40. Science 269, 1424–1427.

Rothe, M., Wong, S. C., Henzel, W. J., and Goeddel, D. V. (1994). A novel family of putative signal transducers associated with the cytoplasmic domain of the 75 kDa tumor necrosis factor receptor. Cell 78, 681–692.

Rothe, M., Xiong, J., Shu, H. B., Williamson, K., Goddard, A., and Goeddel, D. V. (1996). I-TRAF is a novel TRAF-interacting protein that regulates TRAF-mediated signal transduction. Proc.Natl.Acad.Sci.U.S.A. 93, 8241–8246.

Sato, T., Irie, S., and Reed, J. C. (1995). A novel member of the TRAF family of putative signal transducing proteins binds to the cytosolic domain of CD40. FEBS Letters 358, 113–118.

Screaton, G. R., Xu, X. N., Olsen, A. L., Cowper, A. E., Tan, R., McMichael, A. J., and Bell, J. I. (1997). LARD: a new lymphoid-specific death domain containing receptor regulated by alternative pre-mRNA splicing. Proc.Natl.Acad Sci.U.S A 94, 4615–4619.

Song, H. Y., Regnier, C. H., Kirschning, C. J., Goeddel, D. V., and Rothe, M. (1997). Tumor necrosis factor (TNF)-mediated kinase cascades: bifurcation of nuclear factor-kappaB and c-jun N-terminal kinase (JNK/SAPK) pathways at TNF receptor-associated factor 2. Proc.Natl.Acad.Sci.U.S.A. 94, 9792–9796.

Takeuchi, M., Rothe, M., and Goeddel, D. V. (1996). Anatomy of TRAF2. Distinct domains for nuclear factor-kappaB activation and association with tumor necrosis factor signaling proteins. J.Biol.Chem. 271, 19935–19942.

Tran, K., Merika, M., and Thanos, D. (1997). Distinct functional properties of IkappaB alpha and IkappaB beta. Mol.Cell Biol. 17, 5386–5399.

van Eyndhoven, W. G., Frank, D., Kalachikov, S., Cleary, A. M., Hong, D. I., Cho, E., Nasr, S., Perez, A. J., Mackus, W. J. M., Cayanis, E., Wellington, S., Fischer, S. G., Warburton, D., and Lederman, S. (1998). A single gene for human TRAF-3 at chromosome 14q32.3 encodes a variety of mRNA species by alternative polyadenylation, mRNA splicing and transcription initiation. Mol. Immunol. 35, 1189–2106.

Vanarsdale, T. L., VanArsdale, S. L., Force, W. R., Walter, B. N., Mosialos, G., Kieff, E., Reed, J. C., and Ware, C. F. (1997). Lymphotoxin-beta receptor signaling complex: role of tumor necrosis factor-associated factor 3 recruitment in cell death and activation of nuclear factor kappaB. Proc.Natl.Acad.Sci.U.S.A. 94, 2460–2465.

Xu, J., Foy, T. M., Laman, J. D., Elliott, E. A., Dunn, J. J., Waldschmidt, T. J., Elsemore, J., Noelle, R. J., and Flavell, R. A. (1994). Mice deficient for the CD40 ligand. Immunity 1, 423–431.

Xu, Y., Cheng, G., and Baltimore, D. (1996). Targeted disruption of TRAF3 leads to postnatal lethality and defective T-dependent immune responses. Immunity 5, 407–415.

Yamamoto, H., Kishimoto, T., and Minamoto, S. (1998). NF-kappaB activation in CD27 signaling: involvement of TNF receptor-associated factors in its signaling and identification of functional region of CD27. J Immunol. 161, 4753–4759.

Yang, Y., Chang, J. F., Parnes, J. R., and Fathman, C. G. (1998). T cell receptor (TCR) engagement leads to activation-induced splicing of tumor necrosis factor (TNF) nuclear pre-mRNA. J Exp.Med 188, 247–254

REFERENCES FOR EXAMPLE 2

Aizawa S., Nakano H., Ishida T., Horie R., Nagai M., Ito K., Yagita H., Okumura K., Inoue J. and Watanabe T. (1997) Tumor necrosis factor receptor-associated factor (TRAF) 5 and TRAF2 are involved in CD30-mediated NFkappaB activation. J. Biol. Chem. 272, 2042–2045.

Ansieau S., Scheffrahn I., Mosialos G., Brand H., Duyster J., Kaye K., Harada J., Dougall B., Hubinger G., Kieff E., Herrmann F., Leutz A. and Gruss H. J. (1996) Tumor necrosis factor receptor-associated factor (TRAF)-1, TRAF-2, and TRAF-3 interact in vivo with the CD30 cytoplasmic domain; TRAF-2 mediates CD30-induced nuclear factor kappa B activation. Proc. Natl. Acad. Sci. U. S. A. 93, 14053–14058.

Arch R. H. and Thompson C. B. (1998) 4-1BB and Ox40 are members of a tumor necrosis factor (TNF)-nerve growth factor receptor subfamily that bind TNF receptor-associated factors and activate nuclear factor kappaB. Mol. Cell Biol. 18, 558–565.

Boucher L. M., Marengere L. E., Lu Y., Thukral S. and Mak T. W. (1997) Binding sites of cytoplasmic effectors TRAF1, 2, and 3 on CD30 and other members of the TNF receptor superfamily. Biochem. Biophys. Res. Commun. 233, 592–600.

Breathnach R. and Chambon P. (1981) Organization and expression of eucaryotic split genes coding for proteins. Annu. Rev. Biochem. 50, 349–383.

Brink R. and Lodish H. F. (1998) Tumor necrosis factor receptor (TNRF)-associated factor 2A (TRAF2A), a TRAF2 splice variant with an extended RING finger domain that inhibits TNFR2-mediated NF-kappaB activation. J. Biol. Chem. 273, 4129–4134.

Callard R. E., Smith S. H., Herbert J., Morgan G., Padayachee M., Lederman S., Chess L., Kroczek R. A., Fanslow W. C. and Armitage R. J. (1994) CD40 ligand (CD40L) expression and B cell function in agammaglobulinemia with normal or elevated levels of IgM (HIM). J. Immunol. 153, 3295–3306.

Castigli E., Alt F. W., Davidson L., Bottaro A., Mizoguchi E., Bhan A. K. and Geha R. S. (1994) CD40-deficient mice generated by recombination-activating gene-2-deficient blastocyst complementation. Proc. Natl. Acad. Sci. U. S. A. 91, 12135–12139.

Chen C. Y. and Shyu A. B. (1995) AU-rich elements: characterization and importance in mRNA degradation. [Review] [42 refs]. Trends. Biochem. Sci. 20, 465–470.

Chen Z. Q., Hofker M. H. and Cox D. W. (1995) Defining the breakpoint of a multigene deletion in the immunoglobulin heavy chain gene cluster. Immunogenetics 41, 69–73.

Cheng G., Cleary A. M., Ye Z., Hong D. I., Lederman S. and Baltimore D. (1995) Involvement of CRAF1, a relative of TRAF, in CD40 signaling. Science 267, 1494–1497.

Cheng G. and Baltimore D. (1996) TANK, a co-inducer with TRAF2 of TNF- and CD40L-mediated NF-kappaB activation. Genes Dev. 10, 963–973.

Conley M. E., Larche M., Bonagura V. R., Lawton A. R., Buckley R., Fu S. M., Coustan-Smith E., Herrod H. G. and Campana D. (1994) Hyper IgM syndrome associated with defective CD40-mediated B cell activation. J. Clin. Invest. 94, 1404–1409.

Cox D. W., Billingsley G. D., Bale A. E., Donis-Keller H., Edwards J. H., Litt M., Mcbride W., Persichetti F., Spurr N. K., Weber J. L. and et al. (1995) CEPH consortium map of chromosome 14. *Cytogenet. Cell Genet.* 69, 175–178.

Cross S. H. and Bird A. P. (1995) CpG islands and genes. *Curr. Opin. Genet. Dev.* 5, 309–314.

Devergne O., Hatzivassiliou E., Izumi K. M., Kaye K. M., Kleijnen M. F., Kieff E. and Mosialos G. (1996) Association of TRAF1, TRAF2, and TRAF3 with an Epstein-Barr virus LMP1 domain important for B-lymphocyte transformation: role in NF-kappaB activation. *Mol. Cell Biol.* 16, 7098–7108.

Duckett C. S., Gedrich R. W., Gilfillan M. C. and Thompson C. B. (1997) Induction of nuclear factor kappaB by the CD30 receptor is mediated by TRAF1 and TRAF2. *Mol. Cell Biol.* 17, 1535–1542.

Eliopoulos A. G., Dawson C. W., Mosialos G., Floettmann J. E., Rowe M., Armitage R. J., Dawson J., Zapata J. M., Kerr D. J., Wakelam M. J., Reed J. C., Kieff E. and Young L. S. (1996) CD40-induced growth inhibition in epithelial cells is mimicked by Epstein-Barr Virus-encoded LMP1: involvement of TRAF3 as a common mediator. *Oncogene* 13, 2243–2254.

Force W. R., Cheung T. C. and Ware C. F. (1997) Dominant negative mutants of TRAF3 reveal an important role for the coiled coil domains in cell death signaling by the lymphotoxin-beta receptor. *J. Biol. Chem.* 272, 30835–30840.

Gardiner-Garden M. and Frommer M. (1987) CpG islands in vertebrate genomes. *J. Mol. Biol.* 196, 261–282.

Gedrich R. W., Gilfillan M. C., Duckett C. S., Van Dongen J. L. and Thompson C. B. (1996) CD30 contains two binding sites with different specificities for members of the tumor necrosis factor receptor-associated factor family of signal transducing proteins. *J. Biol. Chem.* 271, 12852–12858.

Han J., Brown T. and Beutler B. (1990) Endotoxin-responsive sequences control cachectin/tumor necrosis factor biosynthesis at the translational level. *J. Exp. Med.* 171, 465–475.

Hanissian S. H. and Geha R. S. (1997) Jak3 is associated with CD40 and is critical for CD40 induction of gene expression in B cells. *Immunity* 6, 379–387.

Hayashi Y., Pui C. H., Behm F. G., Fuchs A. H., Raimondi S. C., Kitchingman G. R., Mirro J., Jr. and Williams D. L. (1990) 14q32 translocations are associated with mixed-lineage expression in childhood acute leukemia. *Blood* 76, 150–156.

Hofker M. H., Walter M. A. and Cox D. W. (1989) Complete physical map of the human immunoglobulin heavy chain constant region gene complex. *Proc. Natl. Acad. Sci. U. S. A.* 86, 5567–5571.

Hofker M. H., Smith S., Nakamura Y., Teshima I., White R. and Cox D. W. (1990) Physical mapping of probes within 14q32, a subtelomeric region showing a high recombination frequency. *Genomics* 6, 33–38.

Hu H. M., O'Rourke K., Boguski M. S. and Dixit V. M. (1994) A novel RING finger protein interacts with the cytoplasmic domain of CD40. *J. Biol. Chem.* 269, 30069–30072.

Ishida T., Mizushima Si, Azuma S., Kobayashi N., Tojo T., Suzuki K., Aizawa S., Watanabe T., Mosialos G., Kieff E., Yamamoto T. and Inoue J. (1996) Identification of TRAF6, a novel tumor necrosis factor receptor-associated factor protein that mediates signaling from an amino-terminal domain of the CD40 cytoplasmic region. *J. Biol. Chem.* 271, 28745–28748.

Ishida T. K., Tojo T., Aoki T., Kobayashi N., Ohishi T., Watanabe T., Yamamoto T. and Inoue J. (1996) TRAF5, a novel tumor necrosis factor receptor-associated factor family protein, mediates CD40 signaling. *Proc. Natl. Acad. Sci. U. S. A.* 93, 9437–9442.

Kang H. K. and Cox D. W. (1996) Tandem repeats 3' of the IGHA genes in the human immunoglobulin heavy chain gene cluster. *Genomics* 35, 189–195.

Kashiwada M., Shirakata Y., Inoue J. I., Nakano H., Okazaki K., Okumura K., Yamamoto T., Nagaoka H. and Takemori T. (1998) Tumor necrosis factor receptor-associated factor 6 (TRAF6) stimulates extracellular signal-regulated kinase (ERK) activity in CD40 signaling along a ras-independent pathway. *J. Exp. Med.* 187, 237–244.

Kawabe T., Naka T., Yoshida K., Tanaka T., Fujiwara H., Suematsu S., Yosida N., Kishimoto T. and Kikutani H. (1994) The immune responses in CD40-deficient mice: impaired immunoglobulin class switching and germinal center formation. *Immunity* 1, 167–178.

Kawamata S., Hori T., Imura A., Takaori-Kondo A. and Uchiyama T. (1998) Activation of OX40 signal transduction pathways leads to tumor necrosis factor receptor-associated factor (TRAF) 2- and TRAF5-mediated NF-kappaB activation. *J. Biol. Chem.* 273, 5808–5814.

Kim S. J., Park K., Koeller D., Kim K. Y., Wakefield L. M., Sporn M. B. and Roberts A. B. (1992) Post-transcriptional regulation of the human transforming growth factor-beta 1 gene. *J. Biol. Chem.* 267, 13702–13707.

Kozak M. (1989a) Circumstances and mechanisms of inhibition of translation by secondary structure in eucaryotic mRNAs. *Mol. Cell Biol.* 9, 5134–5142.

Kozak M. (1989b) The scanning model for translation: an update. *J. Cell Biol.* 108, 229–241.

Krajewski S., Zapata J. M., Krajewska M., VanArsdale T., Shabaik A., Gascoyne R. D. and Reed J. C. (1997) Immunohistochemical analysis of in vivo patterns of TRAF-3 expression, a member of the TNF receptor-associated factor family. *J. Immunol.* 159, 5841–5852.

Kruys V., Wathelet M., Poupart P., Contreras R., Fiers W., Content J. and Huez G. (1987) The 3' untranslated region of the human interferon-beta mRNA has an inhibitory effect on translation. *Proc. Natl. Acad. Sci. U. S. A.* 84, 6030–6034.

Lederman S., Yellin M. J., Inghirami G., Lee J. J., Knowles D. M. and Chess L. (1992) Molecular interactions mediating T-B lymphocyte collaboration in human lymphoid follicles: Roles of T-B Activating Molecule (5c8 Antigen) and CD40 in contact-dependent Help. *J. Immunol.* 149, 3817–3826.

Lee S. Y., Kandala G., Liou M. L., Liou H. C. and Choi Y. (1996) CD30/TNF receptor-associated factor interaction: NF-kappa B activation and binding specificity. *Proc. Natl. Acad. Sci. U. S. A.* 93, 9699–9703.

Malinin N. L., Boldin M. P., Kovalenko A. V. and Wallach D. (1997) MAP3K-related kinase involved in NF-kappaB induction by TNF, CD95 and IL-1. *Nature* 385, 540–544.

Maniatis T., Fritsch E. F. and Sambook J. (1982) *Molecular cloning: A laboratory manual.* Cold Spring Harbor, Cold Spring Harbor, N.Y.

Menon A. G., Rutter J. L., von Sattel J. P., Synder H., Murdoch C., Blumenfeld A., Martuza R. L., von Deimling A., Gusella J. F. and Houseal T. W. (1997) Frequent loss of chromosome 14 in atypical and malignant meningioma: identification of a putative 'tumor progression' locus. *Oncogene* 14, 611–616.

Morio T., Hanissian S. and Geha R. S. (1995) Characterization of a 23-kDa protein associated with CD40. *Proc. Natl. Acad. Sci. U. S. A.* 92, 11633–11636.

Mosialos G., Birkenbach M., Yalamanchili R., VanArsdale T., Ware C. and Kieff E. (1995) The Epstein-Barr virus transforming protein LMP1 engages signaling proteins for the tumor necrosis factor receptor family. *Cell* 80, 389–399.

Motokura T., Bloom T., Kim H. G., Juppner H., Ruderman J. V., Kronenberg H. M. and Arnold A. (1991) A novel cyclin encoded by a bcl1-linked candidate oncogene. *Nature* 350, 512–515.

Nakano H., Oshima H., Chung W., Williams-Abbott L., Ware C. F., Yagita H. and Okumura K. (1996) TRAF5, an activator of NF-kappaB and putative signal transducer for the lymphotoxin-beta receptor. *J. Biol. Chem.* 271, 14661–14664.

Nakano H., Shindo M., Yamada K., Yoshida M. C., Santee S. M., Ware C. F., Jenkins N. A., Gilbert D. J., Yagita H., Copeland N. C. and Okumura K. (1997) Human TNF receptor-associated factor 5 (TRAF5): cDNA cloning, expression and assignment of the TRAF5 gene to chromosome 1q32. *Genomics* 42, 26–32.

Neri A., Chang C. C., Lombardi L., Salina M., Corradini P., Maiolo A. T., Chaganti R. S. and Dalla-Favera R. (1991) B cell lymphoma-associated chromosomal translocation involves candidate oncogene lyt-10, homologous to NF-kappa B p50. *Cell* 67, 1075–1087.

Ohno H., Takimoto G. and McKeithan T. W. (1990) The candidate proto-oncogene bcl-3 is related to genes implicated in cell lineage determination and cell cycle control. *Cell* 60, 991–997.

Parthasarathy L., Parthasarathy R. and Vadnal R. (1997) Molecular characterization of coding and untranslated regions of rat cortex lithium-sensitive myo-inositol monophosphatase cDNA. *Gene* 191, 81–87.

Regnier C. H., Tomasetto C., Moog-Lutz C., Chenard M. P., Wendling C., Basset P. and Rio M. C. (1995) Presence of a new conserved domain in CART1, a novel member of the tumor necrosis factor receptor-associated protein family, which is expressed in breast carcinoma. *J. Biol. Chem.* 270, 25715–25721.

Regnier C. H., Song H. Y., Gao X., Goeddel D. V., Cao Z. and Rothe M. (1997) Identification and characterization of an IkappaB kinase. *Cell* 90, 373–383.

Renshaw B. R., Fanslow W. C., 3rd, Armitage R. J., Campbell K. A., Liggitt D., Wright B., Davison B. L. and Maliszewski C. R. (1994) Humoral immune responses in CD40 ligand-deficient mice. *J. Exp. Med.* 180, 1889–1900.

Romeo D. S., Park K., Roberts A. B., Sporn M. B. and Kim S. J. (1993) An element of the transforming growth factor-beta 1 5'-untranslated region represses translation and specifically binds a cytosolic factor. *Mol. Endocrinol.* 7, 759–766.

Rothe M., Wong S. C., Henzel W. J. and Goeddel D. V. (1994) A novel family of putative signal transducers associated with the cytoplasmic domain of the 75 kDa tumor necrosis factor receptor. *Cell* 78, 681–692.

Rothe M., Sarma V., Dixit V. M. and Goeddel D. V. (1995) TRAF2-mediated activation of NF-kappa-B by TNF Receptor 2 and CD40. *Science* 269, 1424–1427.

Rothe M., Xiong J., Shu H. B., Williamson K., Goddard A. and Goeddel D. V. (1996) I-TRAF is a novel TRAF-interacting protein that regulates TRAF-mediated signal transduction. *Proc. Natl. Acad. Sci. U. S. A.* 93, 8241–8246.

Sato T., Irie S. and Reed J. C. (1995) A novel member of the TRAF family of putative signal transducing proteins binds to the cytosolic domain of CD40. *FEBS Letters* 358, 113–118.

Schullerus D., Herbers J., Chudek J., Kanamaru H. and Kovacs G. (1997) Loss of heterozygosity at chromosomes 8p, 9p, and 14q is associated with stage and grade of non-papillary renal cell carcinomas. *J. Pathol.* 183, 151–155.

Schwerdtle R. F., Winterpacht A., Storkel S., Brenner W., Hohenfellner R., Zabel B., Huber C. and Decker H. J. (1997) Loss of heterozygosity studies and deletion mapping identify two putative chromosome 14q tumor suppressor loci in renal oncocytomas. *Cancer Res.* 57, 5009–5012.

Shaw G. and Kamen R. (1986) A conserved AU sequence from the 3' untranslated region of GM-CSF mRNA mediates selective mRNA degradation. *Cell* 46, 659–667.

Siegel J. P. and Mostowski H. S. (1990) A bioassay for the measurement of human interleukin-4. *J. Immunol. Methods* 132, 287–25 295.

Siemienski K., Peters N., Scheurich P. and Wajant H. (1997) Organization of the human tumour necrosis factor receptor-associated factor 1 (TRAF1) gene and mapping to chromosome 9q33–34. *Gene* 195, 35–39.

Simon M., von Deimling A., Larson J. J., Wellenreuther R., Kaskel P., Waha A., Warnick R. E., Tew J. M., Jr. and Menon A. G. (1995) Allelic losses on chromosomes 14, 10, and 1 in atypical and malignant meningiomas: a genetic model of meningioma progression. *Cancer Res.* 55, 4696–4701.

Song H. Y., Regnier C. H., Kirschning C. J., Goeddel D. V. and Rothe M. (1997) Tumor necrosis factor (TNF)-mediated kinase cascades: bifurcation of nuclear factor-kappaB and c-jun N-terminal kinase (JNK/SAPK) pathways at TNF receptor-associated factor 2. *Proc. Natl. Acad. Sci. U. S. A.* 94, 9792–9796.

Takeuchi M., Rothe M. and Goeddel D. V. (1996) Anatomy of TRAF2. Distinct domains for nuclear factor-kappaB activation and association with tumor necrosis factor signaling proteins. *J. Biol. Chem.* 271, 19935–19942.

Taub R., Kirsch I., Morton C., Lenoir G., Swan D., Tronick S., Aaronson S. and Leder P. (1982) Translocation of the c-myc gene into the immunoglobulin heavy chain locus in human Burkitt lymphoma and murine plasmacytoma cells. *Proc. Natl. Acad. Sci. U. S. A.* 79, 7837–7841.

Tse J. Y., Ng H. K., Lau K. M., Lo K. W., Poon W. S. and Huang D. P. (1997) Loss of heterozygosity of chromosome 14q in low- and high-grade meningiomas. *Hum. Pathol.* 28, 779–785.

Tsujimoto Y., Finger L. R., Yunis J., Nowell P. C. and Croce C. M. (1984) Cloning of the chromosome breakpoint of neoplastic B cells with the t(14;18) chromosome translocation. *Science* 226, 1097–1099.

Vanarsdale T. L., VanArsdale S. L., Force W. R., Walter B. N., Mosialos G., Kieff E., Reed J. C. and Ware C. F. (1997) Lymphotoxin-beta receptor signaling complex: role of tumor necrosis factor receptor-associated factor 3 recruitment in cell death and activation of nuclear factor kappaB. *Proc. Natl. Acad. Sci. U. S. A.* 94, 2460–2465.

Wang X., Bornslaeger E. A., Haub O., Tomihara-Newberger C., Lonberg N., Dinulos M. B., Disteche C. M., Copeland N., Gilbert D. J., Jenkins N. A. and Lacy E. (1996) A candidate gene for the amnionless gastrulation stage mouse mutation encodes a TRAF-related protein. *Dev. Biol.* 177, 274–290.

Wenger R. H., Rolfs A., Spielmann P., Zimmermann D. R. and Gassmann M. (1998) Mouse hypoxia-inducible factor-1 alpha is encoded by two different mRNA isoforms: expression from a tissue-specific and a housekeeping-type promoter. *Blood* 91, 3471–3480.

Wilson T. and Treisman R. (1988) Removal of poly(A) and consequent degradation of c-fos mRNA facilitated by 3' AU-rich sequences. *Nature* 336, 396–399.

Wiman K. G., Clarkson B., Hayday A. C., Saito H., Tonegawa S. and Hayward W. S. (1984) Activation of a translocated c-myc gene: role of structural alterations in the upstream region. *Proc. Natl. Acad. Sci. U. S. A.* 81, 6798–6802.

Wintle R. F., Nygaard T. G., Herbrick J. A., Kvaloy K. and Cox D. W. (1997) Genetic polymorphism and recombination in the subtelomeric region of chromosome 14q. *Genomics* 40, 409–414.

Xu J., Foy T. M., Laman J. D., Elliott E. A., Dunn J. J., Waldschmidt T. J., Elsemore J., Noelle R. J. and Flavell R. A. (1994) Mice deficient for the CD40 ligand. *Immunity* 1, 423–431.

Xu Y., Cheng G. and Baltimore D. (1996) Targeted disruption of TRAF3 leads to postnatal lethality and defective T-dependent immune responses. *Immunity* 5, 407–415.

Ye B. H., Lista F., Lo Coco F., Knowles D. M., Offit K., Chaganti R. S. and Dalla-Favera R. (1993) Alterations of a zinc finger-encoding gene, BCL-6, in diffuse large-cell lymphoma. *Science* 262, 747–750.

Yellin M. J., Lee J. J., Chess L. and Lederman S. (1991) A human CD4-leukemic subclone with contact dependent helper function. *J. Immunol.* 147, 3389–3395.

Yu F., Warburton D., Wellington S. and Danziger R. S. (1996) Assignment of GUCIA2, the gene coding for the alpha 2 subunit of soluble guanylyl cyclase, to position 11q21–q22 on human chromosome 11. *Genomics* 33, 334–336.

What is claimed is:

1. An isolated nucleic acid molecule encoding a protein consisting of the amino acid sequence shown in FIG. 16 (SEQ ID NO:36).

2. The isolated nucleic acid molecule of claim 1, wherein the molecule is DNA or cDNA.

3. A vector comprising the isolated nucleic acid molecule of claim 1 operably linked to a transcriptional control sequence.

4. The vector of claim 3, wherein the vector is a plasmid.

* * * * *

SEQUENCE LISTING

```
<160> NUMBER OF SEQ ID NOS: 43

<210> SEQ ID NO 1
<211> LENGTH: 20
<212> TYPE: DNA
<213> ORGANISM: Artificial Sequence
<220> FEATURE:
<223> OTHER INFORMATION: Description of Artificial  Sequence:   Oligo
      Primer

<400> SEQUENCE: 1
ggccacgcgt cgactagtac                                                      20

<210> SEQ ID NO 2
<211> LENGTH: 38
<212> TYPE: DNA
<213> ORGANISM: Artificial Sequence
<220> FEATURE:
<223> OTHER INFORMATION: Description of Artificial  Sequence:   Forward
      Primer or Polymerase Chain Reaction .

<400> SEQUENCE: 2
gcggaattcg gtaccaccgt ggaggacaag tacaagtg                                  38

<210> SEQ ID NO 3
<211> LENGTH: 40
<212> TYPE: DNA
<213> ORGANISM: Artificial Sequence
<220> FEATURE:
<223> OTHER INFORMATION: Description of Artificial  Sequence:   Reverse
      Primer Coiled or Polymerase Chain Reaction.

<400> SEQUENCE: 3
cgcggatcca agcttctagt tctgccggaa gggccggatc                                40

<210> SEQ ID NO 4
<211> LENGTH: 24
<212> TYPE: DNA
<213> ORGANISM: Artificial Sequence
<220> FEATURE:
<223> OTHER INFORMATION: Description of Artificial  Sequence:   TRAF-3
      Specific Primer 3 Bend-2

<400> SEQUENCE: 4
ttgaaacaaa attgcactct tgaa                                                 24

<210> SEQ ID NO 5
```

<211> LENGTH: 28
<212> TYPE: DNA
<213> ORGANISM: Artificial Sequence
<220> FEATURE:
<223> OTHER INFORMATION: Description of Artificial Sequence:
      Oligonucleotide FF7GEN

<400> SEQUENCE: 5
aaatgtacag cgtgtcaaga gagcatcg                                    28

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 6
gtctttgtgg cccaaactgt tctagaaaat gg                               32

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 7
gatttgggtg acagaccctc att                                         23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Oligo
      (dT) Primer

<400> SEQUENCE: 8
ggccacgcgt cgactagtac                                             20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 9
atgcagttct aggcacagcc                                             20

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Primer
      F1gen

<400> SEQUENCE: 10
gagagaaatt ctggctcttc agatctattg tcgg                             34

<210> SEQ ID NO 11
<211> LENGTH: 25

```
<210> SEQ ID NO 11
<211> LENGTH: 25
<212> TYPE: DNA
<213> ORGANISM: Artificial Sequence
<220> FEATURE:
<223> OTHER INFORMATION: Description of Artificial  Sequence:   Primer
      FR8gen

<400> SEQUENCE: 11
tgcagtcagg acgcacacat ggaag                                              25

<210> SEQ ID NO 12
<211> LENGTH: 18
<212> TYPE: DNA
<213> ORGANISM: Human

<400> SEQUENCE: 12
tttattttac agatgagg                                                      18

<210> SEQ ID NO 13
<211> LENGTH: 18
<212> TYPE: DNA
<213> ORGANISM: Human

<400> SEQUENCE: 13
ttttcccgac agaactcc                                                      18

<210> SEQ ID NO 14
<211> LENGTH: 18
<212> TYPE: DNA
<213> ORGANISM: Human

<400> SEQUENCE: 14
tttgccctgc agctcttc                                                      18

<210> SEQ ID NO 15
<211> LENGTH: 18
<212> TYPE: DNA
<213> ORGANISM: Human

<400> SEQUENCE: 15
tttcattttc aggtgttt                                                      18

<210> SEQ ID NO 16
<211> LENGTH: 18
<212> TYPE: DNA
<213> ORGANISM: Human

<400> SEQUENCE: 16
tctgtcttac aggtgcat                                                      18

<210> SEQ ID NO 17
<211> LENGTH: 18
<212> TYPE: DNA
<213> ORGANISM: Human

<400> SEQUENCE: 17
ctctctctgt agaaacac                                                      18

<210> SEQ ID NO 18
<211> LENGTH: 18
<212> TYPE: DNA
<213> ORGANISM: Human

<400> SEQUENCE: 18
ttcccgttgc agttgagt                                                      18
```

```
<210> SEQ ID NO 19
<211> LENGTH: 18
<212> TYPE: DNA
<213> ORGANISM: Human

<400> SEQUENCE: 19
ttgctctcgc agggggaca                                              18

<210> SEQ ID NO 20
<211> LENGTH: 18
<212> TYPE: DNA
<213> ORGANISM: Human

<400> SEQUENCE: 20
tttctttttt aggtttcc                                               18

<210> SEQ ID NO 21
<211> LENGTH: 18
<212> TYPE: DNA
<213> ORGANISM: Human

<400> SEQUENCE: 21
ttggtttgga agcgagtg                                               18

<210> SEQ ID NO 22
<211> LENGTH: 18
<212> TYPE: DNA
<213> ORGANISM: Human

<400> SEQUENCE: 22
cacctgtggc aggcctgc                                               18

<210> SEQ ID NO 23
<211> LENGTH: 18
<212> TYPE: DNA
<213> ORGANISM: Human

<400> SEQUENCE: 23
ccacccgtga gcaagaca                                               18

<210> SEQ ID NO 24
<211> LENGTH: 18
<212> TYPE: DNA
<213> ORGANISM: Human

<400> SEQUENCE: 24
cgcgaggtgt aaggggcc                                               18

<210> SEQ ID NO 25
<211> LENGTH: 18
<212> TYPE: DNA
<213> ORGANISM: Human

<400> SEQUENCE: 25
gaagaggttt gctctcag                                               18

<210> SEQ ID NO 26
<211> LENGTH: 18
<212> TYPE: DNA
<213> ORGANISM: Human

<400> SEQUENCE: 26
```

-continued

```
gctgaggtag gcgccctc                                              18

<210> SEQ ID NO 27
<211> LENGTH: 18
<212> TYPE: DNA
<213> ORGANISM: Human

<400> SEQUENCE: 27
gataaggtat tctggggt                                              18

<210> SEQ ID NO 28
<211> LENGTH: 18
<212> TYPE: DNA
<213> ORGANISM: Human

<400> SEQUENCE: 28
ctgctggtga gtagcaaa                                              18

<210> SEQ ID NO 29
<211> LENGTH: 18
<212> TYPE: DNA
<213> ORGANISM: Human

<400> SEQUENCE: 29
ctgcaggtgc gggtcctc                                              18

<210> SEQ ID NO 30
<211> LENGTH: 18
<212> TYPE: DNA
<213> ORGANISM: Human

<400> SEQUENCE: 30
agcgaggtag gggcggcc                                              18

<210> SEQ ID NO 31
<211> LENGTH: 18
<212> TYPE: DNA
<213> ORGANISM: Human

<400> SEQUENCE: 31
tttcaggtca gtatccga                                              18

<210> SEQ ID NO 32
<211> LENGTH: 18
<212> TYPE: DNA
<213> ORGANISM: Human

<400> SEQUENCE: 32
aagaaggtgg gctgcaca                                              18

<210> SEQ ID NO 33
<211> LENGTH: 18
<212> TYPE: DNA
<213> ORGANISM: Human

<400> SEQUENCE: 33
ttacaggtaa gaatctta                                              18

<210> SEQ ID NO 34
<211> LENGTH: 18
<212> TYPE: DNA
<213> ORGANISM: Human

<400> SEQUENCE: 34
```

```
acacaggtga ggcagggg                                                      18

<210> SEQ ID NO 35
<211> LENGTH: 2065
<212> TYPE: DNA
<213> ORGANISM: Human

<400> SEQUENCE: 35
cgagggagcg cggcgcggcc gccgcgtgcg cgagccgggg ttgcagccca g ccgggactt     60
tccagccggc ggcagccgcg gcggccgccg gctcttcccc gccccccgtc a tggggcagc    120
ccggggagca gaacgctgcg gaccgcggcg gaggacgcgc ccggcgcccc t gagccggcc    180
gagcggcgac ggaccgcgag aactcctctt tcctaaaatg gagtcgagta a aaagatgga    240
ctctcctggc gcgctgcaga ctaacccgcc gctaaagctg cacactgacc g tagtgctgg    300
gacgccagtt tttgtccctg aacaaggagg ttacaaggaa aagtttgtga a gaccgtgga    360
ggacaagtac aagtgtgaga agtgccacct ggtgctgtgc agcccgaagc a gaccgagtg    420
tgggcaccgc ttctgcgaga gctgcatggc ggccctgctg agctcttcaa g tccaaaatg    480
tacagcgtgt caagagagca tcgttaaaga taaggtgttt aaggataatt g ctgcaagag    540
agaaattctg gctcttcaga tctattgtcg gaatgaaagc agaggttgtg c agagcagtt    600
aacgctggga catctgctgg tgcatttaaa aaatgattgc cattttgaag a acttccatg    660
tgtgcgtcct gactgcaaag aaaaggtctt gaggaaagac ctgcgagacc a cgtggagaa    720
ggcgtgtaaa taccgggaag ccacatgcag ccactgcaag agtcaggttc c gatgatcgc    780
gctgcagcga gtgatagaca gccaagcaga gaaactgaag gagcttgaca a ggagatccg    840
gcccttccgg cagaactggg aggaagcaga cagcatgaag agcagcgtgg a gtccctcca    900
gaaccgcgtg accgagctgg agagcgtgga caagagtgcg gggcaagtgg c tcggaacac    960
aggcctgctg gagtcccagc tgagccggca tgaccagatg ctgagtgtgc a ccacatccg   1020
cctagccgac atggacctgc gcttccaggt cctggagacc gccagctaca a tggagtgct   1080
catctggaag attcgcgact acaagcggcg gaagcaggag gccgtcatgg g gaagaccct   1140
gtcccttttac agccagcctt tctacactgg ttactttggt tataagatgt g tgccagggt   1200
ctacctgaac ggggacggga tggggaaggg gacgcacttg tcgctgtttt t tgtcatcat   1260
gcgtggagaa tatgatgccc tgcttccttg gccgtttaag cagaaagtga c actcatgct   1320
gatggatcag gggtcctctc gacgtcattt gggagatgca ttcaagcccg a ccccaacag   1380
cagcagcttc aagaagccca ctggagagat gaatatcgcc tctggctgcc c agtctttgt   1440
ggcccaaaact gttctagaaa atgggacata tattaaagat gatacaattt t tattaaagt   1500
catagtggat acttcggatc tgccccatcc ctgataagta gctggggagg t ggatttagc   1560
agaaggcaac tcctctgggg gatttgaacc ggtctgtctt cactgaggtc c tcgcgctca   1620
gaaaaggacc ttgtgagacg gaggaagcgg cagaaggcgg acgcgtgccg g cgggaggag   1680
ccacgcgtga gcacacctga cacgttttat aatagactag ccacacttca c tctgaagaa   1740
ttatttatcc ttcaacaaga taaatattgc tgtcagagaa ggttttcatt t tcattttta   1800
aagatctagt taattaaggt ggaaaacata tatgctaaac aaaagaaaca t gattttttct  1860
tccttaaact tgaacaccaa aaaacacac acacacacac acgtggggat a gctggacat   1920
gtcagcatgt taagtaaaag gagaatttat gaaatagtaa tgcaattctg a tatcttctt   1980
tctaaaattc aagagtgcaa ttttgtttca aatacagtat attgtctatt t ttaaggcct   2040
```
ccaaaaaaaa aaaaaattcc ggccg					2065

<210> SEQ ID NO 36
<211> LENGTH: 438
<212> TYPE: PRT
<213> ORGANISM: Human

<400> SEQUENCE: 36

Met Glu Ser Ser Lys Lys Met Asp Ser Pro Gly Ala Leu Gln Thr Asn
 1               5                  10                  15

Pro Pro Leu Lys Leu His Thr Asp Arg Ser Ala Gly Thr Pro Val Phe
             20                  25                  30

Val Pro Glu Gln Gly Gly Tyr Lys Glu Lys Phe Val Lys Thr Val Glu
         35                  40                  45

Asp Lys Tyr Lys Cys Glu Lys Cys His Leu Val Leu Cys Ser Pro Lys
     50                  55                  60

Gln Thr Glu Cys Gly His Arg Phe Cys Glu Ser Cys Met Ala Ala Leu
 65                  70                  75                  80

Leu Ser Ser Ser Pro Lys Cys Thr Ala Cys Gln Glu Ser Ile Val
             85                  90                  95

Lys Asp Lys Val Phe Lys Asp Asn Cys Cys Lys Arg Glu Ile Leu Ala
            100                 105                 110

Leu Gln Ile Tyr Cys Arg Asn Glu Ser Arg Gly Cys Ala Glu Gln Leu
        115                 120                 125

Thr Leu Gly His Leu Leu Val His Leu Lys Asn Asp Cys His Phe Glu
130                 135                 140

Glu Leu Pro Cys Val Arg Pro Asp Cys Lys Glu Lys Val Leu Arg Lys
145                 150                 155                 160

Asp Leu Arg Asp His Val Glu Lys Ala Cys Lys Tyr Arg Glu Ala Thr
                165                 170                 175

Cys Ser His Cys Lys Ser Gln Val Pro Met Ile Ala Leu Gln Arg Val
            180                 185                 190

Ile Asp Ser Gln Ala Glu Lys Leu Lys Glu Leu Asp Lys Glu Ile Arg
        195                 200                 205

Pro Phe Arg Gln Asn Trp Glu Glu Ala Asp Ser Met Lys Ser Ser Val
210                 215                 220

Glu Ser Leu Gln Asn Arg Val Thr Glu Leu Glu Ser Val Asp Lys Ser
225                 230                 235                 240

Ala Gly Gln Val Ala Arg Asn Thr Gly Leu Leu Glu Ser Gln Leu Ser
                245                 250                 255

Arg His Asp Gln Met Leu Ser Val His Asp Ile Arg Leu Ala Asp Met
            260                 265                 270

Asp Leu Arg Phe Gln Val Leu Glu Thr Ala Ser Tyr Asn Gly Val Leu
        275                 280                 285

Ile Trp Lys Ile Arg Asp Tyr Lys Arg Arg Lys Gln Glu Ala Val Met
290                 295                 300

Gly Lys Thr Leu Ser Leu Tyr Ser Gln Pro Phe Tyr Thr Gly Tyr Phe
305                 310                 315                 320

Gly Tyr Lys Met Cys Ala Arg Val Tyr Leu Asn Gly Asp Gly Met Gly
                325                 330                 335

Lys Gly Thr His Leu Ser Leu Phe Phe Val Ile Met Arg Gly Glu Tyr
            340                 345                 350

Asp Ala Leu Leu Pro Trp Pro Phe Lys Gln Lys Val Thr Leu Met Leu
        355                 360                 365

| Met | Asp | Gln | Gly | Ser | Ser | Arg | Arg | His | Leu | Gly | Asp | Ala | Phe | Lys | Pro |
|---|---|---|---|---|---|---|---|---|---|---|---|---|---|---|---|
| 370 | | | | | 375 | | | | | 380 | | | | | |

| Asp | Pro | Asn | Ser | Ser | Phe | Lys | Lys | Pro | Thr | Gly | Glu | Met | Asn | Ile |
|---|---|---|---|---|---|---|---|---|---|---|---|---|---|---|
| 385 | | | | 390 | | | | | 395 | | | | | 400 |

| Ala | Ser | Gly | Cys | Pro | Val | Phe | Val | Ala | Gln | Thr | Val | Leu | Glu | Asn | Gly |
|---|---|---|---|---|---|---|---|---|---|---|---|---|---|---|---|
| | | | | 405 | | | | | 410 | | | | | 415 | |

| Thr | Tyr | Ile | Lys | Asp | Asp | Thr | Ile | Phe | Ile | Lys | Val | Ile | Val | Asp | Thr |
|---|---|---|---|---|---|---|---|---|---|---|---|---|---|---|---|
| | | | 420 | | | | | 425 | | | | | 430 | | |

| Ser | Asp | Leu | Pro | Asp | Pro |
|---|---|---|---|---|---|
| | | 435 | | | |

<210> SEQ ID NO 37
<211> LENGTH: 1793
<212> TYPE: DNA
<213> ORGANISM: Human

<400> SEQUENCE: 37

| cgagggagcg | cggcgcggcc | gccgcgtgcg | cgagccgggg | ttgcagccca | g ccgggactt | 60 |
|---|---|---|---|---|---|---|
| tccagccggc | ggcagccgcg | gcggccgccg | gctcttcccc | gccccccgtc | a tggggcagc | 120 |
| ccggggagca | gaacgctgcg | gaccgcggcg | gaggacgcgc | ccggcgcccc | t gagccggcc | 180 |
| gagcggcgac | ggaccgcgag | aactcctctt | tcctaaaatg | gagtcgagta | a aaagatgga | 240 |
| ctctcctggc | gcgctgcaga | ctaacccgcc | gctaaagctg | cacactgacc | g tagtgctgg | 300 |
| gacgccagtt | tttgtccctg | aacaaggagg | ttacaaggaa | aagtttgtga | a gaccgtgga | 360 |
| ggacaagtac | aagtgtgaga | agtgccacct | ggtgctgtgc | agcccgaagc | a gaccgagtg | 420 |
| tgggcaccgc | ttctgcgaga | gctgcatggc | ggccctgctg | agctccttca | a gtccaaaat | 480 |
| gtacagcgtg | tcaagagagc | atcgttaaag | ataagcgagt | gatagacagc | c aagcagaga | 540 |
| aactgaagga | gcttgacaag | gagatccggc | ccttccggca | gaactgggag | g aagcagaca | 600 |
| gcatgaagag | cagcgtggag | tccctccaga | accgcgtgac | cgagctggag | a gcgtggaca | 660 |
| agagtgcggg | gcaagtggct | cggaacacag | gcctgctgga | gtcccagctg | a gccggcatg | 720 |
| accagatgct | gagtgtgcac | gacatccgcc | tagccgacat | ggacctgcgc | t tccaggtcc | 780 |
| tggagaccgc | cagctacaat | ggagtgctca | tctggaagat | tcgcgactac | a gcggcgga | 840 |
| agcaggaggc | cgtcatgggg | aagaccctgt | ccctttacag | ccagccttc | t acactggtt | 900 |
| actttggcta | aagatgtgt | gccagggtct | acctgaacgg | ggacgggatg | g ggaagggga | 960 |
| cgcacttgtc | gctgtttttt | gtcatcatgc | gtggagaata | tgatgccctg | c ttccttggc | 1020 |
| cgtttaagca | gaaagtgaca | ctcatgctga | tggatcaggg | gtcctctcga | c gtcatttgg | 1080 |
| gagatgcatt | caagcccgac | cccaacagca | gcagcttcaa | gaagcccact | g gagagatga | 1140 |
| atatcgcctc | tggctgccca | gtctttgtgg | cccaaactgt | tctagaaaat | g ggacatata | 1200 |
| ttaaagatga | tacaattttt | attaaactca | tagtggatac | ttcggatctg | c ccgatccct | 1260 |
| gataagtagc | tggggaggtg | gatttagcag | aaggcaactc | ctctggggga | t ttgaaccgg | 1320 |
| tctgtcttca | ctgaggtcct | cgcgctcaga | aaaggacctt | gtgagacgga | g gaagcggca | 1380 |
| gaaggcggac | ccgtgccggc | gggaggagcc | acgcgtgagc | acacctgaca | c gttttataa | 1440 |
| tagactagcc | acacttcact | ctgaagaatt | atttatcctt | caacaagata | a atattgctg | 1500 |
| tcagagaagg | ttttcatttt | cattttaaa | gatctagtta | attaaggtgg | a aaacatata | 1560 |
| tgctaaacaa | aagaaacatg | atttttcttc | cttaaacttg | aacaccaaaa | a aacacacac | 1620 |
| acacacacac | gtggggatag | ctggacatgt | cagcatgtta | agtaaaagga | g aatttatga | 1680 |

-continued

```
aatagtaatg caattctgat atcttctttc taaaattcaa gagtgcaatt t tgtttcaaa    1740 tacagtatat tgtctatttt taaggcctcc aaaaaaaaaa aaaattccgg c cg           1793
```

<210> SEQ ID NO 38
<211> LENGTH: 347
<212> TYPE: PRT
<213> ORGANISM: Human

<400> SEQUENCE: 38

```
Met Glu Ser Ser Lys Lys Met Asp Ser Pro G ly Ala Leu Gln Thr Asn
 1               5                  10                  15

Pro Pro Leu Lys Leu His Thr Asp Arg Ser A la Gly Thr Pro Val Phe
             20                  25                  30

Val Pro Glu Gln Gly Gly Tyr Lys Glu Lys P he Val Lys Thr Val Glu
         35                  40                  45

Asp Lys Tyr Lys Cys Glu Lys Cys His Leu V al Leu Cys Ser Pro Lys
     50                  55                  60

Gln Thr Glu Cys Gly His Arg Phe Cys Glu S er Cys Met Ala Ala Leu
 65                  70                  75                  80

Leu Ser Ser Ser Pro Lys Cys Thr Ala C ys Gln Glu Ser Ile Val
                 85                  90                  95

Lys Asp Lys Arg Val Ile Asp Ser Gln Ala G lu Lys Leu Lys Glu Leu
                100                 105                 110

Asp Lys Glu Ile Arg Pro Phe Arg Gln Asn T rp Glu Glu Ala Asp Ser
            115                 120                 125

Met Lys Ser Ser Val Glu Ser Leu Gln Asn A rg Val Thr Glu Leu Glu
        130                 135                 140

Ser Val Asp Lys Ser Ala Gly Gln Val Ala A rg Asn Thr Gly Leu Leu
145                 150                 155                 160

Glu Ser Gln Leu Ser Arg His Asp Gln Met L eu Ser Val His Asp Ile
                165                 170                 175

Arg Leu Ala Asp Met Asp Leu Arg Glu Gln V al Leu Glu Thr Ala Ser
            180                 185                 190

Tyr Asn Gly Val Leu Ile Trp Lys Ile Arg A sp Tyr Lys Arg Arg Lys
        195                 200                 205

Gln Glu Ala Val Met Gly Lys Thr Leu Ser L eu Tyr Ser Gln Pro Phe
    210                 215                 220

Tyr Thr Gly Tyr Phe Gly Tyr Lys Met Cys A la Arg Val Tyr Leu Asn
225                 230                 235                 240

Gly Asp Gly Met Gly Lys Gly Thr His Leu S er Leu Phe Phe Val Ile
                245                 250                 255

Met Arg Gly Glu Tyr Asp Ala Leu Leu Pro T rp Pro Phe Lys Gln Lys
            260                 265                 270

Val Thr Leu Met Leu Met Asp Gln Gly Ser S er Arg Arg His Leu Gly
        275                 280                 285

Asp Ala Phe Lys Pro Asp Pro Asn Ser Ser S er Phe Lys Lys Pro Thr
    290                 295                 300

Gly Glu Met Asn Ile Ala Ser Gly Cys Pro V al Phe Val Ala Gln Thr
305                 310                 315                 320

Val Leu Glu Asn Gly Thr Tyr Ile Lys Asp A sp Thr Ile Phe Ile Lys
                325                 330                 335

Val Ile Val Asp Thr Ser Asp Leu Pro Asp P ro
            340                 345
```

```
<210> SEQ ID NO 39
<211> LENGTH: 6
<212> TYPE: RNA
<213> ORGANISM: Homo sapiens

<400> SEQUENCE: 39 aauaaa                                                                  6

<210> SEQ ID NO 40
<211> LENGTH: 5
<212> TYPE: RNA
<213> ORGANISM: Homo Sapien

<400> SEQUENCE: 40 auuua                                                                   5

<210> SEQ ID NO 41
<211> LENGTH: 5
<212> TYPE: RNA
<213> ORGANISM: Homo Sapien

<400> SEQUENCE: 41 auuua                                                                   5

<210> SEQ ID NO 42
<211> LENGTH: 6
<212> TYPE: RNA
<213> ORGANISM: Homo Sapien

<400> SEQUENCE: 42 aguaaa                                                                  6

<210> SEQ ID NO 43
<211> LENGTH: 6
<212> TYPE: RNA
<213> ORGANISM: Homo Sapien

<400> SEQUENCE: 43 aauaca                                                                  6
```